United States Patent
Sung et al.

(10) Patent No.: US 10,717,985 B2
(45) Date of Patent: Jul. 21, 2020

(54) METHODS FOR CONFERRING OR ENHANCING HERBICIDE RESISTANCE ON PLANTS AND/OR ALGA WITH PROTOPORPHYRINOGEN OXIDASE VARIANTS

(71) Applicant: FARM HANNONG CO., LTD., Seoul (KR)

(72) Inventors: Soon-Kee Sung, Daejeon (KR); Joonseon Yoon, Daejeon (KR); Yunjung Han, Daejeon (KR)

(73) Assignee: FARM HANNONG CO., LTD., Seoul (KR)

( * ) Notice: Subject to any disclaimer, the term of this patent is extended or adjusted under 35 U.S.C. 154(b) by 95 days.

(21) Appl. No.: 15/532,194

(22) PCT Filed: Dec. 16, 2015

(86) PCT No.: PCT/KR2015/013812
§ 371 (c)(1),
(2) Date: Jun. 1, 2017

(87) PCT Pub. No.: WO2016/099153
PCT Pub. Date: Jun. 23, 2016

(65) Prior Publication Data
US 2017/0327837 A1    Nov. 16, 2017

(30) Foreign Application Priority Data
Dec. 16, 2014  (KR) .................. 10-2014-0181791

(51) Int. Cl.
*C12N 15/82* (2006.01)
*C12N 9/02* (2006.01)

(52) U.S. Cl.
CPC ......... *C12N 15/8274* (2013.01); *C12N 9/001* (2013.01); *C12Y 103/03004* (2013.01); *C12Y 103/00* (2013.01)

(58) Field of Classification Search
None
See application file for complete search history.

(56) References Cited

U.S. PATENT DOCUMENTS 5,859,348 A * 1/1999 Penner ............... A01H 1/04
435/410
6,308,458 B1   10/2001 Volrath et al.
(Continued)

FOREIGN PATENT DOCUMENTS

CN   102321640 A   1/2012
CN   103740663 A   4/2014
(Continued)

OTHER PUBLICATIONS

GenBank Accession No. AFZ07847. protoporphyrinogen oxidase [Oscillatoria nigro-viridis PCC 7112]. Published Jul. 22, 2013. pp. 1-2.*

(Continued)

*Primary Examiner* — Ashley K Buran
(74) *Attorney, Agent, or Firm* — Lucas & Mercanti, LLP

(57) ABSTRACT

Provided are methods for conferring and/or enhancing herbicide resistance on plants or algae including agricultural crops by introducing prokaryote-derived protoporphynnogen oxidase variants.

15 Claims, 25 Drawing Sheets
Specification includes a Sequence Listing.

(56) References Cited

U.S. PATENT DOCUMENTS

| | | | |
|---|---|---|---|
| 6,808,904 | B2 | 10/2004 | Ward et al. |
| 7,563,950 | B2 | 7/2009 | Matsushima et al. |
| 8,129,589 | B2 | 3/2012 | Tanaka et al. |
| 2010/0251432 | A1 | 9/2010 | Lira et al. |
| 2013/0189984 | A1 | 7/2013 | Xi et al. |
| 2015/0252379 | A1 | 9/2015 | Hutzler et al. |

FOREIGN PATENT DOCUMENTS

| | | | | |
|---|---|---|---|---|
| CN | 103740664 | A | 4/2014 | |
| JP | 2010-526535 | A | 8/2010 | |
| JP | 2014504855 | A | 2/2014 | |
| KR | 100559155 | B1 | 3/2006 | |
| WO | 2010/027506 | A2 | 3/2010 | |
| WO | 2011085221 | A2 | 7/2011 | |
| WO | 2013189984 | A2 | 12/2013 | |
| WO | WO-2013189984 | A2 * | 12/2013 | ..... C12Y 103/03004 |

OTHER PUBLICATIONS

Protoporphyrinogen oxidase [*Halothece* sp. PCC 7418]. GenBank Accession No. WP_015224927.1. pp. 1. (May 19, 2013).*

International Search Report and Written Opinion for International Application No. PCT/KR2015/013812 (11 pages) (dated Mar. 30, 2016).

Li et al., "Development of Protoporphyrinogen Oxidase as an Efficient Selection Marker for Agrobacterium tumefaciens—Mediated Transformation of Maize", Plant Physiology, 2003, vol. 133, pp. 736-747.

Watanabe et al., "Dual Targeting of Spinach Protoporphyrinogen Oxidase II to Mitochondria and Chloroplasts by Alternative Use of Two In-frame Initiation Codons", The Journal of Biological Chemistry, 2001, vol. 276, No. 23, Issue of Jun. 8, pp. 20474-20481.

NCBI, GenBank Accession No. WP_015177110. (May 19, 2013).
NCBI, GenBank Accession No. WP_009787090. (May 25, 2013).
NCBI, GenBank Accession No. WP_006634434. (Aug. 1, 2013).
NCBI, GenBank Accession No. AFZ07847.1. (Jul. 22, 2013).
NCBI, GenBank Accession No. WP_015224927.1. (May 19, 2013).
NCBI, GenBank Accession No. WP_006634434.1. (Aug. 1, 2013).

Patzoldt et al., "A codon deletion confers resistance to herbicides inhibiting protoporphyrinogen oxidase", PNAS, 2006, vol. 103, No. 33, pp. 12329-12334.

XP-002784244, AFZ07847; SV I; linear; genomic DNA; STD; PRO; 1461 BP., Project:PRJNA158711, https ://www.ebi.ac.uk/ena/data/view/ AFZ0784 7 &display=1.

Identification of a gene essential for protoporphyrinogen IX oxidase activity in the cyanobacterium *Synechocystis* sp. PCC6803, Kazushige Kato et al., PNAS | Sep. 21, 2010, | vol. 107 | No. 38 | 16649-16654.

The extended European search report, Application No. 15870320.7, dated Sep. 13, 2018.

Overexpression of Plastidic Protoporphyrinogen IX Oxidase Leads to Resistance to the Diphenyl-Ether Herbicide Acifluorfen 1, Inna Lermontova et al., Plant Physiology, Jan. 2000, vol. 122, pp. 75-83.

AFZ43049; SV 1; linear; genomic DNA; STD; PRO; 1401 BP., https://www.ebi.ac.uk/ena/data/view/AFZ43049&display=1.

The supplementary European search report, Application No. 15870320.7, dated May 14, 2018.

Sequence Search: UniProtKB/TrEMBL., http://www.uniprot.org/uniprot/AOYX99 .txt?version=1, Jan. 21, 2007, AOYX99.

Sequence Search: UniProtKB/TrEMBL., http://www.uniprot.org/uniprot/F5UKM3.txt?version-I, Jul. 27, 2011, F5UKM3.

Sequence Search: UniProtKB/TrEMBL., http://www.uniprot.org/uniprot/K9VK16.txt?version=1, Mar. 6, 2013, K9VK16.

Sequence Search: UniProtKB/TrEMBL., http://www.uniprot.org/uniprot/K9Y873.txt?version=1, Mar. 6, 2013, K9Y873.

Nucleotide Sequence N Access EBI: AFZ43049.1, protoporphyrinogen oxidase [*Halothece* sp. PCC 7418], US DOE Joint Genome Institute, Jul. 17, 2013.

Su Shao-quan, "The Development of Protoporphyrinogen Oxidase Inhibiting Herbicides", Agrochemicals Research & Application, 2011, vol. 15 No. 1.

Joonseon Yoon et al., "Characterization of HemY-type protoporphyrinogen IX oxidase genes from cyanobacteria and their functioning in transgenic Arabidopsis", Plant Molecular Biology, 2019, pp. 561-574, vol. 101.

* cited by examiner

SEQUENCE LISTING

```
<160> NUMBER OF SEQ ID NOS: 34

<210> SEQ ID NO 1
<211> LENGTH: 486
<212> TYPE: PRT
<213> ORGANISM: Oscillatoria nigroviridis PCC 7112
<220> FEATURE:
<221> NAME/KEY: PEPTIDE
<222> LOCATION: (1)..(486)
<223> OTHER INFORMATION: CyPPo2

<400> SEQUENCE: 1

Met Glu Leu Leu Asp Thr Leu Ile Val Gly Ala Gly Ile Ser Gly Leu
1               5                   10                  15

Ser Leu Ala His Ala Leu His Lys Glu Ala Thr Ser Ala Ser Pro Leu
```

```
            20                  25                  30
Lys Ile Leu Val Ala Glu Ser Gln Gly Arg Val Gly Gly Asn Ile Thr
            35                  40                  45
Thr Val Thr Ala Glu Gly Phe Leu Trp Glu Gly Pro Asn Ser Phe
        50                  55                  60
Ser Pro Thr Pro Glu Leu Met Lys Leu Ala Val Asp Val Gly Leu Lys
65                  70                  75                  80
Gln Glu Leu Ile Phe Ala Asp Arg Lys Leu Pro Arg Phe Val Tyr Trp
                85                  90                  95
Glu Asn Lys Leu Gln Pro Val Pro Met Thr Pro Ala Met Ile Gln
            100                 105                 110
Ser Gln Leu Leu Ser Phe Pro Gly Lys Leu Arg Ala Leu Phe Gly Ala
            115                 120                 125
Leu Gly Phe Val Ala Pro Ala Met Gly Asp Arg Leu Ser Gln Gln Gly
            130                 135                 140
Asn Glu Glu Thr Val Ser Gln Phe Phe Arg Arg His Leu Gly Thr Glu
145                 150                 155                 160
Val Met Gln Arg Leu Val Glu Pro Phe Val Ser Gly Val Tyr Ala Gly
                165                 170                 175
Asp Pro Gln Gln Leu Ser Ala Ala Ala Phe Gly Arg Val Ala Lys
            180                 185                 190
Met Ala Asp Val Gly Gly Gly Leu Val Ala Gly Ala Leu Leu Ser Ala
            195                 200                 205
Lys Asn Arg Pro Lys Lys Met Pro Ala Asp Pro Asn Val Pro Lys Thr
            210                 215                 220
Lys Pro Gly Glu Leu Gly Ser Phe Lys Gln Gly Leu Lys Ala Leu Pro
225                 230                 235                 240
Glu Ala Ile Ala Ala Lys Leu Gly Asp Arg Val Lys Leu Asn Trp His
                245                 250                 255
Leu Thr Arg Leu Gln Arg Thr Glu Arg Glu Thr Tyr Ile Ala Glu Phe
            260                 265                 270
Ser Thr Pro Asp Gly Gln Gln Glu Val Glu Ala Arg Thr Val Val Leu
            275                 280                 285
Thr Thr Pro Ala Tyr Val Thr Ala Asp Leu Leu Gln Pro Leu Glu Pro
            290                 295                 300
Gln Val Ser Ser Ala Leu Gln Ala Phe Thr Tyr Pro Thr Val Ala Ser
305                 310                 315                 320
Val Val Leu Ala Tyr Pro Gln Ser Asp Val Lys Gly Lys Leu Val Gly
                325                 330                 335
Phe Gly Asn Leu Ile Pro Arg Gly Gln Gly Ile Arg Cys Leu Gly Thr
            340                 345                 350
Ile Trp Thr Ser Ser Leu Phe Pro Asp Arg Ala Pro Ala Gly Trp Gln
            355                 360                 365
Thr Leu Thr Ser Tyr Ile Gly Gly Ala Thr Asp Ser Glu Ile Gly Asn
            370                 375                 380
Leu Asp Ser Glu Gln Ile Val Arg Glu Val His Arg Asp Leu Ser Arg
385                 390                 395                 400
Ile Leu Leu Lys Pro Asp Val Pro Gln Pro Lys Val Leu Thr Val Lys
                405                 410                 415
Leu Trp Lys Arg Ala Ile Pro Gln Tyr Asn Leu Gly His Phe Asp Arg
            420                 425                 430
Leu Gln Gln Ile Asp Glu Gly Leu Lys Ser Leu Pro Gly Val Tyr Leu
            435                 440                 445
```

```
Cys Ser Asn Tyr Val Gly Gly Val Ala Leu Gly Asp Cys Val Arg Arg
    450                 455                 460

Gly Phe Asp Arg Ala Arg Glu Val Gly Glu Tyr Leu Gln Lys Lys Gln
465                 470                 475                 480

Ser Asp Thr Arg Ser Ile
            485

<210> SEQ ID NO 2
<211> LENGTH: 1461
<212> TYPE: DNA
<213> ORGANISM: Oscillatoria nigroviridis PCC 7112
<220> FEATURE:
<221> NAME/KEY: DNA
<222> LOCATION: (1)..(1461)
<223> OTHER INFORMATION: CyPPO2

<400> SEQUENCE: 2
atggaactat tagatacctt gattgtgggt gcgggtatta gcggtttgag tttggcgcac      60
gcacttcaca aggaagcaac gagtgcatcg ccgctgaaga ttttagtcgc tgagagtcag     120
ggacgtgtgg gcgggaacat cacgactgtg acagcagagg gtttctctg gaggagggc      180 ccgaacagtt tttcgccgac gccggaattg atgaagttgg ctgtggatgt gggattgaag     240
caggagttga ttttgccga tcgcaaattg cctcgttttg tgtattggga aaataagctg      300
caaccggtgc cgatgactcc accggcgatg attcagtctc agttgctgag ttttccgggg     360
aaactgcggg cgttgttcgg ggctttgggg tttgtcgcgc cggcaatggg cgatcgactt     420
tcgcagcagg gtaacgagga aacagtttct caattttttcc gccgtcatct cggtacggaa     480
gtgatgcagc ggttggtgga accttttgtt tctggggttt atgccggcga tccgcaacaa     540
cttagcgcgg cggcggcttt tggccgggta gccaagatgg ctgatgtggg tggcgggctg     600
gtggcggggg cgctgctttc tgctaaaaac agaccgaaga aaatgcctgc agacccgaat     660
gttcctaaaa ctaagccggg ggagttgggt tcgttcaagc aggggttgaa ggcttttgcca     720 gaggcgatcg ctgctaagtt gggcgatcga gtgaaactca actggcactt gactcgcctc     780
cagcgcacag aacgcgaaac ttacattgct gaattctcga cgcccgacgg acagcaggaa     840
gttgaggcgc gcaccgtggt tttgacaacg cccgcttacg ttacagccga tttgttgcaa     900
cctctggaac cgcaagttag cagcgcttta caagctttta cttatcctac ggttgcctcc     960
gttgtcttag cataccccgca gtcggatgtc aagggtaaat tagtgggttt tggaaaattta    1020 attccgaggg ggcagggaat cgctgtctc gggacgattt ggacatcgag tttatttccc     1080
gatcgcgcgc ctgcagggtg gcaaactctc accagttaca tcggcggggc aacagactcg     1140
gaaattggca atctcgactc agaacaaatc gttcggagg tacaccgaga tttgtctcgg     1200
attttgctga aaccagatgt gccacagcca aaagttttaa cggtgaagct gtggaaacgg     1260
gcgattcctc agtacaattt ggggcatttc gatcgcctgc aacaaatcga tgagggctta    1320
aaatctttgc ctggagtgta tttgtgcagc aactacgttg gcggagtggc tttgggagat    1380
tgcgtgcgaa ggggtttcga tcgtgcgcga gaagtgggcg agtatttgca agaaacaa      1440 tcagatactc gatcgatctg a                                               1461

<210> SEQ ID NO 3
<211> LENGTH: 479
<212> TYPE: PRT
<213> ORGANISM: Lyngbya sp. PCC 8106
<220> FEATURE:
<221> NAME/KEY: PEPTIDE
```

<222> LOCATION: (1)..(479)
<223> OTHER INFORMATION: CyPPO4

<400> SEQUENCE: 3

```
Met Thr His Val Leu Asp Ser Leu Ile Val Gly Ala Gly Ile Ser Gly
1               5                   10                  15

Leu Ala Leu Ala His Ala Leu His Gln Asn Gln Asp His Gln Leu Pro
            20                  25                  30

Leu Asn Ile Leu Val Ser Glu His Gln Gly Arg Val Gly Gly Asn Ile
        35                  40                  45

Thr Thr Val Ser Glu Gly Glu Phe Leu Trp Glu Gly Pro Asn Ser
    50                  55                  60

Phe Ser Pro Thr Pro Glu Leu Leu Lys Leu Ala Val Glu Val Gly Leu
65                  70                  75                  80

Lys Pro Glu Leu Val Phe Ala Asp Arg Lys Leu Pro Arg Tyr Val Tyr
                85                  90                  95

Trp Asn Gly Gln Leu Met Pro Val Pro Met Ser Pro Pro Ala Leu Leu
            100                 105                 110

Ser Thr Lys Leu Leu Ser Pro Gly Gly Lys Leu Arg Ala Leu Thr Gly
        115                 120                 125

Ala Leu Gly Phe Val Gln Pro Ala Met Gly Glu Ser Leu Ser Gln Gln
    130                 135                 140

Asn Gly Glu Glu Thr Ile Ser Gln Phe Phe Glu Arg His Leu Gly Ser
145                 150                 155                 160

Glu Val Leu Lys Arg Leu Val Glu Pro Phe Val Ser Gly Val Tyr Ala
                165                 170                 175

Gly Asp Pro Gln Gln Leu Glu Ile Ser Ser Ala Phe Ala Arg Val Ala
            180                 185                 190

Arg Met Ala Tyr Ser Gly Gly Leu Val Ala Gly Ala Val Leu Ser
        195                 200                 205

Arg Arg Gln Asn Lys Ser Pro Arg Ser Pro Ala Asp Pro Ser Ile Pro
    210                 215                 220

Gln Thr Lys Arg Gly Glu Leu Gly Ser Phe Arg Gln Gly Ile Gly Ala
225                 230                 235                 240

Leu Pro Asn Ala Ile Ala Lys Gln Leu Gly Asp Gln Leu Lys Leu Asn
                245                 250                 255

Trp Gln Leu Thr Arg Leu Glu Arg Thr Glu Asn Gln Thr Tyr Arg Ala
            260                 265                 270

Glu Phe Ser Thr Pro Glu Gly Val Gln Gln Val Glu Thr Arg Thr Val
        275                 280                 285

Val Leu Thr Thr Pro Ala Tyr Val Thr Ala Glu Ile Leu Lys Pro Leu
    290                 295                 300

Gln Leu Gln Val Ser Gln Thr Leu Thr Glu Ile Pro Tyr Pro Val
305                 310                 315                 320

Ala Cys Val Val Leu Ala Tyr Pro Val Ser Ala Leu Lys Gln Lys Leu
                325                 330                 335

Thr Gly Phe Gly Asn Leu Val Pro Arg Gly Gln Gly Ile Arg Thr Leu
            340                 345                 350

Gly Thr Ile Trp Thr Ser Ser Leu Phe Pro Gly Arg Ala Pro Gln Gly
        355                 360                 365

Trp Gln Val Leu Thr Ser Tyr Ile Gly Gly Ala Thr Asp Pro Glu Ile
    370                 375                 380

Gly Glu Leu Glu Asp Asp Gln Ile Val Glu Ala Val His Gln Asp Leu
385                 390                 395                 400
```

Arg His Ile Leu Leu Lys Glu Asp Ile Ser Pro Lys Val Leu Ala Val
              405                 410                 415

His Leu Trp Lys Arg Ala Ile Pro Gln Tyr Asn Leu Gly His Gln Gln
          420                 425                 430

Arg Leu Gln His Val Asn Glu Gly Leu Glu Ala Met Pro Gly Leu Tyr
          435                 440                 445

Leu Cys Ser Asn Tyr Ile Asp Gly Val Ala Leu Gly Asp Cys Val Arg
      450                 455                 460

Arg Ser Ile Gly Gln Ala Asn Glu Ile Leu Ser Phe Leu Gly Gln
465                 470                 475

<210> SEQ ID NO 4
<211> LENGTH: 1440
<212> TYPE: DNA
<213> ORGANISM: Lyngbya sp. PCC 8106
<220> FEATURE:
<221> NAME/KEY: DNA
<222> LOCATION: (1)..(1440)
<223> OTHER INFORMATION: CyPPO4

<400> SEQUENCE: 4

| | |
|---|---|
| atgactcacg tactcgatag tttaatcgtc ggtgcaggca ttagcggcct ggcgttagct | 60 |
| catgctctcc atcagaacca agatcatcaa ttgcctctca acattcttgt cagcgagcat | 120 |
| caaggacggg taggaggaaa tataaccaca gtatccgaag agaatttct ttgggaagaa | 180 |
| ggccccaata gtttttctcc aacccctgag ttactgaagt tagcggtaga agtaggtctt | 240 |
| aagcctgagc tagtctttgc cgatcgcaag ttacctcggt acgtttactg gaatggtcaa | 300 |
| ctcatgcctg tgccgatgag tcctccggct tgttgagta caaaactctt aagtcctgga | 360 |
| ggtaaacttc gagcattaac gggggcattg gggtttgtac aacccgcgat gggagaatcg | 420 |
| ttaagtcaac aaaatgggga gaaacgatc tcgcagtttt tgagcgtca tttgggttca | 480 |
| gaagttctca gcgactggt tgaaccctt gtttctggtg tttatgcagg cgatccccag | 540 |
| caactcgaaa ttagctcggc ttttgcccga gtcgcacgta tggcttacag tggcggtgga | 600 |
| ttggttgctg gagcggtttt atcgcgtcgt cagaacaaat ctccgcgatc gcctgccgac | 660 |
| ccgtctattc cccaaactaa acggggagag ttggggtctt ttcgtcaggg gattggagcc | 720 |
| ttacccaatg cgatcgccaa acagttaggc gatcaactca aattaaactg gcaactcacc | 780 |
| cgtctcgaac ggactgaaaa ccaaacctat cgggctgaat tttcgactcc agaaggggtt | 840 |
| caacaggtag aaactcgaac ggtggtgttg acgactccgg cctatgtcac agcagaaatt | 900 |
| ctcaaaccgt tgcaactcca gtcagtcaa acgttaactg aaattcccta tccccggtg | 960 |
| gcttgcgtcg ttttagccta tcccgtttca gctttaaagc agaaattaac cggatttggc | 1020 |
| aatttagttc cccgaggaca agggattcgg acgttaggca cgatttggac atcgagttta | 1080 |
| tttcctggtc gcgcccccca aggctggcaa gtcctcacca gttatattgg cggagcgacg | 1140 |
| gatccagaaa ttggagagtt agaagatgat caaattgttg aggcggttca tcaagatttg | 1200 |
| cgtcacattt tactcaaaga agatatctct cccaaagtgc tagccgtgca tctgtggaaa | 1260 |
| cgtgctatcc ctcaatacaa tctcggacac aacaacggt tacaacacgt taatgagggt | 1320 |
| ctagaggcaa tgccggggtt atatctgtgt agcaactata tcgacggtgt agcgttggga | 1380 |
| gattgtgtgc gtcgttctat cggacaagct aacgaaattc tcagttttt gggtcaatag | 1440 |

<210> SEQ ID NO 5
<211> LENGTH: 466

```
<212> TYPE: PRT
<213> ORGANISM: Halothece sp. PCC 7418
<220> FEATURE:
<221> NAME/KEY: PEPTIDE
<222> LOCATION: (1)..(466)
<223> OTHER INFORMATION: CyPPO8

<400> SEQUENCE: 5
```

| | | | | | | | | | | | | | | |
|---|---|---|---|---|---|---|---|---|---|---|---|---|---|---|
| Met | Ile | Asp | Thr | Leu | Ile | Val | Gly | Ala | Gly | Ile | Ser | Gly | Leu | Ser | Ala |
| 1 | | | | 5 | | | | | 10 | | | | | 15 | |
| Ala | Tyr | Arg | Leu | Asp | Glu | Lys | Gln | Arg | Gln | Val | Leu | Val | Ala | Glu | Lys |
| | | | 20 | | | | | 25 | | | | | 30 | | |
| Arg | Asp | Arg | Ala | Gly | Gly | Asn | Ile | Thr | Ser | Gln | Gln | Ser | Gly | Asp | Phe |
| | | 35 | | | | | 40 | | | | | 45 | | | |
| Leu | Trp | Glu | Glu | Gly | Pro | Asn | Ser | Phe | Ser | Pro | Thr | Pro | Glu | Leu | Leu |
| | 50 | | | | | 55 | | | | | 60 | | | | |
| Lys | Leu | Ala | Val | Asp | Ala | Gly | Leu | Arg | Asn | Glu | Leu | Ile | Phe | Ala | Asp |
| 65 | | | | | 70 | | | | | 75 | | | | | 80 |
| Arg | Gly | Leu | Pro | Arg | Tyr | Val | Tyr | Trp | Glu | Gly | Lys | Leu | Arg | Pro | Val |
| | | | | 85 | | | | | 90 | | | | | 95 | |
| Pro | Met | Ser | Pro | Pro | Thr | Ala | Val | Thr | Ser | Gln | Leu | Leu | Ser | Pro | Ile |
| | | | 100 | | | | | 105 | | | | | 110 | | |
| Gly | Lys | Leu | Arg | Ala | Leu | Thr | Gly | Ala | Leu | Gly | Phe | Ile | Pro | Pro | Gln |
| | | 115 | | | | | 120 | | | | | 125 | | | |
| Val | Ser | Ser | Gln | Glu | Glu | Thr | Val | Ala | Asp | Phe | Phe | Thr | Arg | His | Leu |
| | 130 | | | | | 135 | | | | | 140 | | | | |
| Gly | Ser | Glu | Val | Ala | Gln | Arg | Leu | Val | Ser | Pro | Phe | Val | Ser | Gly | Val |
| 145 | | | | | 150 | | | | | 155 | | | | | 160 |
| Tyr | Ala | Gly | Asp | Val | Asp | Gln | Leu | Ser | Ala | Glu | Ala | Ala | Phe | Gly | Arg |
| | | | | 165 | | | | | 170 | | | | | 175 | |
| Val | Thr | Gln | Leu | Ala | Asp | Val | Gly | Gly | Gly | Leu | Val | Ala | Gly | Ala | Ile |
| | | | 180 | | | | | 185 | | | | | 190 | | |
| Leu | Cys | Arg | Arg | Gln | Lys | Pro | Lys | Ser | Thr | Pro | Lys | Thr | Ala | Lys | Pro |
| | | 195 | | | | | 200 | | | | | 205 | | | |
| Ser | Asp | Ile | Pro | Glu | Thr | Lys | Ser | Gly | Gln | Leu | Gly | Ser | Phe | Lys | Glu |
| | 210 | | | | | 215 | | | | | 220 | | | | |
| Gly | Leu | Gln | Gln | Leu | Pro | Ser | Ala | Ile | Val | Ser | Gln | Leu | Gly | Asp | Lys |
| 225 | | | | | 230 | | | | | 235 | | | | | 240 |
| Val | Lys | Phe | Gln | Trp | Glu | Leu | Lys | Asn | Ile | Ser | Pro | His | Pro | Glu | Ser |
| | | | | 245 | | | | | 250 | | | | | 255 | |
| Gly | Tyr | Val | Ala | Thr | Phe | Ser | Thr | Pro | Glu | Gly | Glu | Gln | Thr | Val | Glu |
| | | | 260 | | | | | 265 | | | | | 270 | | |
| Ala | Lys | Thr | Val | Ile | Leu | Thr | Thr | Pro | Ala | Tyr | Val | Thr | Ala | Ser | Leu |
| | | 275 | | | | | 280 | | | | | 285 | | | |
| Val | Lys | Asp | Leu | Ser | Pro | Gln | Ala | Ser | Gln | Ala | Leu | Asn | Glu | Ile | Ser |
| | 290 | | | | | 295 | | | | | 300 | | | | |
| Tyr | Pro | Pro | Val | Ala | Cys | Val | Val | Leu | Ala | Tyr | Pro | Asp | Glu | Ala | Leu |
| 305 | | | | | 310 | | | | | 315 | | | | | 320 |
| Arg | Phe | Pro | Leu | Lys | Gly | Phe | Gly | Asn | Leu | Asn | Pro | Arg | Ser | Gln | Gly |
| | | | | 325 | | | | | 330 | | | | | 335 | |
| Ile | Arg | Thr | Leu | Gly | Thr | Ile | Trp | Ser | Ser | Thr | Leu | Phe | Pro | Gly | Arg |
| | | | 340 | | | | | 345 | | | | | 350 | | |
| Thr | Pro | Lys | Gly | Trp | His | Leu | Leu | Thr | Asn | Phe | Ile | Gly | Gly | Ala | Thr |
| | | 355 | | | | | 360 | | | | | 365 | | | |
| Asp | Pro | Ala | Ile | Ala | Glu | Leu | Ser | Glu | Asp | Gln | Ile | Ile | Glu | Gln | Val |

```
                370               375               380
His Gln Asp Leu Gln Gln Ala Val Ile Lys Ser Gly Ser Ile Pro Lys
385                 390                 395                 400

Pro Leu Ala Val His Leu Trp Ser Lys Ala Ile Pro Gln Tyr Asn Leu
                405                 410                 415

Gly His Leu Lys Arg Leu Glu Thr Ile Arg Asn His Leu Lys Pro Phe
            420                 425                 430

Ser Gly Leu Phe Leu Ser Ser Asn Tyr Leu Asp Gly Val Ala Leu Gly
        435                 440                 445

Asp Cys Val Arg Arg Gly Glu Glu Ser Ser Gln Ala Val Leu Asp Tyr
    450                 455                 460

Leu Gly
465

<210> SEQ ID NO 6
<211> LENGTH: 1401
<212> TYPE: DNA
<213> ORGANISM: Halothece sp. PCC 7418
<220> FEATURE:
<221> NAME/KEY: gene
<222> LOCATION: (1)..(1401)
<223> OTHER INFORMATION: CyPPO8

<400> SEQUENCE: 6
atgatagata ctttaattgt gggagcaggg attagtggtt taagtgctgc gtatcgactc      60
gatgagaagc agcgccaagt gctggttgca gaaaagcgcg atcgcgctgg gggaaatatc     120
accagccaac aaagtggcga tttcctctgg aagaaggac cgaacagttt ttctcccaca      180
ccagaactcc taaaactagc ggttgatgcg ggcttaagaa atgagttaat ctttgctgat     240
cgcggacttc cccgttatgt ttattgggag gggaaactgc gccctgttcc tatgagtccc     300
cccacagccg tgacatccca gttgctgagt ccaatcggga actacgggc gttaacgggt     360 gcattaggct ttattccccc gcaagtgtcg agtcaggaag aaacggttgc ggactttttt     420
acccgtcatc tcggttcaga agtagcccaa cggttagtga gtccgtttgt gtctggggtt     480
tatgcagggg atgtggatca actcagtgcg gaagctgcat ttggacgagt tacccaactg     540
gcggatgtgg gcggtggact ggtcgcaggt gcgatttat gtcgtcgtca aaagccaaag      600
tcaaccccaa aaacggctaa accgtctgat attccagaaa caaagtctgg acagttaggt     660
tcatttaagg aaggattaca acaattaccc agcgcgatcg tttctcaact gggagacaaa     720
gtaaagtttc aatgggaact gaaaaatatc tcccctcatc cagaatcggg ttacgtcgcg     780 acatttcca caccagaggg agaacaaaca gtcgaagcca aaccgttat cctcaccact      840 cccgcctacg ttaccgcctc tctggtcaaa gatttatcac ctcaagccag tcaagcctta     900
aacgaaattt cctatccccc cgtagcttgt gtggtcttag cctatcccga tgaagccctc     960
cgttttcccc tcaaaggatt tggtaatctt aaccctcgca gtcaaggaat ccgcactctt    1020
ggtacaattt ggagttcaac actctttcca ggacgcacgc cgaaaggttg catctctta    1080 accaatttta ttggcggtgc aactgatccc gcaattgctg aactcagtga agatcaaatt    1140
attgaacaag tccatcaaga cttacaacaa gcggtgatta atcgggaag tatcccgaaa    1200 cccttagccg ttcatttgtg gtcaaaagcg attccgcaat acaatctcgg acatctgaaa    1260
cggttagaaa ccatccgcaa tcacttaaaa cccttctctg gactcttttt atcgagtaac    1320
tatctcgatg gcgttgcgtt gggtgattgt gtgcgccgag gggaagagag tagtcaagcc    1380
gtgttagatt atttgggtta a                                              1401
```

<210> SEQ ID NO 7
<211> LENGTH: 486
<212> TYPE: PRT
<213> ORGANISM: Microcoleus vaginatus
<220> FEATURE:
<221> NAME/KEY: PEPTIDE
<222> LOCATION: (1)..(486)
<223> OTHER INFORMATION: CyPPO12

<400> SEQUENCE: 7

| Met | Glu | Leu | Leu | Asp | Thr | Leu | Ile | Val | Gly | Ala | Gly | Ile | Ser | Gly | Leu |
|---|---|---|---|---|---|---|---|---|---|---|---|---|---|---|---|
| 1 | | | | 5 | | | | | 10 | | | | | 15 | |

| Ser | Leu | Ala | His | Ala | Leu | His | Lys | Glu | Ala | Thr | Ser | Pro | Ser | Ser | Leu |
|---|---|---|---|---|---|---|---|---|---|---|---|---|---|---|---|
| | | | 20 | | | | | 25 | | | | | 30 | | |

| Lys | Ile | Leu | Val | Ala | Glu | Ser | Gln | Gly | Arg | Val | Gly | Gly | Asn | Ile | Thr |
|---|---|---|---|---|---|---|---|---|---|---|---|---|---|---|---|
| | | 35 | | | | | 40 | | | | | 45 | | | |

| Thr | Val | Thr | Ala | Glu | Gly | Phe | Leu | Trp | Glu | Glu | Gly | Pro | Asn | Ser | Phe |
|---|---|---|---|---|---|---|---|---|---|---|---|---|---|---|---|
| | 50 | | | | | 55 | | | | | 60 | | | | |

| Ser | Pro | Thr | Pro | Glu | Leu | Met | Lys | Leu | Ala | Val | Asp | Val | Gly | Leu | Lys |
|---|---|---|---|---|---|---|---|---|---|---|---|---|---|---|---|
| 65 | | | | | 70 | | | | | 75 | | | | | 80 |

| Gln | Glu | Leu | Ile | Phe | Ala | Asp | Arg | Lys | Leu | Pro | Arg | Phe | Val | Tyr | Trp |
|---|---|---|---|---|---|---|---|---|---|---|---|---|---|---|---|
| | | | | 85 | | | | | 90 | | | | | 95 | |

| Gln | Asn | Lys | Leu | Gln | Pro | Val | Pro | Met | Thr | Pro | Pro | Ala | Met | Ile | Gln |
|---|---|---|---|---|---|---|---|---|---|---|---|---|---|---|---|
| | | | 100 | | | | | 105 | | | | | 110 | | |

| Ser | Gln | Leu | Leu | Ser | Phe | Pro | Gly | Lys | Leu | Arg | Ala | Leu | Phe | Gly | Ala |
|---|---|---|---|---|---|---|---|---|---|---|---|---|---|---|---|
| | | 115 | | | | | 120 | | | | | 125 | | | |

| Leu | Gly | Phe | Val | Ala | Pro | Ala | Ile | Gly | Ser | Gly | Leu | Ser | Gln | Gln | Gly |
|---|---|---|---|---|---|---|---|---|---|---|---|---|---|---|---|
| | 130 | | | | | 135 | | | | | 140 | | | | |

| Asp | Glu | Glu | Thr | Val | Ser | Gln | Phe | Phe | Arg | Arg | His | Leu | Gly | Thr | Glu |
|---|---|---|---|---|---|---|---|---|---|---|---|---|---|---|---|
| 145 | | | | | 150 | | | | | 155 | | | | | 160 |

| Val | Met | Gln | Arg | Leu | Val | Glu | Pro | Phe | Val | Ser | Gly | Val | Tyr | Ala | Gly |
|---|---|---|---|---|---|---|---|---|---|---|---|---|---|---|---|
| | | | | 165 | | | | | 170 | | | | | 175 | |

| Asp | Pro | Gln | Gln | Leu | Ser | Ala | Ala | Ala | Ala | Phe | Gly | Arg | Val | Thr | Lys |
|---|---|---|---|---|---|---|---|---|---|---|---|---|---|---|---|
| | | | 180 | | | | | 185 | | | | | 190 | | |

| Met | Ala | Asp | Val | Gly | Gly | Gly | Leu | Met | Ala | Gly | Ala | Leu | Leu | Ser | Ala |
|---|---|---|---|---|---|---|---|---|---|---|---|---|---|---|---|
| | | 195 | | | | | 200 | | | | | 205 | | | |

| Arg | Lys | Arg | Pro | Lys | Gln | Met | Pro | Ala | Asp | Pro | Asn | Val | Pro | Ser | Thr |
|---|---|---|---|---|---|---|---|---|---|---|---|---|---|---|---|
| | 210 | | | | | 215 | | | | | 220 | | | | |

| Arg | Pro | Gly | Glu | Leu | Gly | Ser | Phe | Lys | Gln | Gly | Leu | Lys | Ala | Leu | Pro |
|---|---|---|---|---|---|---|---|---|---|---|---|---|---|---|---|
| 225 | | | | | 230 | | | | | 235 | | | | | 240 |

| Glu | Ala | Ile | Ala | Ala | Gln | Leu | Gly | Asp | Arg | Val | Lys | Val | Asn | Trp | His |
|---|---|---|---|---|---|---|---|---|---|---|---|---|---|---|---|
| | | | | 245 | | | | | 250 | | | | | 255 | |

| Leu | Thr | Arg | Leu | Gln | Arg | Thr | Glu | Arg | Glu | Thr | Tyr | Ile | Ala | Val | Phe |
|---|---|---|---|---|---|---|---|---|---|---|---|---|---|---|---|
| | | | 260 | | | | | 265 | | | | | 270 | | |

| Ser | Thr | Pro | Asp | Gly | Gln | Gln | Glu | Val | Glu | Ala | Arg | Thr | Val | Val | Leu |
|---|---|---|---|---|---|---|---|---|---|---|---|---|---|---|---|
| | | 275 | | | | | 280 | | | | | 285 | | | |

| Thr | Thr | Pro | Ala | Tyr | Ile | Thr | Ala | Glu | Leu | Leu | Gln | Pro | Leu | Gln | Pro |
|---|---|---|---|---|---|---|---|---|---|---|---|---|---|---|---|
| | 290 | | | | | 295 | | | | | 300 | | | | |

| Lys | Val | Ser | Ser | Ala | Leu | Gln | Ala | Phe | Thr | Tyr | Pro | Thr | Val | Ala | Cys |
|---|---|---|---|---|---|---|---|---|---|---|---|---|---|---|---|
| 305 | | | | | 310 | | | | | 315 | | | | | 320 |

| Val | Val | Leu | Ala | Tyr | Pro | Gln | Ser | Asp | Val | Lys | Asp | Lys | Leu | Val | Gly |
|---|---|---|---|---|---|---|---|---|---|---|---|---|---|---|---|
| | | | | 325 | | | | | 330 | | | | | 335 | |

| Phe | Gly | Asn | Leu | Ile | Pro | Arg | Gly | Gln | Gly | Ile | Arg | Thr | Leu | Gly | Thr |
|---|---|---|---|---|---|---|---|---|---|---|---|---|---|---|---|
| | | | 340 | | | | | 345 | | | | | 350 | | |

```
Ile Trp Thr Ser Ser Leu Phe Ala Asp Arg Ala Pro Ala Gly Trp Gln
            355                 360                 365

Thr Leu Ser Ser Tyr Ile Gly Gly Ala Thr Ser Glu Ile Gly Asn
    370                 375                 380

Leu Asp Ser Glu Gln Ile Val Arg Glu Val His Arg Asp Leu Ser Arg
385                 390                 395                 400

Ile Leu Leu Lys Pro Asp Val Pro Gln Pro Lys Val Leu Ala Val Asn
                405                 410                 415

Val Trp Lys Arg Ala Ile Pro Gln Tyr Asn Leu Gly His Phe Asp Arg
            420                 425                 430

Leu Gln Gln Ile Asp Glu Gly Leu Lys Ser Leu Pro Gly Val Tyr Leu
        435                 440                 445

Cys Ser Asn Tyr Val Gly Gly Val Ala Leu Gly Asp Cys Val Arg Arg
    450                 455                 460

Gly Phe Glu Arg Ala Arg Glu Val Gly Glu Tyr Leu Gln Asn Lys Gln
465                 470                 475                 480

Ser Asp Thr Arg Ser Ile
                485

<210> SEQ ID NO 8
<211> LENGTH: 1461
<212> TYPE: DNA
<213> ORGANISM: Microcoleus vaginatus
<220> FEATURE:
<221> NAME/KEY: DNA
<222> LOCATION: (1)..(1461)
<223> OTHER INFORMATION: CyPPO12

<400> SEQUENCE: 8
atggaactct tggatactct cattgttgga gcaggtattt caggactttc tctcgcacac      60
gctttacata aggaggctac ttcaccatct tcacttaaga ttttggttgc tgaatctcaa     120
ggtagagtgg gaggtaatat cactacagtt accgctgagg ttttctttg gaagagggga     180 cctaacagtt tctctcctac tccagaactc atgaagttag ctgttgatgt gggacttaaa     240
caggagttga tttttgcaga tagaaaactt ccaagattcg tgtattggca aaacaaactt     300
caacctgttc caatgacacc tccagctatg atccaatctc agcttctttc ttttcctgga     360
aaacttagag ctttgtttgg tgcacttgga ttcgttgctc cagcaatagg ttcaggattg     420
agtcaacagg gagatgaaga gactgtttct caattttca gaaggcatct cggaacagaa     480
gttatgcaga gattagtgga gccatttgtt agtggtgtgt acgctggaga tcctcaacag     540
ctttctgctg ctgctgcttt cggtagggtt acaaaaatgg ctgatgtggg aggtggattg     600
atggctggag cactcttatc tgctagaaag aggccaaaac aaatgcctgc tgatcctaat     660
gttccttcaa ctagacctgg tgaattggga agttttaagc aaggtctcaa ggctcttcca     720
gaggcaatag ctgcacagct cggagataga gttaaggtga actggcacct tacaagattg     780
caaaggactg aaagagagac atatattgct gtgttctcta ctcctgatgg acaacaggaa     840
gttgaggcaa gaacagttgt gcttaccact ccagcttaca tcaccgcaga acttttgcaa     900
ccacttcagc ctaaagttag ttctgctttg caagcattca catatccaac cgttgcttgt     960
gttgtgttgg cataccctca gtcagatgtt aaggataaac tcgtgggttt tggaaatctt    1020
attcctagag gtcaaggaat caggactctc ggtacaatat ggacctcaag tttattcgct    1080
gatagagcac ctgctggatg gcaaaccctt tcttcatata ttggtggagc tactgatagt    1140
gagatcggta acctcgattc tgaacagata gttagggagg tgcatagaga tttgtcaaga    1200
```

```
attttgctca agcctgatgt tcctcaacca aaagtgttgg ctgttaatgt gtggaagaga    1260
gcaataccac agtacaacct tggacacttt gataggttgc aacagattga tgaaggtctc    1320
aaatctttac ctggagttta tctctgttca aactacgttg gtggagtggc tttaggagat    1380
tgcgttagaa ggggattcga gagggcaaga gaggttggag aatacttaca aacaaacaa     1440 tctgatacca ggtcaatctg a                                              1461
```

<210> SEQ ID NO 9
<211> LENGTH: 537
<212> TYPE: PRT
<213> ORGANISM: Arabidopsis thaliana
<220> FEATURE:
<221> NAME/KEY: PEPTIDE
<222> LOCATION: (1)..(537)
<223> OTHER INFORMATION: Wild type AtPPO1

<400> SEQUENCE: 9

```
Met Glu Leu Ser Leu Leu Arg Pro Thr Thr Gln Ser Leu Leu Pro Ser
1               5                   10                  15

Phe Ser Lys Pro Asn Leu Arg Leu Asn Val Tyr Lys Pro Leu Arg Leu
            20                  25                  30

Arg Cys Ser Val Ala Gly Gly Pro Thr Val Gly Ser Ser Lys Ile Glu
        35                  40                  45

Gly Gly Gly Gly Thr Thr Ile Thr Thr Asp Cys Val Ile Val Gly Gly
    50                  55                  60

Gly Ile Ser Gly Leu Cys Ile Ala Gln Ala Leu Ala Thr Lys His Pro
65                  70                  75                  80

Asp Ala Ala Pro Asn Leu Ile Val Thr Glu Ala Lys Asp Arg Val Gly
                85                  90                  95

Gly Asn Ile Ile Thr Arg Glu Glu Asn Gly Phe Leu Trp Glu Glu Gly
            100                 105                 110

Pro Asn Ser Phe Gln Pro Ser Asp Pro Met Leu Thr Met Val Val Asp
        115                 120                 125

Ser Gly Leu Lys Asp Asp Leu Val Leu Gly Asp Pro Thr Ala Pro Arg
    130                 135                 140

Phe Val Leu Trp Asn Gly Lys Leu Arg Pro Val Pro Ser Lys Leu Thr
145                 150                 155                 160

Asp Leu Pro Phe Phe Asp Leu Met Ser Ile Gly Gly Lys Ile Arg Ala
                165                 170                 175

Gly Phe Gly Ala Leu Gly Ile Arg Pro Ser Pro Pro Gly Arg Glu Glu
            180                 185                 190

Ser Val Glu Glu Phe Val Arg Arg Asn Leu Gly Asp Glu Val Phe Glu
        195                 200                 205

Arg Leu Ile Glu Pro Phe Cys Ser Gly Val Tyr Ala Gly Asp Pro Ser
    210                 215                 220

Lys Leu Ser Met Lys Ala Ala Phe Gly Lys Val Trp Lys Leu Glu Gln
225                 230                 235                 240

Asn Gly Gly Ser Ile Ile Gly Gly Thr Phe Lys Ala Ile Gln Glu Arg
                245                 250                 255

Lys Asn Ala Pro Lys Ala Glu Arg Asp Pro Arg Leu Pro Lys Pro Gln
            260                 265                 270

Gly Gln Thr Val Gly Ser Phe Arg Lys Gly Leu Arg Met Leu Pro Glu
        275                 280                 285

Ala Ile Ser Ala Arg Leu Gly Ser Lys Val Lys Leu Ser Trp Lys Leu
    290                 295                 300
```

| | | | | | | | | | | | | | | |
|---|---|---|---|---|---|---|---|---|---|---|---|---|---|---|
|Ser|Gly|Ile|Thr|Lys|Leu|Glu|Ser|Gly|Gly|Tyr|Asn|Leu|Thr|Tyr|Glu
|305| | | |310| | | | |315| | | | |320

Thr Pro Asp Gly Leu Val Ser Val Gln Ser Lys Ser Val Val Met Thr
        325                 330                 335

Val Pro Ser His Val Ala Ser Gly Leu Leu Arg Pro Leu Ser Glu Ser
        340                 345                 350

Ala Ala Asn Ala Leu Ser Lys Leu Tyr Tyr Pro Pro Val Ala Ala Val
        355                 360                 365

Ser Ile Ser Tyr Pro Lys Glu Ala Ile Arg Thr Glu Cys Leu Ile Asp
        370                 375                 380

Gly Glu Leu Lys Gly Phe Gly Gln Leu His Pro Arg Thr Gln Gly Val
385                 390                 395                 400

Glu Thr Leu Gly Thr Ile Tyr Ser Ser Ser Leu Phe Pro Asn Arg Ala
        405                 410                 415

Pro Pro Gly Arg Ile Leu Leu Leu Asn Tyr Ile Gly Gly Ser Thr Asn
        420                 425                 430

Thr Gly Ile Leu Ser Lys Ser Glu Gly Glu Leu Val Glu Ala Val Asp
        435                 440                 445

Arg Asp Leu Arg Lys Met Leu Ile Lys Pro Asn Ser Thr Asp Pro Leu
450                 455                 460

Lys Leu Gly Val Arg Val Trp Pro Gln Ala Ile Pro Gln Phe Leu Val
465                 470                 475                 480

Gly His Phe Asp Ile Leu Asp Thr Ala Lys Ser Ser Leu Thr Ser Ser
        485                 490                 495

Gly Tyr Glu Gly Leu Phe Leu Gly Gly Asn Tyr Val Ala Gly Val Ala
        500                 505                 510

Leu Gly Arg Cys Val Glu Gly Ala Tyr Glu Thr Ala Ile Glu Val Asn
        515                 520                 525

Asn Phe Met Ser Arg Tyr Ala Tyr Lys
        530                 535

<210> SEQ ID NO 10
<211> LENGTH: 1614
<212> TYPE: DNA
<213> ORGANISM: Arabidopsis thaliana
<220> FEATURE:
<221> NAME/KEY: DNA
<222> LOCATION: (1)..(1614)
<223> OTHER INFORMATION: Wild type AtPPO1

<400> SEQUENCE: 10

```
atggagttat ctcttctccg tccgacgact caatcgcttc ttccgtcgtt ttcgaagccc      60
aatctccgat taaatgttta taagcctctt agactccgtt gttcagtggc cggtggacca     120
accgtcggat cttcaaaaat cgaaggcgga ggaggcacca ccatcacgac ggattgtgtg     180
attgtcggcg gaggtattag tggtctttgc atcgctcagg cgcttgctac taagcatcct     240
gatgctgctc cgaatttaat tgtgaccgag gctaaggatc gtgttggagg caacattatc     300
actcgtgaag agaatggttt tctctgggaa gaaggtccca atagtttca accgtctgat      360 cctatgctca ctatggtggt agatagtggt tgaaggatg atttggtgtt gggagatcct      420
actgcgccaa ggtttgtgtt gtggaatggg aaattgaggc cggttccatc gaagctaaca     480
gacttaccgt tctttgattt gatgagtatt ggtgggaaga ttagagctgg ttttggtgca     540
cttggcattc gaccgtcacc tccaggtcgt gaagaatctg tggaggagtt tgtacggcgt     600
aacctcggtg atgaggtttt tgagcgcctg attgaaccgt tttgttcagg tgtttatgct     660
```

-continued

```
ggtgatcctt caaaactgag catgaaagca gcgtttggga aggtttggaa actagagcaa    720
aatggtggaa gcataatagg tggtactttt aaggcaattc aggagaggaa aaacgctccc    780
aaggcagaac gagacccgcg cctgccaaaa ccacagggcc aaacagttgg ttctttcagg    840
aagggacttc gaatgttgcc agaagcaata tctgcaagat taggtagcaa agttaagttg    900
tcttggaagc tctcaggtat cactaagctg gagagcggag gatacaactt aacatatgag    960
actccagatg gtttagtttc cgtgcagagc aaaagtgttg taatgacggt gccatctcat   1020
gttgcaagtg gtctcttgcg ccctctttct gaatctgctg caaatgcact ctcaaaacta   1080
tattacccac cagttgcagc agtatctatc tcgtacccga agaagcaat ccgaacagaa    1140 tgtttgatag atggtgaact aaagggtttt gggcaattgc atccacgcac gcaaggagtt   1200
gaaacattag gaactatcta cagctcctca ctctttccaa atcgcgcacc gcccggaaga   1260
attttgctgt tgaactacat tggcgggtct acaaacaccg gaattctgtc caagtctgaa   1320
ggtgagttag tggaagcagt tgacagagat ttgaggaaaa tgctaattaa gcctaattcg   1380
accgatccac ttaaattagg agttaggta tggcctcaag ccattcctca gtttctagtt    1440
ggtcactttg atatccttga cacggctaaa tcatctctaa cgtcttcggg ctacgaaggg   1500
ctatttttgg gtggcaatta cgtcgctggt gtagccttag gccggtgtgt agaaggcgca   1560
tatgaaaccg cgattgaggt caacaacttc atgtcacggt acgcttacaa gtaa         1614
```

<210> SEQ ID NO 11
<211> LENGTH: 537
<212> TYPE: PRT
<213> ORGANISM: Artificial Sequence
<220> FEATURE:
<223> OTHER INFORMATION: Mutant type AtPPO1

<400> SEQUENCE: 11

```
Met Glu Leu Ser Leu Leu Arg Pro Thr Thr Gln Ser Leu Leu Pro Ser
1               5                   10                  15

Phe Ser Lys Pro Asn Leu Arg Leu Asn Val Tyr Lys Pro Leu Arg Leu
            20                  25                  30

Arg Cys Ser Val Ala Gly Gly Pro Thr Val Gly Ser Ser Lys Ile Glu
        35                  40                  45

Gly Gly Gly Gly Thr Thr Ile Thr Thr Asp Cys Val Ile Gly Gly
    50                  55                  60

Gly Ile Ser Gly Leu Cys Ile Ala Gln Ala Leu Ala Thr Lys His Pro
65                  70                  75                  80

Asp Ala Ala Pro Asn Leu Ile Val Thr Glu Ala Lys Asp Arg Val Gly
                85                  90                  95

Gly Asn Ile Ile Thr Arg Glu Glu Asn Gly Phe Leu Trp Glu Glu Gly
            100                 105                 110

Pro Asn Ser Phe Gln Pro Ser Asp Pro Met Leu Thr Met Val Val Asp
        115                 120                 125

Ser Gly Leu Lys Asp Asp Leu Val Leu Gly Asp Pro Thr Ala Pro Arg
    130                 135                 140

Phe Val Leu Trp Asn Gly Lys Leu Arg Pro Val Pro Ser Lys Leu Thr
145                 150                 155                 160

Asp Leu Pro Phe Phe Asp Leu Met Ser Ile Gly Gly Lys Ile Arg Ala
                165                 170                 175

Gly Phe Gly Ala Leu Gly Ile Arg Pro Ser Pro Pro Gly Arg Glu Glu
            180                 185                 190

Ser Val Glu Glu Phe Val Arg Arg Asn Leu Gly Asp Glu Val Phe Glu
```

```
            195                 200                 205
Arg Leu Ile Glu Pro Phe Cys Ser Gly Val Tyr Ala Gly Asp Pro Ser
    210                 215                 220

Lys Leu Ser Met Lys Ala Ala Phe Gly Lys Val Trp Lys Leu Glu Gln
225                 230                 235                 240

Asn Gly Gly Ser Ile Gly Gly Thr Phe Lys Ala Ile Gln Glu Arg
            245                 250                 255

Lys Asn Ala Pro Lys Ala Glu Arg Asp Pro Arg Leu Pro Lys Pro Gln
                260                 265                 270

Gly Gln Thr Val Gly Ser Phe Arg Lys Gly Leu Arg Met Leu Pro Glu
            275                 280                 285

Ala Ile Ser Ala Arg Leu Gly Ser Lys Val Lys Leu Ser Trp Lys Leu
    290                 295                 300

Leu Gly Ile Thr Lys Leu Glu Ser Gly Gly Tyr Asn Leu Thr Tyr Glu
305                 310                 315                 320

Thr Pro Asp Gly Leu Val Ser Val Gln Ser Lys Ser Val Val Met Thr
                325                 330                 335

Val Pro Ser His Val Ala Ser Gly Leu Leu Arg Pro Leu Ser Glu Ser
            340                 345                 350

Ala Ala Asn Ala Leu Ser Lys Leu Tyr Tyr Pro Pro Val Ala Ala Val
    355                 360                 365

Ser Ile Ser Tyr Pro Lys Glu Ala Ile Arg Thr Glu Cys Leu Ile Asp
370                 375                 380

Gly Glu Leu Lys Gly Phe Gly Gln Leu His Pro Arg Thr Gln Gly Val
385                 390                 395                 400

Glu Thr Leu Gly Thr Ile Tyr Ser Ser Leu Phe Pro Asn Arg Ala
                405                 410                 415

Pro Pro Gly Arg Ile Leu Leu Leu Asn Met Ile Gly Ser Thr Asn
            420                 425                 430

Thr Gly Ile Leu Ser Lys Ser Glu Gly Glu Leu Val Glu Ala Val Asp
    435                 440                 445

Arg Asp Leu Arg Lys Met Leu Ile Lys Pro Asn Ser Thr Asp Pro Leu
    450                 455                 460

Lys Leu Gly Val Arg Val Trp Pro Gln Ala Ile Pro Gln Phe Leu Val
465                 470                 475                 480

Gly His Phe Asp Ile Leu Asp Thr Ala Lys Ser Ser Leu Thr Ser Ser
                485                 490                 495

Gly Tyr Glu Gly Leu Phe Leu Gly Gly Asn Tyr Val Ala Gly Val Ala
            500                 505                 510

Leu Gly Arg Cys Val Glu Gly Ala Tyr Glu Thr Ala Ile Glu Val Asn
    515                 520                 525

Asn Phe Met Ser Arg Tyr Ala Tyr Lys
    530                 535

<210> SEQ ID NO 12
<211> LENGTH: 473
<212> TYPE: PRT
<213> ORGANISM: Artificial Sequence
<220> FEATURE:
<223> OTHER INFORMATION: CyPPO2 mutant

<400> SEQUENCE: 12

Met Glu Leu Leu Asp Thr Leu Ile Val Gly Ala Gly Ile Ser Gly Leu
1               5                   10                  15

Ser Leu Ala His Ala Leu His Lys Glu Ala Thr Ser Ala Ser Pro Leu
```

```
            20                  25                  30
Lys Ile Leu Val Ala Glu Ser Gln Gly Arg Val Gly Gly Asn Ile Thr
         35                  40                  45
Thr Val Thr Ala Glu Gly Phe Leu Trp Glu Gly Pro Asn Ser Phe
     50                  55                  60
Ser Pro Thr Pro Glu Leu Met Lys Leu Ala Val Asp Val Gly Leu Lys
 65                  70                  75                  80
Gln Glu Leu Ile Phe Ala Asp Arg Lys Leu Pro Arg Phe Val Tyr Trp
                     85                  90                  95
Glu Asn Lys Leu Gln Pro Leu Ser Phe Pro Gly Lys Leu Arg Ala Leu
                100                 105                 110
Phe Gly Ala Leu Gly Phe Val Ala Pro Ala Met Gly Asp Arg Leu Ser
             115                 120                 125
Gln Gln Gly Asn Glu Glu Thr Val Ser Gln Phe Phe Arg Arg His Leu
         130                 135                 140
Gly Thr Glu Val Met Gln Arg Leu Val Glu Pro Phe Val Ser Gly Val
145                 150                 155                 160
Tyr Ala Gly Asp Pro Gln Gln Leu Ser Ala Ala Ala Phe Gly Arg
                 165                 170                 175
Val Ala Lys Met Ala Asp Val Gly Gly Leu Val Ala Gly Ala Leu
             180                 185                 190
Leu Ser Ala Lys Asn Arg Pro Lys Lys Met Pro Ala Asp Pro Asn Val
         195                 200                 205
Pro Lys Thr Lys Pro Gly Glu Leu Gly Ser Phe Lys Gln Gly Leu Lys
         210                 215                 220
Ala Leu Pro Glu Ala Ile Ala Ala Lys Leu Gly Asp Arg Val Lys Leu
225                 230                 235                 240
Asn Trp His Leu Thr Arg Leu Gln Arg Thr Glu Arg Glu Thr Tyr Ile
                 245                 250                 255
Ala Glu Phe Ser Thr Pro Asp Gly Gln Gln Glu Val Glu Ala Arg Thr
             260                 265                 270
Val Val Leu Thr Thr Pro Ala Tyr Val Thr Ala Asp Leu Leu Gln Pro
         275                 280                 285
Leu Glu Pro Gln Val Ser Ser Ala Leu Gln Ala Phe Thr Tyr Pro Thr
         290                 295                 300
Val Ala Ser Val Val Leu Ala Tyr Pro Gln Ser Asp Val Lys Gly Lys
305                 310                 315                 320
Leu Val Gly Phe Gly Asn Leu Ile Pro Arg Gly Gln Gly Ile Arg Cys
                 325                 330                 335
Leu Gly Thr Ile Trp Thr Ser Ser Leu Phe Pro Asp Arg Ala Pro Ala
             340                 345                 350
Gly Trp Gln Thr Leu Thr Ser Tyr Ile Gly Gly Ala Thr Asp Ser Glu
         355                 360                 365
Ile Gly Asn Leu Asp Ser Glu Gln Ile Val Arg Glu Val His Arg Asp
         370                 375                 380
Leu Ser Arg Ile Leu Leu Lys Pro Asp Val Pro Gln Pro Lys Val Leu
385                 390                 395                 400
Thr Val Lys Leu Trp Lys Arg Ala Ile Pro Gln Tyr Asn Leu Gly His
                 405                 410                 415
Phe Asp Arg Leu Gln Gln Ile Asp Glu Gly Leu Lys Ser Leu Pro Gly
             420                 425                 430
Val Tyr Leu Cys Ser Asn Tyr Val Gly Gly Val Ala Leu Gly Asp Cys
         435                 440                 445
```

Val Arg Arg Gly Phe Asp Arg Ala Arg Glu Val Gly Glu Tyr Leu Gln
    450             455                 460

Lys Lys Gln Ser Asp Thr Arg Ser Ile
465                 470

<210> SEQ ID NO 13
<211> LENGTH: 1422
<212> TYPE: DNA
<213> ORGANISM: Artificial Sequence
<220> FEATURE:
<223> OTHER INFORMATION: CyPPO2 mutant

<400> SEQUENCE: 13

```
atggaactat tagataccct tgattgtggt gcgggtatta gcggtttgag tttggcgcac      60
gcacttcaca aggaagcaac gagtgcatcg ccgctgaaga ttttagtcgc tgagagtcag     120
ggacgtgtgg gcgggaacat cacgactgtg acagcagagg ggtttctctg ggaggagggc     180
ccgaacagtt tttcgccgac gccggaattg atgaagttgg ctgtggatgt gggattgaag     240
caggagttga ttttttgccga tcgcaaattg cctcgttttg tgtattggga aaataagctg     300
caaccgctga gttttccggg gaaactgcgg gcgttgttcg gggctttggg gtttgtcgcg     360
ccggcaatgg gcgatcgact ttcgcagcag ggtaacgagg aaacagtttc tcaatttttc     420
cgccgtcatc tcggtacgga agtgatgcag cggttggtgg aacctttgt ttctggggtt     480
tatgccggcg atccgcaaca acttagcgcg gcggcggctt ttggccgggt agccaagatg     540
gctgatgtgg gtggcgggct ggtggcgggg gcgctgcttt ctgctaaaaa cagaccgaag     600
aaaatgcctg cagacccgaa tgttcctaaa actaagccgg gggagttggg ttcgttcaag     660
caggggttga aggcttttgcc agaggcgatc gctgctaagt tgggcgatcg agtgaaactc     720
aactggcact tgactcgcct ccagcgcaca gaacgcgaaa cttacattgc tgaattctcg     780
acgcccgacg gacagcagga agttgaggcg cgcaccgtgg ttttgacaac gcccgcttac     840
gttacagccg atttgttgca acctctggaa ccgcaagtta gcagcgcttt acaagctttt     900
acttatccta cggttgcctc cgttgtctta gcatacccgc agtcggatgt caagggtaaa     960
ttagtgggtt ttgaaaattt aattccgagg gggcagggaa ttcgctgtct cgggacgatt    1020
tggacatcga gtttatttcc cgatcgcgcg cctgcagggt ggcaaactct caccagttac    1080
atcggcgggg caacagactc ggaaattggc aatctcgact cagaacaaat cgttcgggag    1140
gtacaccgag atttgtctcg gatttgctg aaaccagatg tgccacagcc aaaagtttta    1200
acggtgaagc tgtggaaacg ggcgattcct cagtacaatt gggggcattt cgatcgcctg    1260
caacaaatcg atgagggctt aaaatctttg cctggagtgt atttgtgcag caactacgtt    1320
ggcggagtgg ctttgggaga ttgcgtcgcga aggggtttcg atcgtgcgcg agaagtgggc    1380
gagtatttgc agaagaaaca atcagatact cgatcgatct ga                      1422
```

<210> SEQ ID NO 14
<211> LENGTH: 466
<212> TYPE: PRT
<213> ORGANISM: Artificial Sequence
<220> FEATURE:
<223> OTHER INFORMATION: CyPPO4 mutant

<400> SEQUENCE: 14

Met Thr His Val Leu Asp Ser Leu Ile Val Gly Ala Gly Ile Ser Gly
1               5                   10                  15

Leu Ala Leu Ala His Ala Leu His Gln Asn Gln Asp His Gln Leu Pro

-continued

```
                20                  25                  30
Leu Asn Ile Leu Val Ser Glu His Gln Gly Arg Val Gly Gly Asn Ile
                35                  40                  45
Thr Thr Val Ser Glu Gly Glu Phe Leu Trp Glu Gly Pro Asn Ser
        50                  55                  60
Phe Ser Pro Thr Pro Glu Leu Leu Lys Leu Ala Val Glu Val Gly Leu
65                  70                  75                  80
Lys Pro Glu Leu Val Phe Ala Asp Arg Lys Leu Pro Arg Tyr Val Tyr
                    85                  90                  95
Trp Asn Gly Gln Leu Met Pro Leu Ser Pro Gly Gly Lys Leu Arg Ala
                    100                 105                 110
Leu Thr Gly Ala Leu Gly Phe Val Gln Pro Ala Met Gly Glu Ser Leu
        115                 120                 125
Ser Gln Gln Asn Gly Glu Glu Thr Ile Ser Gln Phe Phe Glu Arg His
        130                 135                 140
Leu Gly Ser Glu Val Leu Lys Arg Leu Val Glu Pro Phe Val Ser Gly
145                 150                 155                 160
Val Tyr Ala Gly Asp Pro Gln Gln Leu Glu Ile Ser Ser Ala Phe Ala
                    165                 170                 175
Arg Val Ala Arg Met Ala Tyr Ser Gly Gly Leu Val Ala Gly Ala
                    180                 185                 190
Val Leu Ser Arg Arg Gln Asn Lys Ser Pro Arg Ser Pro Ala Asp Pro
                195                 200                 205
Ser Ile Pro Gln Thr Lys Arg Gly Glu Leu Gly Ser Phe Arg Gln Gly
        210                 215                 220
Ile Gly Ala Leu Pro Asn Ala Ile Ala Lys Gln Leu Gly Asp Gln Leu
225                 230                 235                 240
Lys Leu Asn Trp Gln Leu Thr Arg Leu Glu Arg Thr Glu Asn Gln Thr
                    245                 250                 255
Tyr Arg Ala Glu Phe Ser Thr Pro Glu Gly Val Gln Gln Val Glu Thr
                    260                 265                 270
Arg Thr Val Val Leu Thr Thr Pro Ala Tyr Val Thr Ala Glu Ile Leu
                    275                 280                 285
Lys Pro Leu Gln Leu Gln Val Ser Gln Thr Leu Thr Glu Ile Pro Tyr
                    290                 295                 300
Pro Pro Val Ala Cys Val Val Leu Ala Tyr Pro Val Ser Ala Leu Lys
305                 310                 315                 320
Gln Lys Leu Thr Gly Phe Gly Asn Leu Val Pro Arg Gly Gln Gly Ile
                    325                 330                 335
Arg Thr Leu Gly Thr Ile Trp Thr Ser Ser Leu Phe Pro Gly Arg Ala
                    340                 345                 350
Pro Gln Gly Trp Gln Val Leu Thr Ser Tyr Ile Gly Gly Ala Thr Asp
                355                 360                 365
Pro Glu Ile Gly Glu Leu Glu Asp Asp Gln Ile Val Glu Ala Val His
                370                 375                 380
Gln Asp Leu Arg His Ile Leu Leu Lys Glu Asp Ile Ser Pro Lys Val
385                 390                 395                 400
Leu Ala Val His Leu Trp Lys Arg Ala Ile Pro Gln Tyr Asn Leu Gly
                    405                 410                 415
His Gln Gln Arg Leu Gln His Val Asn Glu Gly Leu Glu Ala Met Pro
                    420                 425                 430
Gly Leu Tyr Leu Cys Ser Asn Tyr Ile Asp Gly Val Ala Leu Gly Asp
            435                 440                 445
```

```
Cys Val Arg Arg Ser Ile Gly Gln Ala Asn Glu Ile Leu Ser Phe Leu
     450                 455                 460

Gly Gln
465

<210> SEQ ID NO 15
<211> LENGTH: 1401
<212> TYPE: DNA
<213> ORGANISM: Artificial Sequence
<220> FEATURE:
<223> OTHER INFORMATION: CyPPO4 mutant

<400> SEQUENCE: 15
atgactcacg tactcgatag tttaatcgtc ggtgcaggca ttagcggcct ggcgttagct      60
catgctctcc atcagaacca agatcatcaa ttgcctctca acattcttgt cagcgagcat     120
caaggacggg taggaggaaa tataaccaca gtatccgaag agaatttct  tgggaagaa     180
ggccccaata gttttctcc  aacccctgag ttactgaagt tagcggtaga agtaggtctt    240
aagcctgagc tagtctttgc cgatcgcaag ttacctcggt acgtttactg gaatggtcaa    300
ctcatgcctt taagtcctgg aggtaaactt cgagcattaa cggggcatt  ggggtttgta    360
caacccgcga tgggagaatc gttaagtcaa caaaatgggg aagaaacgat ctcgcagttt    420
tttgagcgtc atttgggttc agaagttctc aagcgactgg ttgaacccct tgttctggt     480
gtttatgcag gcgatcccca gcaactcgaa attagctcgg cttttgcccg agtcgcacgt    540
atggcttaca gtggcggtgg attggttgct ggagcggttt atcgcgtcg  tcagaacaaa    600
tctccgcgat cgcctgccga cccgtctatt ccccaaacta acggggaga  gttggggtct    660
tttcgtcagg ggattggagc cttacccaat gcgatcgcca acagttagg  cgatcaactc    720
aaattaaact ggcaactcac ccgtctcgaa cggactgaaa accaaaccta tcgggctgaa    780
ttttcgactc cagaaggggt tcaacaggta gaaactcgaa cggtggtgtt gacgactccg    840
gcctatgtca cagcagaaat tctcaaaccg ttgcaactcc aagtcagtca acgttaact     900
gaaattccct atccccggt  ggcttgcgtc gttttagcct atcccgtttc agctttaaag    960
cagaaattaa ccggatttgg caatttagtt ccccgaggac aagggattcg acgttaggc    1020
acgatttgga catcgagttt atttcctggt cgcgcccccc aaggctggca agtcctcacc   1080
agttatattg gcggagcgac ggatccagaa attggagagt tagaagatga tcaaattgtt   1140
gaggcggttc atcaagattt gcgtcacatt ttactcaaag aagatatctc tcccaaagtg   1200
ctagccgtgc atctgtggaa acgtgctatc cctcaataca atctcggaca ccaacaacgg   1260
ttacaacacg ttaatgaggg tctagaggca atgccggggt tatatctgtg tagcaactat   1320
atcgacggtg tagcgttggg agattgtgtg cgtcgttcta tcggacaagc taacgaaatt   1380
ctcagttttt tgggtcaata g                                             1401

<210> SEQ ID NO 16
<211> LENGTH: 453
<212> TYPE: PRT
<213> ORGANISM: Artificial Sequence
<220> FEATURE:
<223> OTHER INFORMATION: CyPPO8 mutant

<400> SEQUENCE: 16

Met Ile Asp Thr Leu Ile Val Gly Ala Gly Ile Ser Gly Leu Ser Ala
1               5                   10                  15

Ala Tyr Arg Leu Asp Glu Lys Gln Arg Gln Val Leu Val Ala Glu Lys
```

```
                    20                  25                  30
Arg Asp Arg Ala Gly Gly Asn Ile Thr Ser Gln Gln Ser Gly Asp Phe
                35                  40                  45
Leu Trp Glu Glu Gly Pro Asn Ser Phe Ser Pro Thr Pro Glu Leu Leu
 50                  55                  60
Lys Leu Ala Val Asp Ala Gly Leu Arg Asn Glu Leu Ile Phe Ala Asp
 65                  70                  75                  80
Arg Gly Leu Pro Arg Tyr Val Tyr Trp Glu Gly Lys Leu Arg Pro Leu
                85                  90                  95
Ser Pro Ile Gly Lys Leu Arg Ala Leu Thr Gly Ala Leu Gly Phe Ile
                100                 105                 110
Pro Pro Gln Val Ser Gln Glu Glu Thr Val Ala Asp Phe Phe Thr
            115                 120                 125
Arg His Leu Gly Ser Glu Val Ala Gln Arg Leu Val Ser Pro Phe Val
            130                 135                 140
Ser Gly Val Tyr Ala Gly Asp Val Asp Gln Leu Ser Ala Glu Ala Ala
145                 150                 155                 160
Phe Gly Arg Val Thr Gln Leu Ala Asp Val Gly Gly Leu Val Ala
                165                 170                 175
Gly Ala Ile Leu Cys Arg Arg Gln Lys Pro Lys Ser Thr Pro Lys Thr
                180                 185                 190
Ala Lys Pro Ser Asp Ile Pro Glu Thr Lys Ser Gly Gln Leu Gly Ser
            195                 200                 205
Phe Lys Glu Gly Leu Gln Gln Leu Pro Ser Ala Ile Val Ser Gln Leu
            210                 215                 220
Gly Asp Lys Val Lys Phe Gln Trp Glu Leu Lys Asn Ile Ser Pro His
225                 230                 235                 240
Pro Glu Ser Gly Tyr Val Ala Thr Phe Ser Thr Pro Glu Gly Glu Gln
                245                 250                 255
Thr Val Glu Ala Lys Thr Val Ile Leu Thr Thr Pro Ala Tyr Val Thr
                260                 265                 270
Ala Ser Leu Val Lys Asp Leu Ser Pro Gln Ala Ser Gln Ala Leu Asn
            275                 280                 285
Glu Ile Ser Tyr Pro Pro Val Ala Cys Val Val Leu Ala Tyr Pro Asp
            290                 295                 300
Glu Ala Leu Arg Phe Pro Leu Lys Gly Phe Gly Asn Leu Asn Pro Arg
305                 310                 315                 320
Ser Gln Gly Ile Arg Thr Leu Gly Thr Ile Trp Ser Ser Thr Leu Phe
                325                 330                 335
Pro Gly Arg Thr Pro Lys Gly Trp His Leu Leu Thr Asn Phe Ile Gly
            340                 345                 350
Gly Ala Thr Asp Pro Ala Ile Ala Glu Leu Ser Glu Asp Gln Ile Ile
            355                 360                 365
Glu Gln Val His Gln Asp Leu Gln Gln Ala Val Ile Lys Ser Gly Ser
            370                 375                 380
Ile Pro Lys Pro Leu Ala Val His Leu Trp Ser Lys Ala Ile Pro Gln
385                 390                 395                 400
Tyr Asn Leu Gly His Leu Lys Arg Leu Glu Thr Ile Arg Asn His Leu
                405                 410                 415
Lys Pro Phe Ser Gly Leu Phe Leu Ser Ser Asn Tyr Leu Asp Gly Val
            420                 425                 430
Ala Leu Gly Asp Cys Val Arg Arg Gly Glu Glu Ser Ser Gln Ala Val
            435                 440                 445
```

Leu Asp Tyr Leu Gly
    450

<210> SEQ ID NO 17
<211> LENGTH: 1362
<212> TYPE: DNA
<213> ORGANISM: Artificial Sequence
<220> FEATURE:
<223> OTHER INFORMATION: CyPPO8 mutant

<400> SEQUENCE: 17

```
atgatagata ctttaattgt gggagcaggg attagtggtt taagtgctgc gtatcgactc      60
gatgagaagc agcgccaagt gctggttgca gaaaagcgcg atcgcgctgg gggaaatatc     120
accagccaac aaagtggcga tttcctctgg gaagaaggac cgaacagttt ttctcccaca     180
ccagaactcc taaaactagc ggttgatgcg ggcttaagaa atgagttaat ctttgctgat     240
cgcggacttc cccgttatgt ttattgggag gggaaactgc gccctctgag tccaatcggg     300
aaactacggg cgttaacggg tgcattaggc tttattcccc cgcaagtgtc gagtcaggaa     360
gaaacggttg cggactttt tacccgtcat ctcggttcag aagtagccca acggttagtg      420
agtccgtttg tgtctggggt ttatgcaggg gatgtggatc aactcagtgc ggaagctgca     480
tttggacgag ttacccaact ggcggatgtg ggcggtggac tggtcgcagg tgcgatttta     540
tgtcgtcgtc aaaagccaaa gtcaaccccca aaaacggcta aaccgtctga tattccagaa    600
acaaagtctg gacagttagg ttcatttaag gaaggattac aacaattacc cagcgcgatc     660
gtttctcaac tgggagacaa agtaaagttt caatgggaac tgaaaaatat ctccctcat      720
ccagaatcgg gttacgtcgc gacattttcc acaccagagg gagaacaaac agtcgaagcc     780
aaaaccgtta tcctcaccac tcccgcctac gttaccgcct ctctggtcaa agatttatca     840
cctcaagcca gtcaagcctt aaacgaaatt tcctatcccc ccgtagcttg tgtggtctta     900
gcctatcccg atgaagccct ccgttttccc ctcaaaggat tggtaatct taaccctcgc      960
agtcaaggaa tccgcactct tggtacaatt tggagttcaa cactctttcc aggacgcacg    1020
ccgaaaggtt ggcatctctt aaccaatttt attggcggtg caactgatcc cgcaattgct    1080
gaactcagtg aagatcaaat tattgaacaa gtccatcaag acttacaaca agcggtgatt    1140
aaatcgggaa gtatcccgaa acccttagcc gttcatttgt ggtcaaaagc gattccgcaa    1200
tacaatctcg gacatctgaa acggttagaa accatccgca atcacttaaa acccttctct    1260
ggactctttt tatcgagtaa ctatctcgat ggcgttgcgt tgggtgattg tgtgcgccga    1320
ggggaagaga gtagtcaagc cgtgttagat tatttgggtt aa                        1362
```

<210> SEQ ID NO 18
<211> LENGTH: 39
<212> TYPE: DNA
<213> ORGANISM: Artificial Sequence
<220> FEATURE:
<223> OTHER INFORMATION: PCC7112_BmHIF primer

<400> SEQUENCE: 18

```
ccccggatcc atggaactat tagataccct tgattgtggg                           39
```

<210> SEQ ID NO 19
<211> LENGTH: 30
<212> TYPE: DNA
<213> ORGANISM: Artificial Sequence
<220> FEATURE:
<223> OTHER INFORMATION: PCC7112_StuIR primer

<400> SEQUENCE: 19
cccaggcctg atcgatcgag tatctgattg                                30

<210> SEQ ID NO 20
<211> LENGTH: 33
<212> TYPE: DNA
<213> ORGANISM: Artificial Sequence
<220> FEATURE:
<223> OTHER INFORMATION: PCC7418_BmHIF primer

<400> SEQUENCE: 20
ccccggatcc atgatagata ctttaattgt ggg                             33

<210> SEQ ID NO 21
<211> LENGTH: 30
<212> TYPE: DNA
<213> ORGANISM: Artificial Sequence
<220> FEATURE:
<223> OTHER INFORMATION: PCC7418_XhoIR primer

<400> SEQUENCE: 21 cccctcgag acccaaataa tctaacacgg                                 30

<210> SEQ ID NO 22
<211> LENGTH: 30
<212> TYPE: DNA
<213> ORGANISM: Artificial Sequence
<220> FEATURE:
<223> OTHER INFORMATION: PCC8106_BglIIF primer

<400> SEQUENCE: 22
ccccagatct atgactcacg tactcgatag                                30

<210> SEQ ID NO 23
<211> LENGTH: 34
<212> TYPE: DNA
<213> ORGANISM: Artificial Sequence
<220> FEATURE:
<223> OTHER INFORMATION: PCC8106_XhoIR primer

<400> SEQUENCE: 23 cccctcgag ttgacccaaa aaactgagaa tttc                            34

<210> SEQ ID NO 24
<211> LENGTH: 30
<212> TYPE: DNA
<213> ORGANISM: Artificial Sequence
<220> FEATURE:
<223> OTHER INFORMATION: CyPPO12_BamHIF primer

<400> SEQUENCE: 24
ccccggatcc atggaactct tggatactct                                30

<210> SEQ ID NO 25
<211> LENGTH: 30
<212> TYPE: DNA
<213> ORGANISM: Artificial Sequence
<220> FEATURE:
<223> OTHER INFORMATION: CyPPO12_XhoIR primer

<400> SEQUENCE: 25 cccctcgag gattgacctg gtatcagatt                                 30

<210> SEQ ID NO 26

```
<211> LENGTH: 212
<212> TYPE: DNA
<213> ORGANISM: Artificial Sequence
<220> FEATURE:
<223> OTHER INFORMATION: cTP (chloroplast transit peptide) PCR product

<400> SEQUENCE: 26
tctagaatgg agttatctct ctccgtccg acgactcaat cgcttcttcc gtcgttttcg       60
aagcccaatc tccgattaaa tgtttataag cctcttagac tccgttgttc agtggccggt     120
ggaccaaccg tcggatcttc aaaaatcgaa ggcggaggag gcctcgaggc gcgccgggcc     180
caggcctacg cgtttaatta aacctaggat cc                                    212

<210> SEQ ID NO 27
<211> LENGTH: 156
<212> TYPE: DNA
<213> ORGANISM: Artificial Sequence
<220> FEATURE:
<223> OTHER INFORMATION: cTP(chloroplast transit peptide)

<400> SEQUENCE: 27
atggagttat ctcttctccg tccgacgact caatcgcttc ttccgtcgtt ttcgaagccc       60
aatctccgat taaatgttta taagcctctt agactccgtt gttcagtggc cggtggacca     120
accgtcggat cttcaaaaat cgaaggcgga ggaggc                                156

<210> SEQ ID NO 28
<211> LENGTH: 72
<212> TYPE: DNA
<213> ORGANISM: Artificial Sequence
<220> FEATURE:
<223> OTHER INFORMATION: HA(hemaglutinin) tag

<400> SEQUENCE: 28
atgtatcctt atgatgttcc agattatgct agtcttatgt acccatacga cgtgcctgac       60
tacgcatcat tg                                                           72

<210> SEQ ID NO 29
<211> LENGTH: 39
<212> TYPE: DNA
<213> ORGANISM: Artificial Sequence
<220> FEATURE:
<223> OTHER INFORMATION: CyPPO2Nt98%_F primer

<400> SEQUENCE: 29
atctgatcaa aagcaatttt ctgagttttc cggggaaac                              39

<210> SEQ ID NO 30
<211> LENGTH: 38
<212> TYPE: DNA
<213> ORGANISM: Artificial Sequence
<220> FEATURE:
<223> OTHER INFORMATION: CyPPO2Nt98%_R primer

<400> SEQUENCE: 30
caattggatt tgaaggtaac ggttgcagct tattttcc                               38

<210> SEQ ID NO 31
<211> LENGTH: 40
<212> TYPE: DNA
<213> ORGANISM: Artificial Sequence
<220> FEATURE:
<223> OTHER INFORMATION: CyPPO4-Nt-98%_F primer

<400> SEQUENCE: 31
```

```
atctgatcaa aagcaatttt ttaagtcctg gaggtaaact                    40

<210> SEQ ID NO 32
<211> LENGTH: 38
<212> TYPE: DNA
<213> ORGANISM: Artificial Sequence
<220> FEATURE:
<223> OTHER INFORMATION: CyPPO4-Nt-98%_R primer

<400> SEQUENCE: 32
caattggatt tgaaggtaaa ggcatgagtt gaccattc                      38

<210> SEQ ID NO 33
<211> LENGTH: 39
<212> TYPE: DNA
<213> ORGANISM: Artificial Sequence
<220> FEATURE:
<223> OTHER INFORMATION: CyPPO8_Nt98%-F primer

<400> SEQUENCE: 33
atctgatcaa aagcaatttt ctgagtccaa tcgggaaac                     39

<210> SEQ ID NO 34
<211> LENGTH: 39
<212> TYPE: DNA
<213> ORGANISM: Artificial Sequence
<220> FEATURE:
<223> OTHER INFORMATION: CyPPO8_Nt98%-R primer

<400> SEQUENCE: 34
caattggatt tgaaggtaaa gggcgcagtt tcccctccc                     39
```

METHODS FOR CONFERRING OR ENHANCING HERBICIDE RESISTANCE ON PLANTS AND/OR ALGA WITH PROTOPORPHYRINOGEN OXIDASE VARIANTS

CROSS-REFERENCE TO RELATED APPLICATIONS

This application is a 371 of PCT/KR2015/013812 filed Dec. 16, 2015, claiming priority to Korean Patent Application No. 10-2014-0181791 filed Dec, 16, 2014, the contents of each of which are incorporated herein by reference in their entirety.

TECHNICAL FIELD

Provided are methods for conferring and/or enhancing herbicide resistance on plants and/or alga including agricultural crops by introducing prokaryote-derived protoporphyrinogen oxidase variants.

BACKGROUND ART

A porphyrin biosynthetic pathway serves for the synthesis of chlorophyll and heme which play a vital role in plant metabolism, and it takes place in the chloroplast. In this pathway, protoporphyrinogen IX oxidase (hereinafter, referred to as PPO; EC:1.3.3.4) catalyzes the oxidation of protoporphyrinogen IX to protoporphyrin IX. After the oxidation of protoporphyrinogen IX to protoporphyrin IX, protoporphyrin IX binds with magnesium by Mg-chelatase to synthesize chlorophyll, and it binds with iron by Fe-chelatase to synthesize heme.

Therefore, when PPO activity is inhibited, synthesis of chlorophylls and heme is inhibited and the substrate protoporphyrinogen IX leaves the normal porphyrin biosynthetic pathway, resulting in the rapid export of protoporphyrinogen IX from the chloroplast to the cytoplasm, and cytoplasmic protoporphyrin IX accumulation caused by the oxidation. Protoporphyrin IX thus accumulated generates highly reactive singlet oxygen ($^1O_2$) in the presence of light and oxygen molecules to destroy cell membrane, rapidly leading to plant cell death. Based on this principle, herbicides inhibiting PPO activity have been developed. Until now, there have been 9 families of herbicides, including pyrimidinediones, diphenyl-ethers, phenylpyrazoles, N-phenylphthalimides, thiadiazoles, oxadiazoles, triazolinones, oxazolidinediones, and others herbicides, which are classified according to their chemical structures.

Further, in order to prevent effects of these herbicides on the growth of crops while using the herbicides, there is a need to provide herbicide resistance for the crops.

Meanwhile, as photosynthetic organisms, algae have the capacity to transform sunlight into energy that can be used to synthesize a variety of useful compounds. Through photosynthetic carbon fixation, algae can convert $CO_2$ to sugar, starch, lipids, fats, or other biomolecules, for example, thereby removing a greenhouse gas from the atmosphere. Furthermore, large scale cultures of algae can be used to produce a variety of biomolecules for use as industrial enzymes, therapeutic compounds and proteins, nutritional products, commercial products, or fuel products, for example.

A major problem in the large scale cultures of algae in bioreactors or open or closed ponds is that they can become contaminated by other, highly competitive but unwanted species of algae fungi and bacteria, as well as by rotifers and other zooplankton that devour the desired species in the cultures.

Thus, there is a need to confer herbicide resistance to the algae, in order for the herbicide resistant algae to be able to grow in the presence of the herbicide at a concentration that deters growth of competing organisms not harboring the herbicide resistance gene.

DISCLOSURE

Technical Problem

It is observed that hemY-type PPO gene derived from prokaryotes conferred a broad herbicide resistance against 9 types of PPO-inhibiting herbicides. In addition, it is verified that this gene is expressed in plants or algae, and confers a herbicide resistance trait on the plants or algae. Based thereon, methods for conferring and/or enhancing herbicide resistance on plants including agricultural crops or algae by introducing prokaryote-derived protoporphyrinogen oxidase variants are provided.

One embodiment provides a composition for conferring and/or enhancing herbicide resistance on a plant or an alga, the composition including one or more polypeptides selected from the group consisting of a polypeptide containing an amino acid sequence of SEQ ID NO: 1 or an amino acid sequence having 95% or higher homology thereto; a polypeptide containing an amino acid sequence of SEQ ID NO: 3 or an amino acid sequence having 95% or higher homology thereto; a polypeptide containing an amino acid sequence of SEQ ID NO: 5 or an amino acid sequence having 95% or higher homology thereto; and a polypeptide containing an amino acid sequence of SEQ ID NO: 7 or an amino acid sequence having 95% or higher homology thereto.

Another embodiment provides a composition for conferring and/or enhancing herbicide resistance trait on a plant or an alga, the composition including one or more genes selected from the group consisting of gene encoding the corresponding polypeptide containing the amino acid sequence of SEQ ID NO: 1 or the amino acid sequence having 95% or higher homology thereto; gene encoding the corresponding polypeptide containing the amino acid sequence of SEQ ID NO: 3 or the amino acid sequence having 95% or higher homology thereto; gene encoding the corresponding polypeptide containing the amino acid sequence of SEQ ID NO: 5 or the amino acid sequence having 95% or higher homology thereto; and gene encoding the corresponding polypeptide containing the amino acid sequence of SEQ ID NO: 7 or the amino acid sequence having 95% or higher homology thereto.

In an exemplary embodiment, the gene may include a gene containing a nucleotide sequence of SEQ ID NO: 2 or a nucleotide sequence having 95% or higher homology thereto; a gene containing a nucleotide sequence of SEQ ID NO: 4 or a nucleotide sequence having 95% or higher homology thereto; a gene containing a nucleotide sequence of SEQ ID NO: 6 or a nucleotide sequence having 95% or higher homology thereto; or a gene containing a nucleotide sequence of SEQ ID NO: 8 or a nucleotide sequence having 95% or higher homology thereto.

In another exemplary embodiment, the gene may be included in a recombinant plant expression gene cassette vector or a recombinant algae expression gene cassette vector.

In another exemplary embodiment, the herbicide may be protoporphyrinogen oxidase-inhibiting herbicides.

In another exemplary embodiment, the herbicide may be one or more selected from the group consisting of pyrimidinediones, diphenyl-ethers, phenylpyrazoles, N-phenyl-phthalimides, thiadiazoles, oxadiazoles, triazolinones, oxazolidinediones, and any combinations thereof.

In another exemplary embodiment, the herbicide may be one or more selected from the group consisting of butafenacil, saflufenacil, benzfendizone, tiafenacil, fomesafen, oxyfluorfen, aclonifen, acifluorfen, bifenox, ethoxyfen, lactofen, chlomethoxyfen, chlorintrofen, fluoroglycofen-ethyl, halosafen, pyraflufen-ethyl, fluazolate, flumioxazin, cinidon-ethyl, flumiclorac-pentyl, fluthiacet, thidiazimin, oxadiargyl, oxadiazon, carfentrazone, sulfentrazone, azafenidin, pentoxazone, pyraclonil, flufenpyr-ethyl, profluazol and any combinations thereof.

In another exemplary embodiment, the plant may be monocotyledonous plants, dicotyledonous plants, herbaceous plants, or/and woody plants.

In another exemplary embodiment, the plant or the alga may be genetically engineered to additionally contain a second polypeptide or a second gene encoding the corresponding peptides, thereby having more broadened herbicide resistance against the second herbicide.

In another exemplary embodiment, the second herbicide may include a cell division-inhibiting herbicide, a photosynthesis-inhibiting herbicide, an amino acid synthesis-inhibiting herbicide, a plastid-inhibiting herbicide, and a cell membrane-inhibiting herbicide, but is not limited thereto.

In another exemplary embodiment, the second herbicide may be exemplified by glyphosate, glufosinate, dicamba, 2,4-D(2,4-Dichlorophenoxyacetic acid), isoxaflutole, ALS (acetolactate synthase)-inhibiting herbicide, a photosystem II-inhibiting herbicide, a phenylurea-based herbicide, a bromoxynil-based herbicide or any combinations thereof, but is not limited thereto.

In another exemplary embodiment, the second polypeptide conferring herbicide-resistance on a plant or an alga may be exemplified by the peptides conferring herbicide resistance with one or more selected from the group consisting of glyphosate herbicide-resistant EPSPS (glyphosate resistant 5-enolpyruvylshikimate-3-phosphate synthase), GOX (glyphosate oxidase), GAT (glyphosate-N-acetyltransferase), or glyphosate decarboxylase; glufosinate herbicide-resistant PAT (phosphinothricin-N-acetyltransferase); dicamba herbicide-resistant DMO (monooxygenase); 2,4-D herbicide-resistant 2,4-D monooxygenase or AAD(aryloxyalkanoate Dioxygenase); ALS-inhibiting sulfonylurea-based herbicide-resistant ALS (Acetolactate Synthase), AHAS (acetohydroxyacid synthase), or AtAHASL (Acetohydroxyacid synthase Large Subunit); photosystem II-inhibiting herbicide-resistant photosystem II protein D1; phenylurea-based herbicide-resistant cytochrome P450; plastid-inhibiting herbicide-resistant HPPD (Hydroxylphenylpyruvate dioxygenase); bromoxynil herbicide-resistant nitrilase; and any combinations thereof, but is not limited thereto.

Further, the gene encoding the second polypeptide conferring herbicide-resistance may be exemplified by one or more selected from the nucleotide group consisting of glyphosate herbicide-resistant CP4 EPSPS, EPSPS(AG), MEPSPS, 2MEPSPS, GOXV247, GAT4601, or GAT4621 gene; glufosinate herbicide-resistant BAR, PAT, or PAT (SYN) gene; dicamba herbicide-resistant DMO gene; 2,4-D herbicide-resistant AAD-1 or AAD-12 gene; ALS-inhibiting sulfonylurea-based herbicide-resistant ALS, GM-HRA, S4-HRA, ZM-HRA, CSR1, CSR1-1, CSR1-2, SURA, or SURB; photosystem II-inhibiting herbicide-resistant PSBA gene; phenylurea herbicide-resistant CYP76B1 gene; isoxaflutole herbicide-resistant HPPDPF W336 gene; bromoxynil herbicide-resistant BXN gene; and any combinations thereof, but is not limited thereto.

Another embodiment provides genetically modified organism harboring a new or novel or/and enhanced herbicide resistance, or clone or progenies thereof, the transformant or the clone or progeny thereof expressing one or more selected from the group consisting of the polypeptides containing the amino acid sequence of SEQ ID NO: 1 or the amino acid sequence having 95% or higher homology thereto, or the gene encoding the polypeptide; the polypeptide containing the amino acid sequence of SEQ ID NO: 3 or the amino acid sequence having 95% or higher homology thereto, or the gene encoding the polypeptide; the polypeptide containing the amino acid sequence of SEQ ID NO: 5 or the amino acid sequence having 95% or higher homology thereto, or the gene encoding the polypeptide; the polypeptide containing the amino acid sequence of SEQ ID NO: 7 or the amino acid sequence having 95% or higher homology thereto, or the gene encoding the polypeptide; and any combinations thereof.

In an exemplary embodiment, the targets for genetic modification may be an alga, plant cell, protoplast, callus, hypocotyl, seed, cotyledon, shoot, or plant.

Another embodiment provides a method of generating a genetically modified plant or an alga showing a novel or novel or/and enhanced herbicide resistance, the methods include the procedures of transforming an alga, plant cell, protoplast, callus, hypocotyl, seed, cotyledon, shoot, or plant expressing one or more selected from the group consisting of the polypeptide containing the amino acid sequence of SEQ ID NO: 1 or the amino acid sequence having 95% or higher homology thereto, or the gene encoding the corresponding polypeptide; the polypeptide containing the amino acid sequence of SEQ ID NO: 3 or the amino acid sequence having 95% or higher homology thereto, or the gene encoding the corresponding polypeptide; the polypeptide containing the amino acid sequence of SEQ ID NO: 5 or the amino acid sequence having 95% or higher homology thereto, or the gene encoding the corresponding polypeptide; the polypeptide consisting of the amino acid sequence of SEQ ID NO: 7 or the amino acid sequence having 95% or higher homology thereto, or the gene encoding the corresponding polypeptide; and any combinations thereof.

Another embodiment provides a method of conferring and/or enhancing herbicide resistance on a plant or an alga. The method includes the procedure of transforming an alga, plant cell, protoplast, callus, a hypocotyl, seed, cotyledon, shoot, or plant with one or more genes selected from the group consisting of the gene encoding the polypeptide containing the amino acid sequence of SEQ ID NO: 1 or the amino acid sequence having 95% or higher homology thereto; the gene encoding the corresponding polypeptide containing the amino acid sequence of SEQ ID NO: 3 or the amino acid sequence having 95% or higher homology thereto; the gene encoding the corresponding polypeptide containing the amino acid sequence of SEQ ID NO: 5 or the amino acid sequence having 95% or higher homology thereto; the gene encoding the corresponding polypeptide containing the amino acid sequence of SEQ ID NO: 7 or the amino acid sequence having 95% or higher homology thereto; and any combinations thereof.

Another embodiment provides a method for controlling weeds in a cropland. The method includes the procedure of providing the cropland with the a genetically modified plant containing the polypeptide or gene selected from the group consisting of the polypeptide containing the amino acid sequence of SEQ ID NO: 1 or the amino acid sequence having 95% or higher homology thereto or the gene encoding the corresponding polypeptide; the polypeptide containing the amino acid sequence of SEQ ID NO: 3 or the amino acid sequence having 95% or higher homology thereto, or the gene encoding the polypeptide; the polypeptide containing the amino acid sequence of SEQ ID NO: 5 or the amino acid sequence having 95% or higher homology thereto, or the gene encoding the polypeptide; the polypeptide containing the amino acid sequence of SEQ ID NO: 7 or the amino acid sequence having 95% or higher homology thereto, or the gene encoding the polypeptide; and any combinations thereof, and then applying an effective dosage of protoporphyrinogen oxidase-inhibiting herbicides to the cropland.

In an exemplary embodiment, applying an effective dosage of a protoporphyrinogen oxidase-inhibiting herbicide to the cropland may be performed by applying two or more of protoporphyrinogen oxidase-inhibiting herbicides in combination at an effective dosage thereof, sequentially or simultaneously.

In another exemplary embodiment, the plant may genetically modified to express a second polypeptide conferring herbicide-resistance or a gene encoding the corresponding peptides. Two herbicides, protoporphyrinogen oxidase-inhibiting herbicide and the second herbicide, may be applied to the cropland at an effective dosage thereof, sequentially or simultaneously.

Another embodiment provides a method for controlling undesired aquatic species in a cultivation medium. The method includes the procedure of providing the cultivation medium with the a genetically modified alga containing the polypeptide or gene selected from the group consisting of the polypeptide containing the amino acid sequence of SEQ ID NO: 1 or the amino acid sequence having 95% or higher homology thereto or the gene encoding the corresponding polypeptide; the polypeptide containing the amino acid sequence of SEQ ID NO: 3 or the amino acid sequence having 95% or higher homology thereto, or the gene encoding the polypeptide; the polypeptide containing the amino acid sequence of SEQ ID NO: 5 or the amino acid sequence having 95% or higher homology thereto, or the gene encoding the polypeptide; the polypeptide containing the amino acid sequence of SEQ ID NO: 7 or the amino acid sequence having 95% or higher homology thereto, or the gene encoding the polypeptide; and any combinations thereof, and then applying an effective dosage of protoporphyrinogen oxidase-inhibiting herbicides to the cultivation medium.

Technical Solution

One embodiment provides a composition for conferring and/or enhancing herbicide resistance on a plant or an alga. The compositions may include one or more polypeptide selected from the group consisting of a polypeptide comprising, consisting essentially of, or consisting of an amino acid sequence of SEQ ID NO: 1 or an amino acid sequence having 95% or higher homology thereto; a polypeptide comprising, consisting essentially of, or consisting of an amino acid sequence of SEQ ID NO: 3 or an amino acid sequence having 95% or higher homology thereto; a polypeptide comprising, consisting essentially of, or consisting of an amino acid sequence of SEQ ID NO: 5 or an amino acid sequence having 95% or higher homology thereto; a polypeptide comprising, consisting essentially of, or consisting of an amino acid sequence of SEQ ID NO: 7 or an amino acid sequence having 95% or higher homology thereto; and any combinations thereof.

Another embodiment provides a composition for conferring and/or enhancing herbicide resistance on a plant or an alga. The composition may includes one or more genes selected from the group consisting of a gene encoding the corresponding polypeptide comprising, consisting essentially of, or consisting of the amino acid sequence of SEQ ID NO: 1 or the amino acid sequence having 95% or higher homology thereto; a gene encoding the corresponding polypeptide comprising, consisting essentially of, or consisting of the amino acid sequence of SEQ ID NO: 3 or the amino acid sequence having 95% or higher homology thereto; a gene encoding the corresponding polypeptide comprising, consisting essentially of, or consisting of the amino acid sequence of SEQ ID NO: 5 or the amino acid sequence having 95% or higher homology thereto; a gene encoding the corresponding polypeptide comprising, consisting essentially of, or consisting of the amino acid sequence of SEQ ID NO: 7 or the amino acid sequence having 95% or higher homology thereto; and any combinations thereof.

Still other embodiments provide a polypeptide for use in conferring or/and enhancing herbicide resistance on a plant or an alga, the polypeptide is one or more selected from the group consisting of a polypeptide comprising, consisting essentially of, or consisting of an amino acid sequence of SEQ ID NO: 1 or an amino acid sequence having 95% or higher homology thereto; a polypeptide comprising, consisting essentially of, or consisting of an amino acid sequence of SEQ ID NO: 3 or an amino acid sequence having 95% or higher homology thereto; a polypeptide comprising, consisting essentially of, or consisting of an amino acid sequence of SEQ ID NO: 5 or an amino acid sequence having 95% or higher homology thereto; polypeptide comprising, consisting essentially of, or consisting of an amino acid sequence of SEQ ID NO: 7 or an amino acid sequence having 95% or higher homology thereto; and any combinations thereof.

Still other embodiments provide a gene for use in conferring or/and enhancing herbicide resistance on a plant or an alga, the gene is one or more selected from the group consisting of a gene encoding the corresponding polypeptide comprising, consisting essentially of, or consisting of the amino acid sequence of SEQ ID NO: 1 or the amino acid sequence having 95% or higher homology thereto; a gene encoding the corresponding polypeptide comprising, consisting essentially of, or consisting of the amino acid sequence of SEQ ID NO: 3 or the amino acid sequence having 95% or higher homology thereto; a gene encoding the corresponding polypeptide comprising, consisting essentially of, or consisting of the amino acid sequence of SEQ ID NO: 5 or the amino acid sequence having 95% or higher homology thereto; a gene encoding the corresponding polypeptide comprising, consisting essentially of, or consisting of the amino acid sequence of SEQ ID NO: 7 or the amino acid sequence having 95% or higher homology thereto; and any combinations thereof.

Still other embodiments provide a transformant having herbicide resistance, the transformant being transformed with the gene.

Still other embodiments provide a method of preparing a plant or an alga having herbicide resistance, the method including transforming an alga, a plant cell, a protoplast, a callus, a hypocotyl, a seed, a cotyledon, a shoot or a plant with the gene.

Still other embodiments provide a method for conferring and/or enhancing herbicide resistance on a plant or an alga, the method including transforming an alga, a plant cell, a protoplast, a callus, a hypocotyl, a seed, a cotyledon, a shoot, or a plant with the gene.

Hereinafter, the present invention will be described in more detail.

In the present invention, provided are *Oscillatoria nigro-viridis* PCC 7112-derived PPO, which is named CyPPO2, an amino acid sequence thereof represented by SEQ ID NO: 1, and a gene encoding the corresponding peptides represented by a nucleotide sequence of SEQ ID NO: 2.

Further, provided are *Lyngbya* sp. PCC 8106 strain-derived PPO, which is named CyPPO4, an amino acid sequence thereof represented by SEQ ID NO: 3, and a gene encoding the corresponding peptides represented by a nucleotide sequence of SEQ ID NO: 4.

Further, provided are *Halothece* sp. PCC 7418 strain-derived PPO, which is named CyPPO8, an amino acid sequence thereof represented by SEQ ID NO: 5, and a gene encoding the corresponding peptides represented by a nucleotide sequence of SEQ ID NO: 6.

Further, provided are *Microcoleus vaginatus* strain-derived PPO, which is named CyPPO12, an amino acid sequence thereof represented by SEQ ID NO: 7, and a gene encoding the corresponding peptides represented by a nucleotide sequence of SEQ ID NO: 8. The amino acid sequence of CyPPO12 has 94% sequence homology with that of CyPPO2.

The herbicide-resistant PPO proteins provided herein may include an additional alteration within the scope that does not generally alter the activity of the molecules. Such alteration may include substitution, deletion, addition, and/or insertion of amino acids. For example, amino acid exchanges in proteins and peptides, which do not generally alter the activity of the molecules, are known in the art. The most commonly occurring exchanges are Ala/Ser, Val/Ile, Asp/Glu, Thr/Ser, Ala/Gly, Ala/Thr, Ser/Asn, Ala/Val, Ser/Gly, Thr/Phe, Ala/Pro, Lys/Arg, Asp/Asn, Leu/Ile, Leu/Val, Ala/Glu, Asp/Gly, in both directions, but are not limited thereto. The protein, if desired, may be modified by phosphorylation, sulfation, acrylation, glycosylation, methylation, farnesylation, etc. In addition, the protein variants may include a protein which has increased structural stability against heat, pH, etc. or has increased activity by alteration or modification of the amino acid sequence.

Further, the herbicide-resistant PPO protein may be a variant which has a biological activity equivalent to that of the polypeptide comprising, consisting essentially of, or consisting of the amino acid sequence of SEQ ID NO: 1, SEQ ID NO: 3, SEQ ID NO: 5, or SEQ ID NO: 7. The variant may include substitution, deletion, addition, and/or insertion of amino acids, compared to a wild type or benchmark reference protein, and has a biological activity similar or equivalent to that of the wild type or benchmark reference protein. In this context, the term "sequence homology" refers to the degree of similarity to the wild-type or reference amino acid sequence or nucleotide sequence. Any protein may be included in the scope of the present invention, as long as it includes amino acid residues having 60% or higher, 65% or higher, 70% or higher, 75% or higher, 80% or higher, 85% or higher, 90% or higher, 95% or higher, 98% or higher, or 99% or higher identity to the amino acid sequence of the herbicide-resistant PPO protein provided herein, and also retains a biological activity equivalent to the polypeptide comprising, consisting essentially of, or consisting of the amino acid sequence of SEQ ID NO: 1, SEQ ID NO: 3, SEQ ID NO: 5 or SEQ ID NO: 7. Such protein equivalent may include an active site equivalent to that of the desired protein. Homology comparisons may be conducted by eye or with the aid of readily available comparison programs. These commercially available computer programs may calculate percent (%) homology between two or more sequences, and homology (%) may be calculated over contiguous sequences. The sequence alignment for comparison may be conducted by methods known in the art, for example, GAP, BESTFIT, BLAST, FASTA and TFASTA.

Further, the herbicide-resistant PPO gene used in the disclosure may include a nucleic acid molecule including codons functionally equivalent to the nucleotide sequence of the gene encoding the corresponding polypeptide comprising, consisting essentially of, or consisting of the amino acid sequence of SEQ ID NO: 1, SEQ ID NO: 3, SEQ ID NO: 5 or SEQ ID NO: 7, or codons encoding the identical amino acids (by degeneration of codons), or codons encoding biologically equivalent amino acids. Further, the scope of the present invention may also include a nucleic acid molecule, which encodes a protein retaining an activity biologically equivalent to that of the herbicide-resistant PPO protein, and also includes nucleotides having at least 60% or higher, 65% or higher, 70% or higher, 75% or higher, 80% or higher, 85% or higher, 90% or higher, 95% or higher, 98% or higher, or 99% or higher identity thereto when the nucleotide sequence of the gene encoding the herbicide-resistant PPO protein provided herein and any other different nucleotide sequence are aligned for maximum matching, and the aligned sequences are analyzed using an algorithm generally used in the art.

In an exemplary embodiment, the herbicide-resistant PPO protein provided herein includes one or more polypeptides selected from the group consisting of a polypeptide comprising, consisting essentially of, or consisting of an amino acid sequence of SEQ ID NO: 1 or an amino acid sequence having 95% or 98% or higher homology thereto; a polypeptide comprising, consisting essentially of, or consisting of an amino acid sequence of SEQ ID NO: 3 or an amino acid sequence having 95% or 98% or higher homology thereto; a polypeptide comprising, consisting essentially of, or consisting of an amino acid sequence of SEQ ID NO: 5 or an amino acid sequence having 95% or 98% or higher homology thereto; a polypeptide comprising, consisting essentially of, or consisting of an amino acid sequence of SEQ ID NO: 7 or an amino acid sequence having 95% or 98% or higher homology thereto; and any combinations thereof.

Further, the herbicide-resistant PPO gene includes one or more genes selected from the group consisting of a gene encoding the corresponding polypeptide comprising, consisting essentially of, or consisting of the amino acid sequence of SEQ ID NO: 1 or the amino acid sequence having 95% or 98% or higher homology thereto; a gene encoding the corresponding polypeptide comprising, consisting essentially of, or consisting of the amino acid sequence of SEQ ID NO: 3 or the amino acid sequence having 95% or 98% or higher homology thereto; a gene encoding the corresponding polypeptide comprising, consisting essentially of, or consisting of the amino acid sequence of SEQ ID NO: 5 or the amino acid sequence having 95% or 98% or higher homology thereto; a gene encoding the corresponding polypeptide comprising, consisting essentially of, or consisting of the amino acid sequence of SEQ ID NO: 7 or the amino acid sequence having 95% or 98% or higher homology thereto; and any combinations thereof.

The gene may be, for example, a gene comprising, consisting essentially of, or consisting of a nucleotide sequence of SEQ ID NO: 2 or a nucleotide sequence having 95% or 98% or higher homology thereto, a gene comprising, consisting essentially of, or consisting of a nucleotide sequence of SEQ ID NO: 4 or a nucleotide sequence having 95% or 98% or higher homology thereto, a gene comprising, consisting essentially of, or consisting of a nucleotide sequence of SEQ ID NO: 6 or a nucleotide sequence having 95% or 98% or higher homology thereto, a gene comprising, consisting essentially of, or consisting of a nucleotide sequence of SEQ ID NO: 8 or a nucleotide sequence having 95% or 98% or higher homology thereto, and/or any combinations thereof, but is not limited thereto.

The herbicide-resistant PPO protein may be obtained from a natural source by extraction and purification using methods widely known in the art. Alternatively, it may be obtained as a synthetic protein prepared by chemical synthesis, or as a recombinant protein prepared by a genetic recombination technology. When chemically synthesized, the protein may be obtained by a polypeptide synthesis method widely known in the art. When the genetic recombination technology is used, the nucleic acid encoding the herbicide-resistant PPO protein is inserted into a proper expression vector, this vector is transformed into a host cell, the host cell is cultured to express the desired protein, and then the herbicide-resistant PPO protein is recovered from the host cell. After the protein is expressed in a selected host cell, general biochemical separation techniques, for example, treatment with a protein precipitating agent (salting out), centrifugation, ultrasonic disruption, ultrafiltration, dialysis, chromatography such as molecular sieve chromatography (gel filtration), adsorption chromatography, ion exchange chromatography, affinity chromatography and the like may be used for the isolation and purification thereof. Generally, in order to separate the protein with a high purity, these methods may be used in combination.

The herbicide-resistant PPO nucleic acid molecule may be isolated or prepared using standard molecular biological techniques, for example, a chemical synthesis or recombination method. Alternatively, commercially available one may be used.

In a specific embodiment, the PPO proteins were found to exhibit a broad herbicide resistance against representative 9 families of PPO activity-inhibiting herbicides classified according to their chemical structures in an herbicide resistance test system using PPO-deficient *E. coli* BT3(ΔPPO). It was also found that the proteins may be expressed in tobacco leaves by *Agrobacterium*-mediated transformation, and they may be also expressed in the chloroplast of a plant by using a transit peptide (TP). Further, it was found that the PPO proteins may be also expressed in *Arabidopsis thaliana* (ecotype Columbia) by a plant expression vector. Even though the transformed plants are treated with PPO activity-inhibiting herbicides, germination and growth of the plants are observed. Furthermore, inheritance of the above herbicide-resistant traits to the next generation was confirmed by an inheritance study.

Therefore, the PPO protein provided herein may be introduced into a plant or an alga, thereby being used for enhancement of the herbicide resistance of the plant or the alga.

As used herein, the "herbicide" refers to an active ingredient that kills, controls or otherwise adversely modifies the growth of plants or algae. As used herein, the "herbicide tolerance" or "herbicide resistance" means that even after treatment of a herbicide which normally kills a normal or wild-type plant or alga or normally inhibits growth thereof, inhibition of the plant or alga growth is weakened or eliminated, compared to that of the normal or wild-type plant or alga, and therefore, the plant or the alga continues to grow. The herbicide includes an herbicide inhibiting protoporphyrinogen oxidase (PPO) of a plant. Such PPO-inhibiting herbicide may be classified into pyrimidinediones, diphenyl-ethers, phenylpyrazoles, N-phenylphthalimides, thiadiazoles, oxadiazoles, triazolinones, oxazolidinediones, and other herbicides according to their chemical structures.

In an exemplary embodiment, the pyrimidinedione-based herbicide includes butafenacil, saflufenacil, benzfendizone, and tiafenacil, but is not limited thereto.

The diphenyl-ether-based herbicide includes fomesafen, oxyfluorfen, aclonifen, acifluorfen, bifenox, ethoxyfen, lactofen, chlomethoxyfen, chlorintrofen, fluoroglycofen-ethyl, and halosafen, but is not limited thereto.

The phenylpyrazole-based herbicide includes pyraflufen-ethyl and fluazolate, but is not limited thereto.

The phenylphthalimide-based herbicide includes flumioxazin, cinidon-ethyl, and flumiclorac-pentyl, but is not limited thereto.

The thiadiazole-based herbicide includes fluthiacet and thidiazimin, but is not limited thereto.

The oxadiazole-based herbicide includes oxadiargyl and oxadiazon, but is not limited thereto.

The triazolinone-based herbicide includes carfentrazone, sulfentrazone, and azafenidin, but is not limited thereto.

The oxazolidinedione-based herbicide includes pentoxazone, but is not limited thereto.

Other herbicides include pyraclonil, flufenpyr-ethyl and profluazol, but is not limited thereto.

The herbicide-resistant PPO gene provided herein may be introduced into the plant or the algae by various methods known in the art, and preferably, by using an expression vector for plant or algae transformation.

An appropriate promoter which may be included in the vector may be any promoter generally used in the art for introduction of the gene into the plant or the alga. For example, the promoter for plant transformation may include an SP6 promoter, a T7 promoter, a T3 promoter, a PM promoter, a maize ubiquitin promoter, a cauliflower mosaic virus (CaMV) 35S promoter, a nopaline synthase(nos) promoter, a figwort mosaic virus 35S promoter, a sugarcane bacilliform virus promoter, a *commelina* yellow mottle virus promoter, a light-inducible promoter from the small subunit of ribulose-1,5-bisphosphate carboxylase (ssRUBISCO), a rice cytosolic triosephosphate isomerase (TPI) promoter, an adenine phosphoribosyltransferae (APRT) promoter of *Arabidopsis*, an octopine synthase promoter, and a BCB (blue copper binding protein) promoter, but is not limited thereto. Further, the vector for plant transformation may include a poly A signal sequence causing polyadenylation of 3'-terminus, and for example, it may include NOS 3'-end derived from a nopaline synthase gene of *Agrobacterium tumefaciens*, an octopine synthase terminator derived from an octopine synthase gene of *Agrobacterium tumefaciens*, 3'-end of protease inhibitor I or II gene of tomato or potato, a CaMV 35S terminator, a rice α-amylase terminator RAmyl A, and a phaseoline terminator, but is not limited thereto.

Further, the promoter for algae transformation may be a chloroplast specific promoter, a nuclear promoter, a constitutive promoter or an inducible promoter. The the gene encoding the herbicide-resistant PPO gene provided herein may be operably linked to a 5' UTR or 3' UTR that functions in the nucleus of the alga. Further, the vector for algae transformation may include a transcriptional regulatory sequence for expression of the gene in the nucleus of the alga. A recombinant gene conferring herbicide resistance may be integrated into the nuclear genome or chloroplast genome of a host alga.

In the vector, a transit peptide required for targeting to chloroplasts may be linked to 5'-end of the PPO gene in order to express the herbicide-resistant PPO gene in the chloroplasts.

Optionally, the vector may further include a gene encoding selectable marker as a reporter molecule, and example of the selectable marker may include antibiotics (e.g., neomycin, carbenicillin, kanamycin, spectinomycin, hygromycin, bleomycin, chloramphenicol, etc.) or herbicide (glyphosate, glufosinate, phosphinothricin, etc.)-resistant genes, but is not limited thereto.

Further, the recombinant vector for plant expression may include an *Agrobacterium* binary vector, a cointegration vector, or a general vector which has no T-DNA region but is designed to be expressed in the plant. Of them, the binary vector refers to a vector containing two separate vector systems harboring one plasmid responsible for migration consisting of left border (LB) and right border (RB) in Ti (tumor inducible) plasmid, and the other plasmid for target gene-transferring, and the vector may include a promoter region and a polyadenylation signal sequence for expression in plants.

When the binary vector or cointegration vector is used, a strain for transformation of the recombinant vector into the plant is preferably *Agrobacterium* (*Agrobacterium*-mediated transformation). In this regard, *Agrobacterium tumefaciens* or *Agrobacterium rhizogenes* may be used. In addition, when the vector having no T-DNA region is used, electroporation, microparticle bombardment, polyethylene glycol-mediated uptake, etc. may be used for introduction of the recombinant plasmid into the plant.

The plant transformed with the gene by the above method may be re-differentiated into a plant through callus induction, rhizogenesis, and soil acclimatization using a standard technique known in the art.

The plant subjected to transformation herein is understood by a meaning including a plant cell (containing a suspension-cultured cell), a protoplast, a callus, a hypocotyl, a seed, a cotyledon, a shoot as well as a mature plant.

Further, the scope of the transformant includes a transformant introduced with the gene as well as a clone or progeny thereof (T1 generation, T2 generation, or any subsequent generations). For example, the transformed plant also includes a plant having the inherited herbicide resistance traits as sexual and asexual progeny of the plant transformed with the gene provided herein. The scope of the present invention also includes all mutants and variants showing the characteristics of the initial transformed plant, together with all hybridization and fusion products of the plant transformed with the gene provided herein. Furthermore, the scope of the present invention also includes a part of the plant, such as a seed, a flower, a stem, a fruit, a leaf, a root, a tuber, a tuberous root, which is originated from a transformed plant which is transformed in advance by the method of the present invention, or a progeny thereof, and is composed of at least a part of the transformed cells.

The plant, to which the present invention is applied, is not particularly limited to, but includes monocotyledonous or dicotyledonous plants. Further, the plant includes herbaceous plants or woody plants. The monocotyledonous plant may include plants belonging to the family Alismataceae, Hydrocharitaceae, Juncaginaceae, Scheuchzeriaceae, Potamogetonaceae, Najadaceae, Zosteraceae, Liliaceae, Haemodoraceae, Agavaceae, Amaryllidaceae, Dioscoreaceae, Pontederiaceae, Iridaceae, Burmanniaceae, Juncaceae, Commelinaceae, Eriocaulaceae, Gramineae Poaceae, Araceae, Lemnaceae, Sparganiaceae, Typhaceae, Cyperaceae, Musaceae, Zingiberaceae, Cannaceae, Orchidaceae, but is not limited thereto.

The dicotyledonous plant may include plants belonging to the family Diapensiaceae, Clethraceae, Pyrolaceae, Ericaceae, Myrsinaceae, Primulaceae, Plumbaginaceae, Ebenaceae, Styracaceae, Symplocaceae, Symplocaceae, Oleaceae, Loganiaceae, Gentianaceae, Menyanthaceae, Apocynaceae, Asclepiadaceae, Rubiaceae, Polemoniaceae, Convolvulaceae, Boraginaceae, Verbenaceae, Labiatae, Solanaceae, Scrophulariaceae, Bignoniaceae, Acanthaceae, Pedaliaceae, Orobanchaceae, Gesneriaceae, Lentibulariaceae, Phrymaceae, Plantaginaceae, Caprifoliaceae, Adoxaceae, Valerianaceae, Dipsacaceae, Campanulaceae, Compositae, Myricaceae, Juglandaceae, Salicaceae, Betulaceae, Fagaceae, Ulmaceae, Moraceae, Urticaceae, Santalaceae, Loranthaceae, Polygonaceae, Phytolaccaceae, Nyctaginaceae, Aizoaceae, Portulacaceae, Caryophyllaceae, Chenopodiaceae, Amaranthaceae, Cactaceae, Magnoliaceae, Illiciaceae, Lauraceae, Cercidiphyllaceae, Ranunculaceae, Berberidaceae, Lardizabalaceae, Meni spermaceae, Nymphaeaceae, Ceratophyllaceae, Cabombaceae, Saururaceae, Piperaceae, Chloranthaceae, Aristolochiaceae, Actinidiaceae, Theaceae, Guttiferae, Droseraceae, Papaveraceae, Capparidaceae, Cruciferae, Platanaceae, Hamamelidaceae, Crassulaceae, Saxifragaceae, Eucommiaceae, Pittosporaceae, Rosaceae, Leguminosae, Oxalidaceae, Geraniaceae, Tropaeolaceae, Zygophyllaceae, Linaceae, Euphorbiaceae, Callitrichaceae, Rutaceae, Simaroubaceae, Meliaceae, Polygalaceae, Anacardiaceae, Aceraceae, Sapindaceae, Hippocastanaceae, Sabiaceae, Balsaminaceae, Aquifoliaceae, Celastraceae, Staphyleaceae, Buxaceae, Empetraceae, Rhamnaceae, Vitaceae, Elaeocarpaceae, Tiliaceae, Malvaceae, Sterculiaceae, Thymelaeaceae, Elaeagnaceae, Flacourtiaceae, Violaceae, Passifloraceae, Tamaricaceae, Elatinaceae, Begoniaceae, Cucurbitaceae, Lythraceae, Punicaceae, Onagraceae, Haloragaceae, Alangiaceae, Cornaceae, Araliaceae, Umbelliferae(Apiaceae), but is not limited thereto.

In an exemplary embodiment, the plant includes food crops such as rice, wheat, barley, corn, soybean, potato, wheat, red bean, oat, and sorghum; vegetable crops such as *Arabidopsis thaliana*, Chinese cabbage, radish, red pepper, strawberry, tomato, watermelon, cucumber, cabbage, oriental melon, pumpkin, welsh onion, onion, and carrot; crops for special use such as *ginseng*, tobacco, cotton, soilage, forage, sesame, sugar cane, sugar beet, *Perilla* sp., peanut, rape, grass, and castor-oil plant; fruit trees such as apple tree, pear tree, jujube tree, peach tree, kiwi fruit tree, grape tree, citrus fruit tree, persimmon tree, plum tree, apricot tree and banana tree; woody plants such as pine, palm oil, and *eucalyptus*; flowering crops such as rose, *gladiolus*, *gerbera*, carnation, *chrysanthemum*, lily and tulip; and fodder crops such as ryegrass, red clover, orchardgrass, alfalfa, tall fescue and perennial ryograss, but is not limited thereto. Specific examples of the plant may include dicotyledonous plants such as *Arabidopsis thaliana*, potato, eggplant, tobacco, red pepper, tomato, burdock, crown daisy, lettuce, balloon flower, spinach, chard, sweet potato, celery, carrot, water dropwort, parsley, Chinese cabbage, cabbage, radish, watermelon, oriental melon, cucumber, pumpkin, gourd, strawberry, soybean, mung beans, kidney bean, and pea, but are not limited thereto.

The alga, to which the present invention is applied, is particularly limited to, but includes prokaryotic alga or eukaryotic alga. In some embodiments, the alga can be cyanobactera, green algae, red algae, brown algae, macroalgae or microalgae.

The cyanobacterium can be of the phyla Chroococcales (including Aphanocapsa, Aphanotece, Chamaesiphon, Chondrocystis, Chroococcus, Chroogloeocystis, Crocosphaera, Cyanobacterium, Cyanobium, Cyanodictyon, Cyanosarcina, Cyanothece, Dactylococcopsis, Gloeocapsa, Gloeothece, *Halothece*, Johannesbaptistia, Merismopedia, Microcystis, Radiocystis, Rhabdoderma, Snowella, Synechococcus, *Synechocystis, Thermosynechococcus*, Woronichinia), Gloeobacteria, Nostocales (including Microchaetaceae, Nostocaceae, Rivulariaceae, Scytonemataceae), Oscillatoriales (including Arthronema, Arthrospira, Blennothrix, Crinalium, Geitlerinema, Halomicronema, Halospirulina, Hydrocoleum, Jaaginema, Katagnymene, Komvophoron, Leptolyngbya, Limnothrix, *Lyngbya, Microcoleus, Oscillatoria*, Phormidium, Planktothricoides, Planktothrix, Plectonema, Pseudanabaena, Pseudophormidium, Schizothrix, *Spirulina*, Starria, Symploca, *Trichodesmium*, Tychonema), Pleurocapsales (including Chroococcidiopsis, Dermocarpa, Dermocarpella, Myxosarcina, Pleurocapsa, Solentia, Stanieria, Xenococcus), Prochlorales, or Stigonematales (including Capsosira, Chlorogloeopsis, Fischerella, Hapalosiphon, Mastigocladopsis, Mastigocladus, Nostochopsis, Stigonema, Symphyonema, Symphonemopsis, Umezakia, Westiellopsis).

The alga may further comprise a species of the Chlorophyta, *Chlamydomonas, Volvacales, Dunaliella, Scenedesmus, Chlorella*, or *Hematococcm*.

The alga may further comprise *Phaeodactylum tricornutum, Amphiprora hyaline, Amphora* spp., *Chaetoceros muelleri, Navicula saprophila, Nitzschia communis, Scenedesmus dimorphus, Scenedesmus obliquus, Tetraselmis suecica, Chlamydomonas reinhardtii, Chlorella vulgaris, Haematococcus pluvialis, Neochloris oleoabundans, Synechococcus elongatus, Botryococcus braunii, Gloeobacter violaceus, Synechocystis, Thermosynechococcus elongatus, Nannochloropsis oculata, Nannochloropsis sauna, Nannochloropsis gaditana, Isochrysis galbana, Botryococcus sudeticus, Euglena gracilis, Neochloris oleoabundans, Nitzschia palea, Pleurochrysis carterae, Tetraselmis chuii, Pavlova* spp., *Aphanocapsa* spp., *Synechosystis* spp. *Nannochloris* spp. It is however, clear for one skilled in the art that this list is not exclusive, but that various other genera and species can be used as well.

The plant or alga introduced with the herbicide-resistant PPO provided herein may exhibit resistance against two or more of PPO-inhibiting herbicides.

In an exemplary embodiment, therefore, two or more of PPO-inhibiting herbicides may be used sequentially or simultaneously to control weeds and/or undesired aquatic species.

For example, there are provided methods of controlling weeds in a cropland, the method including providing the cropland with a plant including the herbicide-resistant PPO protein or the gene encoding the corresponding peptides, and then applying two or more of the protoporphyrinogen oxidase-inhibiting herbicides to the cropland at an effective dosage sequentially or simultaneously.

Further, there are provided methods of controlling undesired aquatic species in a cultivation medium, the method including providing the cultivation medium with an alga including the herbicide-resistant PPO protein or the gene encoding the corresponding peptides, and then applying two or more of the protoporphyrinogen oxidase-inhibiting herbicides to the cultivation medium at an effective dosage sequentially or simultaneously.

Further, the herbicide-resistant PPO protein or gene provided herein may be used in combination of a second herbicide-resistant polypeptide or a gene encoding the corresponding peptides.

Therefore, the plant or alga introduced with the herbicide-resistant PPO provided herein may exhibit resistance against two or more of herbicides which are different from each other in mechanism of action. In the present invention, two or more of different herbicides including the PPO-inhibiting herbicide, which are different from each other in mechanism of action, may be used sequentially or simultaneously, thereby controlling weeds and/or undesired aquatic species. Hereinafter, the herbicide which is different from the PPO-inhibiting herbicide in the mechanism of action is called "second herbicide".

For example, there are provided peptide or nucleotide composition for conferring or/and enhancing herbicide resistance on a plant or an alga, the composition including the above described herbicide-resistant PPO protein or a gene encoding the corresponding peptide; and the second herbicide-resistant polypeptide or gene encoding the corresponding peptide.

Further, there are provided a transformant, or a clone or progeny thereof having novel or/and enhanced herbicide resistance, the transformant, or the clone or progeny thereof including the above described herbicide-resistant PPO protein or a gene encoding the corresponding peptide; and the second herbicide-resistant polypeptide or a gene encoding the corresponding peptide.

Further, there are provided methods of preparing a plant or an alga having novel or/and enhanced herbicide resistance, the method including transforming an alga, a plant cell, protoplast, callus, hypocotyl, seed, cotyledon, shoot or plant with the above described herbicide-resistant PPO protein or a gene encoding the corresponding peptide; and the second herbicide-resistant polypeptide or a gene encoding the corresponding peptide.

Further, there are provided methods of controlling weeds in a cropland, the method including providing a cropland with the plant including the above described herbicide-resistant PPO protein or a gene encoding the corresponding peptide; and the second herbicide-resistant polypeptide or a gene encoding the corresponding peptide, and applying the protoporphyrinogen oxidase-inhibiting herbicide and the second herbicide to the cropland at an effective dosage thereof, sequentially or simultaneously.

Further, there are provided methods of controlling undesired aquatic species in a cultivation medium, the method including providing a cultivation medium with the alga including the above described herbicide-resistant PPO protein or a gene encoding the corresponding peptide; and the second herbicide-resistant polypeptide or a gene encoding the corresponding peptide, and applying the protoporphyrinogen oxidase-inhibiting herbicide and the second herbicide to the cultivation medium at an effective dosage thereof, sequentially or simultaneously.

In an exemplary embodiment, the plant or the alga may further include the second herbicide-resistant polypeptide or a gene encoding the corresponding peptide, thereby having novel or/and enhanced resistance against the second herbicide.

In another exemplary embodiment, the second herbicide may include cell division-inhibiting herbicides, photosynthesis-inhibiting herbicides, amino acid synthesis-inhibiting herbicides, plastid-inhibiting herbicides, cell membrane-inhibiting herbicides, and/or any combinations thereof, but is not limited thereto. The second herbicide may be exemplified by glyphosate, glufosinate, dicamba, 2,4-D(2,4-Dichlorophenoxyacetic acid), ALS (acetolactate synthase)-inhibiting herbicides (e.g., imidazolidinone, sulfonylurea, triazole pyrimidine, sulphonanilide, pyrimidine thiobenzoate, etc.), photosystem II-inhibiting herbicides, phenylure-based herbicides, plastid-inhibiting, herbicides, bromoxynil-based herbicides, and/or any combinations thereof, but is not limited thereto.

In still another exemplary embodiment, the second herbicide-resistant polypeptide may be exemplified selected from the group consisting of glyphosate herbicide-resistant EPSPS (glyphosate resistant 5-enolpyruvylshikimate-3-phosphate synthase), GOX (glyphosate oxidase), GAT (glyphosate-N-acetyltransferase) or glyphosate decarboxylase; glufosinate herbicide-resistant PAT(phosphinothricin-N-acetyltransferase); dicamba herbicide-resistant DMO (monooxygenase); 2,4-D herbicide-resistant 2,4-D monooxygenase or AAD(aryloxyalkanoate Dioxygenase); ALS-inhibiting sulfonylurea-based herbicide-resistant ALS (Acetolactate Synthase), AHAS (acetohydroxyacid synthase), or AtAHASL (Acetohydroxyacid synthase Large Subunit); photosystem II-inhibiting herbicide-resistant photosystem II protein D1; phenylurea-based herbicide-resistant cytochrome P450; plastid-inhibiting herbicide-resistant HPPD(Hydroxylphenylpyruvate dioxygenase); bromoxynil herbicide-resistant nitrilase; and any combinations thereof, but is not limited thereto.

Further, the gene encoding the second herbicide-resistant polypeptide may be exemplified selected from the group consisting of glyphosate herbicide-resistant CP4 EPSPS, EPSPS(AG), MEPSPS, 2MEPSPS, GOXV247, GAT4601 or GAT4621 gene; glufosinate herbicide-resistant BAR, PAT or PAT(SYN) gene; dicamba herbicide-resistant DMO gene; 2,4-D herbicide-resistant AAD-1 or AAD-12 gene; ALS-inhibiting sulfonylurea-based herbicide-resistant ALS, GM-HRA, S4-HRA, ZM-HRA, CSR1, CSR1-1, CSR1-2, SURA or SURB; photosystem II-inhibiting herbicide-resistant PSBA gene; phenylurea herbicide-resistant CYP76B1 gene; isoxaflutole herbicide-resistant HPPDPF W336 gene; bromoxynil herbicide-resistant BXN gene; and any combinations thereof, but is not limited thereto.

This invention may be embodied in many different forms, and should not be construed as limited to the embodiments set forth herein. Rather, these embodiments are provided so that this disclosure will be thorough and complete, and will fully convey the scope of the invention to those skilled in the art. Like reference numerals refer to like elements throughout.

It will be understood that, although the terms "first," "second," "third" etc. may be used herein to describe various elements or components, these elements or components should not be limited by these terms. These terms are only used to distinguish one element or component from another element or component.

The terminology used herein is for the purpose of describing particular embodiments only and is not intended to be limiting. As used herein, the singular forms "a," "an" and "the" are intended to include the plural forms as well, unless the context clearly indicates otherwise. It will be further understood that the terms "comprises" and/or "comprising," or "includes" and/or "including" when used in this specification, specify the presence of stated features, elements, and/or components, but do not preclude the presence or addition of one or more other features, elements or components, and/or groups thereof. As used herein, the term "and/or" includes any and all combinations of one or more of the associated listed items While the invention has been described in detail in connection with a number of embodiments, the invention is not limited to such disclosed embodiments. Rather, the invention can be modified to incorporate any number of variations, alterations, substitutions or equivalent arrangements not heretofore described, but which are commensurate with the scope of the invention.

Effect of the Invention

An herbicide-resistant PPO provided herein is applied to plants or algae including commercial crops, and then selective control is performed using herbicide resistance traits and herbicides, thereby economically controlling weeds.

DETAILED DESCRIPTION OF THE EMBODIMENTS

Hereinafter, the present invention will be described in detail with reference to Examples. However, these Examples are for illustrative purposes only, and the invention is not intended to be limited by these Examples.

Example 1. Isolation of PPO Gene from Prokaryote

*Oscillatoria nigro-viridis* PCC 7112, *Lyngbya* sp. PCC 8106 strain, and *Halothece* sp. PCC 7418 strain were provided by the Institut Pasteur, (France), and PPO genes were isolated therefrom by PCR using primers of Table 1. Genomic DNA was isolated from each strain, and PPO gene was isolated and amplified using the primers of Table 1. The sequence of the PPO gene of *Microcoleus vaginatus* (GenScript) was synthesized by codon usage optimization of *Arabidopsis thaliana* using Genbank database information and amplified using primers of Table 1. 50 µl of PCR reaction mixture was prepared by mixing 1 µl of each template (genomic DNA of each strain), 5 µl of 10× buffer, 2 µl of dNTP mixture (each 10 mM), 3 µl of a forward primer (10 µM), 3 µl of a reverse primer (10 µM), 35.5 µl of DDW, and 0.5 µl of Pfu-X (Solgent, 2.5 unit/µl) or EF-taq (Solgent, 2.5 u/µl), and amplification was performed under conditions of at 94° C. for 4 minutes, and 30 cycles (at 94° C. for 30 seconds, at 56° C. for 30 seconds and at 72° C. for 1.5 minutes), at 72° C. for 5 minutes and at 4° C. for 5 minutes. PPO isolated from *Oscillatoria nigro-viridis* PCC 7112 was designated as CyPPO2, PPO isolated from *Lyngbya* sp. PCC 8106 strain was designated as CyPPO4, PPO isolated from *Halothece* sp. PCC 7418 strain was designated as CyPPO8, and PPO isolated from *Microcoleus vaginatus* was designated as CyPPO12.

Further, respective amino acid sequences and nucleotide sequences of CyPPO2, CyPPO4, CyPPO8 and CyPPO12 were examined, and represented by SEQ ID NOS: 1 to 8, and in particular, the amino acid sequence of CyPPO2 showed 94% sequence homology to that of CyPPO12.

g of $MgCl_2.6\ H_2O$, 27.7 g of $MgSO_4.7\ H_2O$, 5.8 g of $CaCl_2.2\ H_2O$, and 1000 ml of distilled water. ASNIII medium and Tursk Island Salts 4× were autoclaved at 120° C. for 20 minutes, respectively and then mixed at a ratio of 1:1 (v/v).

Figure 1:
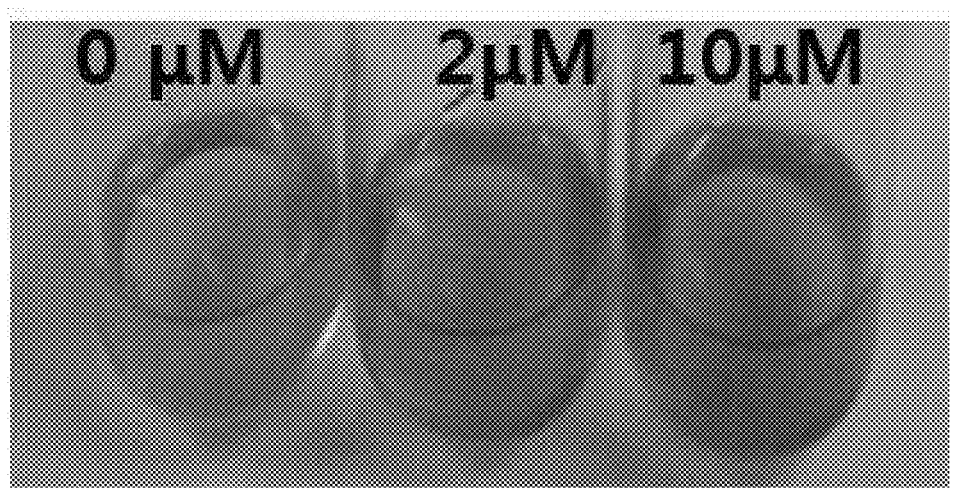
FIG. 1 is a photograph showing growth of *Halothece* sp. PCC 7418 strain which was cultured for 8 days in a CRBIP medium (Institut Pasteur, France) added without Tiafenacil or with 2 μM or 10 μM Tiafenacil.

5 ml of the above culture medium was added to a test tube, and 2 or 10 µM of Tiafenacil was added thereto or not. The seed-cultured *Halothece* sp. PCC 7418 strain was added to each test tube at an equal volume and growth of the strain was examined for 8 days. As a result, growth of *Halothece* sp. PCC 7418 strain was maintained even at 8 days after treatment of 10 µM of Tiafenacil, indicating that this strain has herbicide resistance (FIG. 1).

Example 3. Test of Herbicide Resistance of CyPPO2, CyPPO4, CyPPO8 and CyPPO12 in PPO-Deficient *E. coli* (Agar Medium)

To test herbicide resistance of CyPPO2, CyPPO4, CyPPO8 and CyPPO12 isolated in Example 1, PPO-deficient BT3 *E. coli* [hereinafter, referred to as BT3(ΔPPO)] was transformed with CyPPO2, CyPPO4, CyPPO8 or CyPPO12 gene, respectively and then cultured in the presence of herbicides to examine growth inhibition of the transformed *E. coli*. As a negative control, *Arabidopsis thaliana*-derived wild-type PPO (wild-type AtPPO1) was used, and wild-type AtPPO1 has sensitivity to PPO-based herbicides and its sequence information is available in

TABLE 1

| Strain | Primer | Sequence | SEQ ID NO: |
|---|---|---|---|
| *Oscillatoria nigro-viridis* PCC 7112 | PCC7112_BmHIF | ccccggatccATGGAACTATTAGATACCTTGATTGTGGG | 18 |
| | PCC7112_StuIR | cccaggcctGATCGATCGAGTATCTGATTG | 19 |
| *Halothece* sp. PCC 7418 | PCC7418_BmHIF | ccccggatccATGATAGATACTTTAATTGTGGG | 20 |
| | PCC7418_XhoIR | cccctcgagACCCAAATAATCTAACACGG | 21 |
| *Lyngbya* sp. PCC 8106 | PCC8106_BglIIF | cccagatctATGACTCACGTACTCGATAG | 22 |
| | PCC8106_XhoIR | cccctcgagTTGACCCAAAAAACTGAGAATTTC | 23 |
| *Microcoleus vaginatus* | CyPPO12_BamHIF | CCCCGGATCCATGGAACTCTTGGATACTCT | 24 |
| | CyPPO12_XhoIR | CCCCCTCGAGGATTGACCTGGTATCAGATT | 25 |

Example 2. Test of Herbicide Resistance of *Halothece* sp. PCC 7418 Strain

*Halothece* sp. PCC 7418 strain was cultured in CRBIP Medium 1538 (Institut Pasteur, France). CRBIP Medium 1538 is a mixed medium of ASNIII and Turks Island Salts 4× at a ratio of 1:1 (v/v), and ASNIII medium was composed of 25.0 g of NaCl, 3.5 g of $MgSO_4.7H_2O$, 2.0 g of $MgCl_2.6H_2O$, 0.5 g of KCl, 0.5 g of $CaCl_2.2H_2O$, 0.75 g of $NaNO_3$, 0.02 g of $K_2HPO_4.3H_2O$, 0.04 g of $NaCO_3$, 2.5 ml of ammonium iron (III) citrate/citric acid monohydrate solution [a mixture of 300 mg of ammonium iron (III) citrate, 300 mg of citric acid monohydrate, and 250 ml of distilled water], 2.5 ml of magnesium titriplex dihydrate solution [a mixture of 0.1 g of Mg EDTA and 500 ml of distilled water], 1 ml of trace metal A5+Co [a mixture of 2.86 g of $H_3BO_3$, 1.81 g of $MnCl_2.4H_2O$, 0.222 g of $ZnSO_4.7H_2O$, 0.39 g of $NaMoO_4.2H_2O$, 0.079 g of $CuSO_4.5H_2O$, 0.049 g of $Co(NO_3)_2.6H_2O$ and 1000 ml of distilled water], and 1000 ml of distilled water. Turks Island Salts 4× was composed of 112 g of NaCl, 2.68 g of KCl, 22

GeneBank accession no. AX084732 (a nucleotide sequence of the gene is represented by SEQ ID NO: 10, and an amino acid sequence thereof is represented by SEQ ID NO: 9). As a positive control, Mutant AtPPO1 was used, in which amino acid replacements of Y426M (replacement of tyrosine by methionine at position 426) and 5305L (replacement of serine by leucine at position 305) occur in the amino acid sequence of the wild-type AtPPO1 (an amino acid sequence is represented by SEQ ID NO: 11) (Li X, Volrath S L., N D B. G., Chilcott C E, Johnson M A, Ward E R, Law M D (2003) Development of protoporphyrinogen oxidase as an efficient selection marker for *Agrobacterium tumefaciens*-mediated transformation of maize. Plant physiology 133: 736-747).

BT3(ΔPPO) strain was provided by Hokkaido University (Japan) and it is an *E. coli* strain which is deficient in hemG-type PPO and has Kanamycin resistance (Watanabe et al., (2001) Dual targeting of spinach protoporphyrinogen oxidase II to mitochondria and chloroplasts by alternative use of two in-frame inhibition codons. JBC 20474~20481).

3-1. Preparation of Experimental Materials and Instruments

HVE-50 autoclave from Hirayama, HS2100A electronic scale from Hansung Instrument, CB-30V clean bench from Jeio Tech, JSI-200CL incubator from JSR, 1210 type UV-visible spectrophotometer from Thermo Fisher Scientific, MQ-200 photometer from Apogee, and Bio-Rad MyCycler as PCR machine were used. The autoclave was used under conditions of 121° C. and 15 minutes, and the incubator was used at 37° C. with lighting of 160~200 µmol m$^{-2}$ s$^{-1}$ for a culture time of 14~20 hours. LB medium (10 g/L of Bacto-Tryptone, 5 g/L of Yeast extract, 10 g/L of sodium chloride, 15 g/L of Bacto agar) and an antibiotic Chloramphenicol (Duchefa) were used. The herbicides used in the experiment are given in the following Table.

TABLE 2

| Chemical family | Herbicide (original name) | Manufacturer/Supplier |
|---|---|---|
| Pyrimidinedione | Tiafenacil | Dongbu Farm Hannong Co., Ltd./Dongbu Farm Hannong Co., Ltd. |
|  | Saflufenacil | BASF/Sigma |
|  | Butafenacil | Syngenta/Sigma |
| Diphenyl ether | Fomesafen | Syngenta/Sigma |
|  | Acifluorfen | United Phosphorus/Supelco |
|  | Oxyfluorfen | Dow/Sigma |
| N-phenylphthalimides | Flumioxazin | Sumitomo/Sigma |
| Triazolinones | Sulfentrazone | FMC/Waka |
| Oxazolidinediones | Pentoxazone | Kaken/Sigma |
| Phenylpyrazoles | Pyraflufen-ethyl | Nihon Nohyaky/Sigma |
| Others | Pyraclonil | Kyoyu Agri/Sigma |
| Oxadiazoles | Oxadiazon | Bayer/Sigma |
| Thiadiazoles | Fluthiacet-methyl | FMC/Sigma |

3-2. Experimental Method

Figure 2:
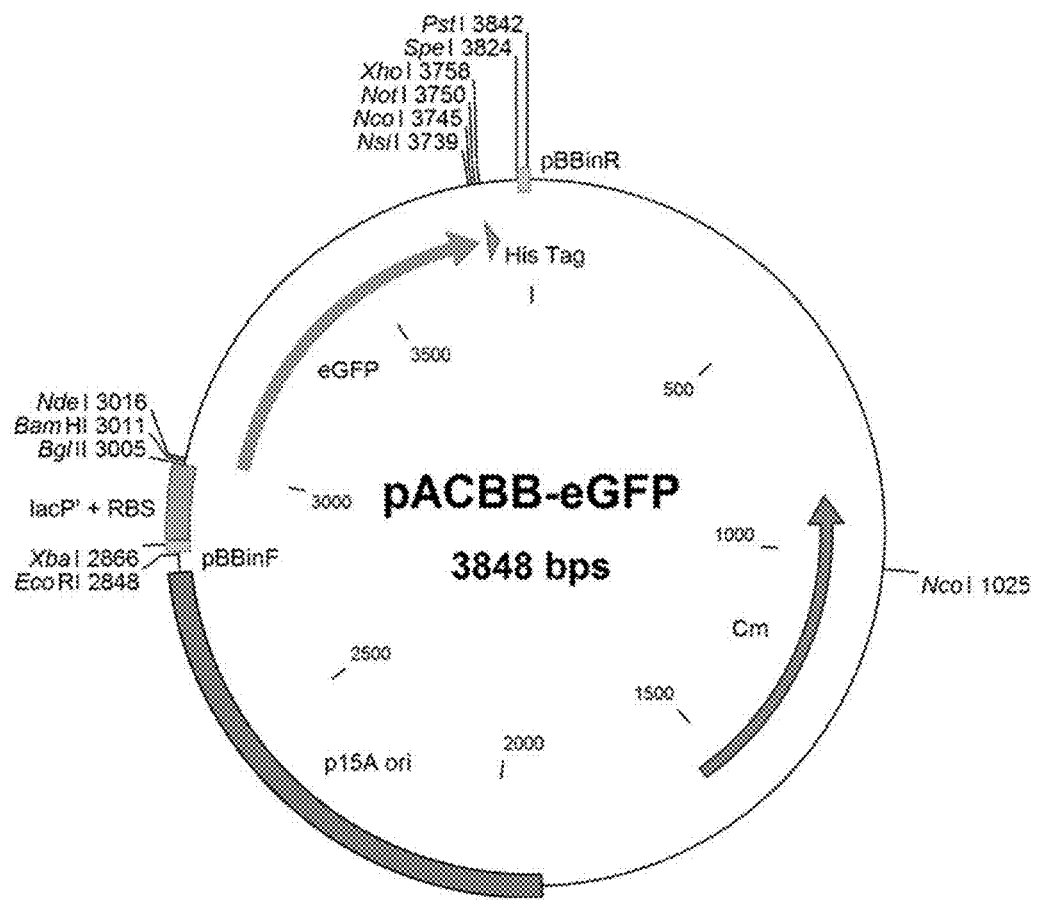
FIG. 2 shows a structure of pACBB vector used in *E. coli* BT3(ΔPPO) of the present invention. eGFP was removed before use, when each PPO gene was cloned into the vector.

To clone each of the CyPPO2, CyPPO4, CyPPO8 and CyPPO12 genes isolated and amplified in Example 1 into pACBB (its structure is shown in FIG. 2), 10 µl of a solution containing 4 µl of each PPO gene, 3.5 µl of pACBB vector, 1 µl of 10× buffer A, 1 µl of 10× buffer B, 1 µl of ligase (RBC, 3 unit/µl) was prepared and allowed to react at 22° C. for 30 minutes. The reaction solution was added to 100 µl of DH5 alpha competent cells, and allowed to react on ice for 20 minutes and then left at 42° C. for 40 seconds. Thereafter, the cells were left on ice for 2 minutes, and then 1 ml of LB broth was added thereto, followed by incubation with shaking at 37° C. for 1 hour. The strains having each gene insert in the culture medium were harvested, and then cultured on LB agar medium containing chloramphenicol.

For seed culture of *E. coli* transformed with respective genes, single colonies thereof were cultured in 3 ml of LB broth containing chloramphenicol overnight, and each 100 µl thereof was sub-cultured in 3 ml of fresh LB broth until absorbance (OD$_{600}$) reached 0.5~1. They were diluted with LB broth to absorbance (OD$_{600}$) of 0.5. 10-fold dilution of this diluted solution was performed with LB broth five times. Next, 10 µl of the diluted solution of the transformed *E. coli* culture was dropped on LB agar medium (petri dish) containing chloramphenicol and a variety of herbicide stocks at different concentrations (0~400 µM). The LB agar plates were incubated at 37° C. At 16~20 hours after culture, growth inhibition was examined with the naked eye. Further, growth inhibition of the strains cultured in a medium containing Tiafenacil was examined under light (lighting of 169 µmol m$^{-2}$ s$^{-1}$) and dark conditions.

3-3. Experimental Result

Figure 4:
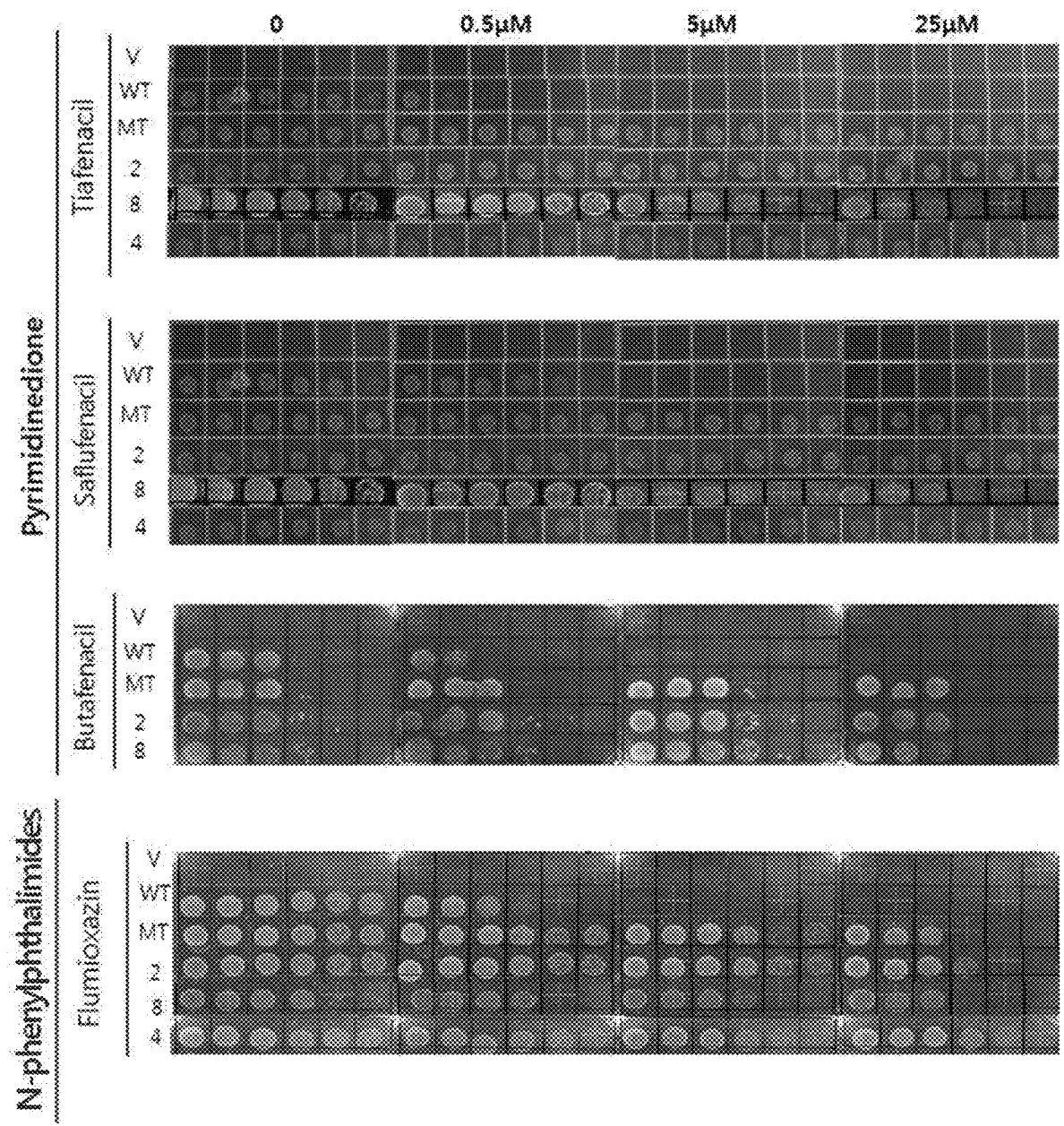
FIG. 4 is a photograph showing growth inhibition of respective BT3(ΔPPO) strains transformed with the wild-type AtPPO1 (indicated by WT), mutant AtPPO1 (indicated by MT), CyPPO2 (indicated by 2), CyPPO4 (indicated by 4) and CyPPO8 (indicated by 8) genes on agar medium containing 0~25 μM of a pyrimidinedione-based herbicide, Tiafenacil, Saflufenacil or Butafenacil, or an N-phenylphthalimide-based PPO herbicide, Flumioxazin. V indicates a strain prepared by transforming BT3(ΔPPO) with empty pACBB vector.
Figure 5:
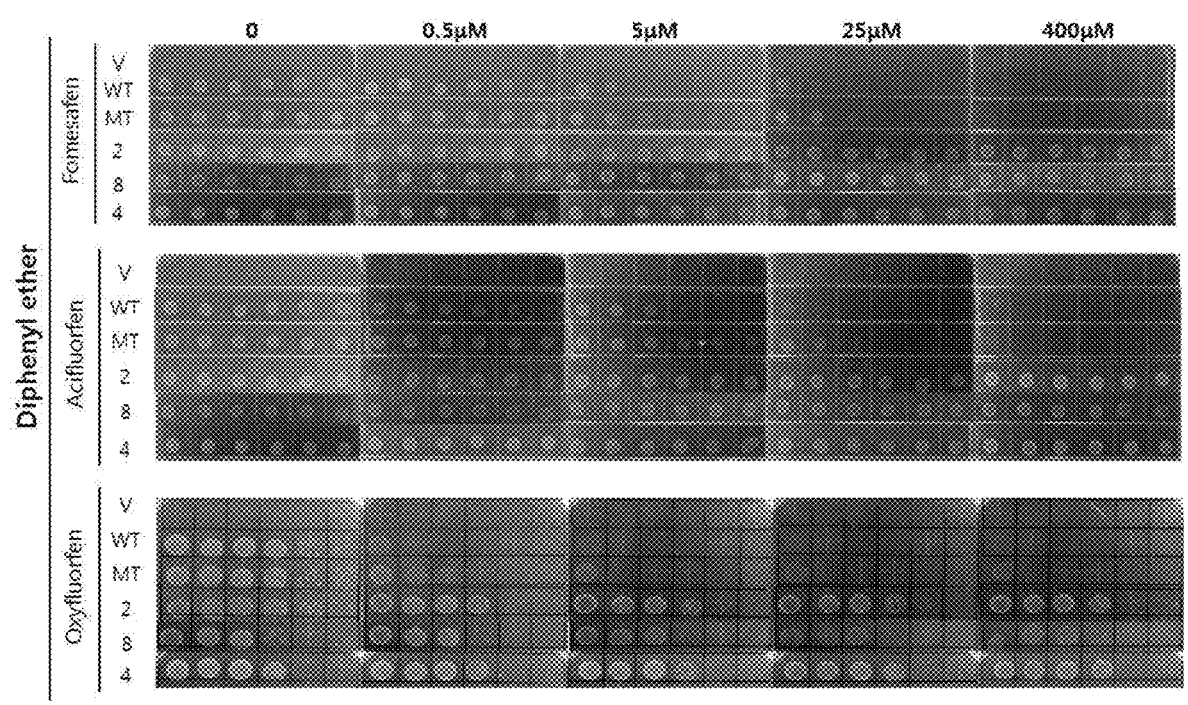
FIG. 5 is a photograph showing growth inhibition of respective BT3(ΔPPO) strains transformed with the wild-type AtPPO1 (indicated by WT), mutant AtPPO1 (indicated by MT), CyPPO2 (indicated by 2), CyPPO4 (indicated by 4) and CyPPO8 (indicated by 8) genes on agar medium containing 0~400 μM of a diphenyl ether-based PPO herbicide, Fomesafen, Acifluorfen or Oxyfluorfen. V indicates a strain prepared by transforming BT3(ΔPPO) with empty pACBB vector.
Figure 6:
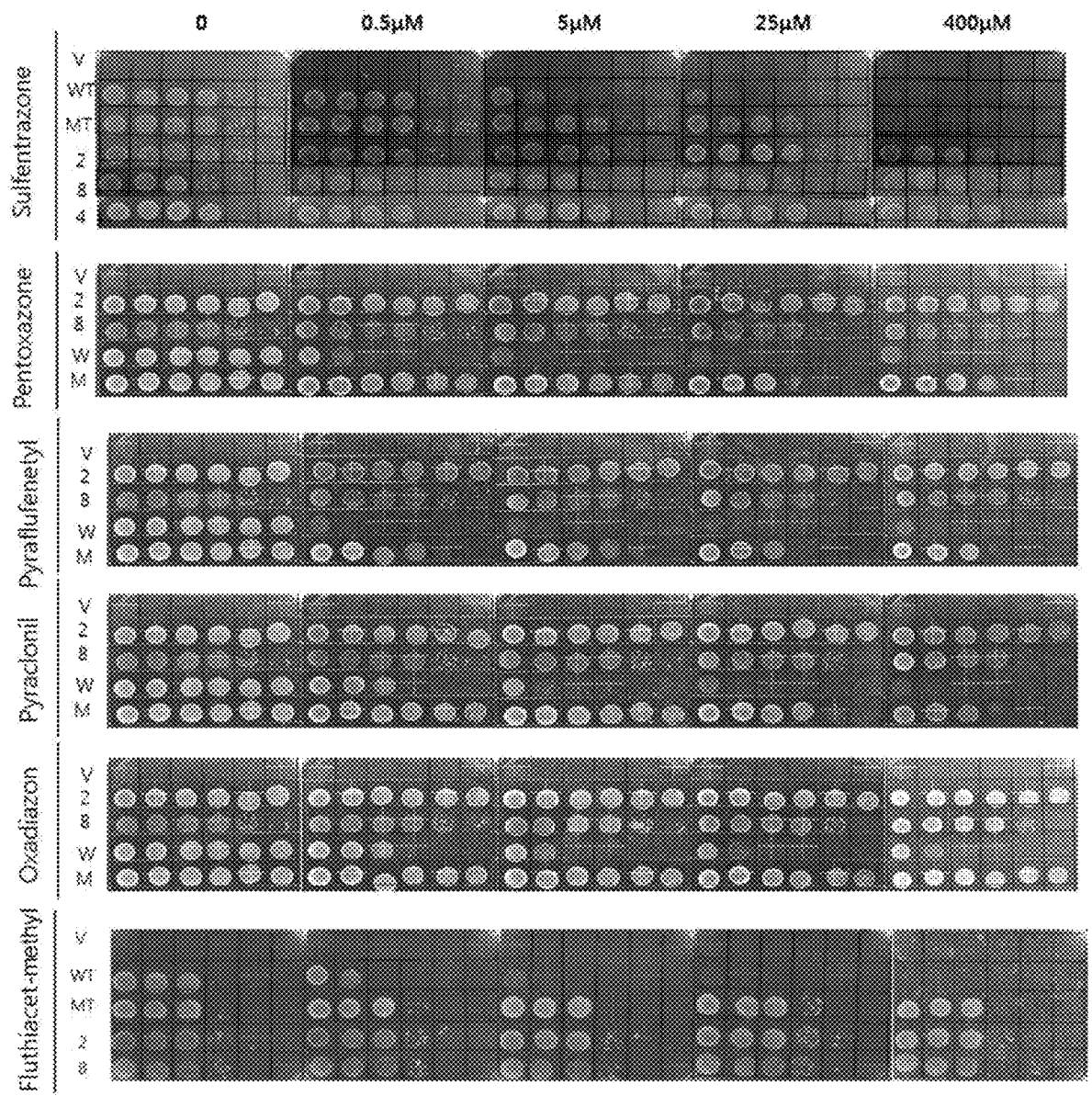
FIG. 6 is a photograph showing growth inhibition of respective BT3(ΔPPO) strains transformed with the wild-type AtPPO1 (indicated by WT), mutant AtPPO1 (indicated by MT), CyPPO2 (indicated by 2), CyPPO4 (indicated by 4) and CyPPO8 (indicated by 8) genes on agar medium containing 0~400 μM of a triazolinone-based PPO herbicide, Sulfentrazone, an oxizolidinedione-based PPO herbicide, Pentoxazone, a phenylpyrazole-based PPO herbicide, Pyraflufen-ethyl, an oxadiazole-based PPO herbicide, Oxadiazon, a thiadiazole-based PPO herbicide, Fluthiacet-methyl, or other PPO herbicide, Pyraclonil. V indicates a strain prepared by transforming BT3(ΔPPO) with empty pACBB vector.
Figure 7:
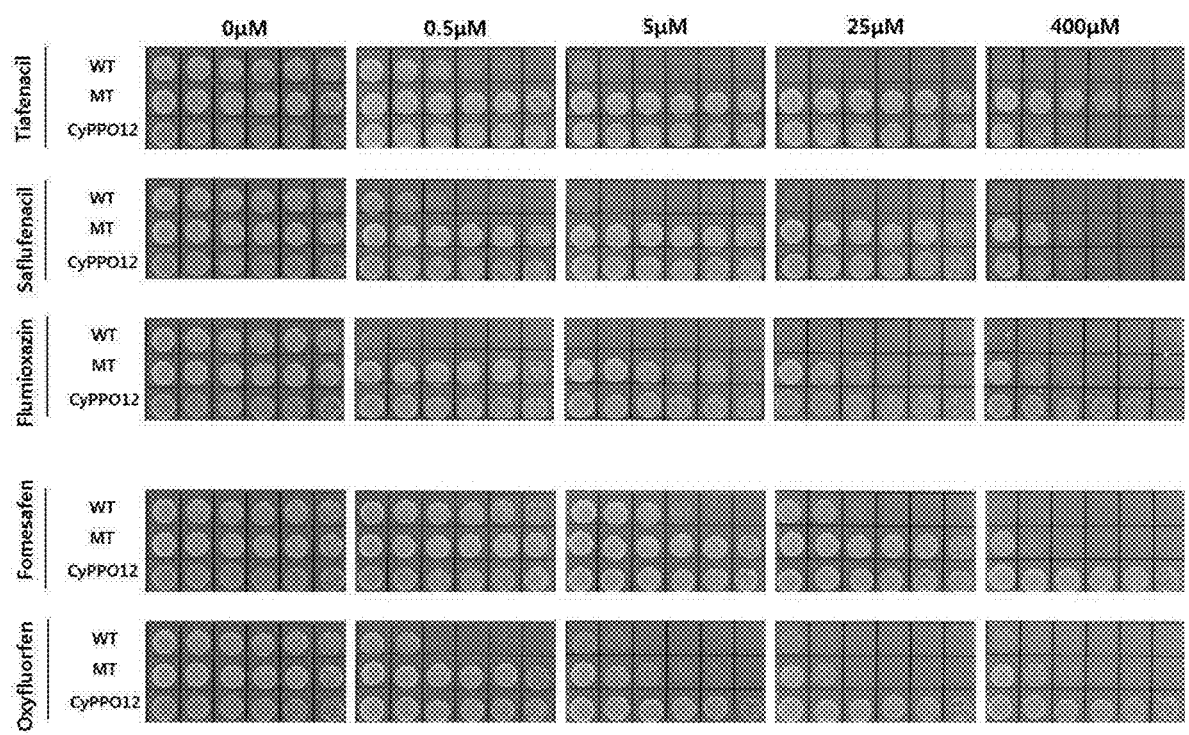
FIG. 7 is a photograph showing growth inhibition of respective BT3(ΔPPO) strains transformed with the wild-type AtPPO1 (indicated by WT), mutant AtPPO1 (indicated by MT), and CyPPO12 gene on agar medium containing 0~400 μM of Tiafenacil, Saflufenacil, Flumioxazin, Fomesafen or Oxyfluorfen.
Figure 8:
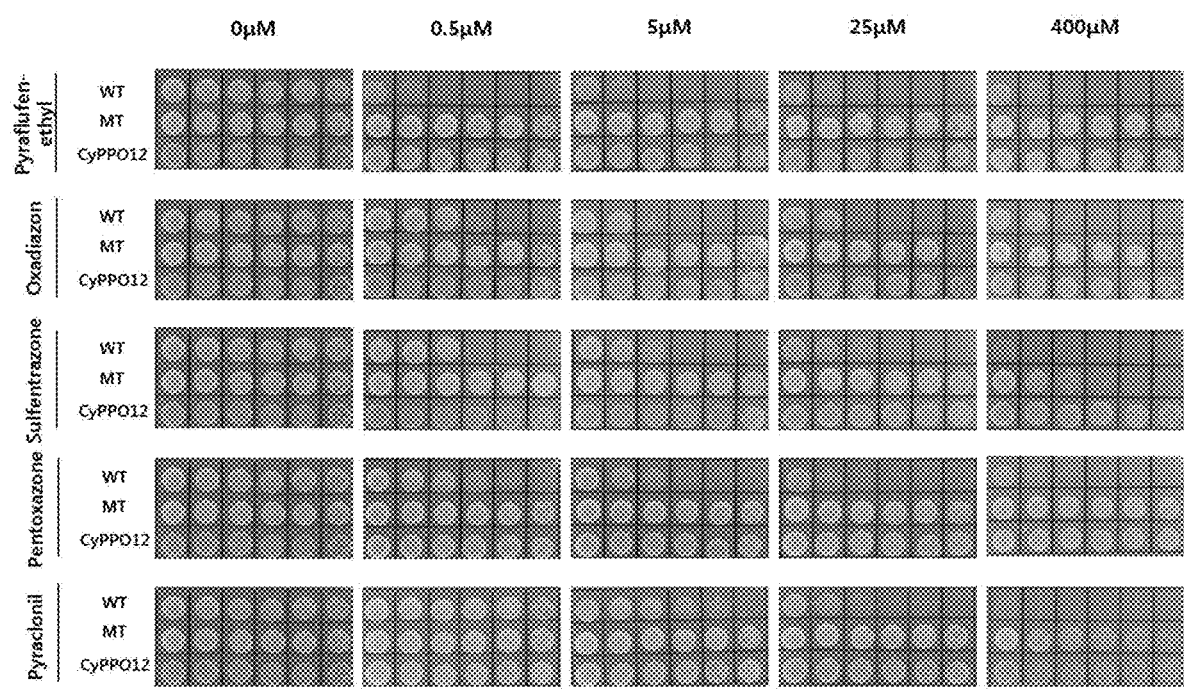
FIG. 8 is a photograph showing growth inhibition of respective BT3(ΔPPO) strains transformed with the wild-type AtPPO1 (indicated by WT), mutant AtPPO1 (indicated by MT), and CyPPO12 gene on agar medium containing 0~400 μM of Pyraflufen-ethyl, Oxadiazon, Sulfentrazone, Pentoxazone or Pyraclonil.

FIGS. 4 to 6 show the results of examining herbicide resistance of CyPPO2, CyPPO4 and CyPPO8, and FIGS. 7 and 8 show the results of examining herbicide resistance of CyPPO12.

Figure 3:
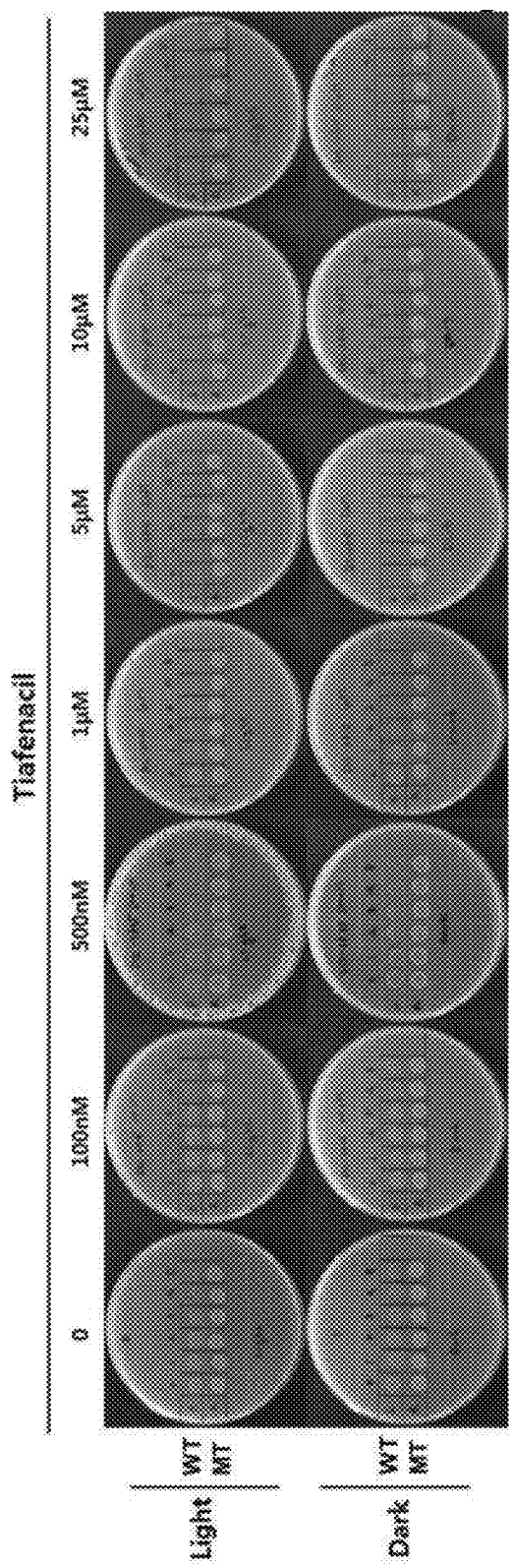
FIG. 3 is a photograph showing growth inhibition of respective BT3(ΔPPO) strains transformed with the wild-type AtPPO1 (indicated by WT) and mutant AtPPO1 (indicated by MT) genes after spotting them onto agar medium containing 0~25 μM Tiafenacil, and culturing them under light and dark conditions.

As shown in FIG. 3, growth of the strain transformed with the wild-type AtPPO1 was inhibited in the medium containing Tiafenacil under light and dark conditions, and stronger growth inhibition was observed under light condition than dark condition. For example, growth of the strain transformed with the wild-type AtPPO1 was almost completely inhibited at 1 µM of Tiafenacil under light condition, but its growth was rather maintained under dark condition. However, growth was completely inhibited at 5 µM or higher of Tiafenacil under both light and dark conditions. As such, growth of the strain transformed with the wild-type AtPPO1 was inhibited in a Tiafenacil concentration-dependent manner, indicating herbicide sensitivity. Growth inhibition of the strain transformed with the mutant AtPPO1 was not observed even at 25 µM of Tiafenacil, indicating herbicide resistance.

Therefore, the wild-type AtPPO1 was employed as a reference for herbicide-sensitive PPO, and the mutant AtPPO1 was employed as a reference for herbicide-resistant PPO, and herbicide resistance of CyPPO2, CyPPO4 or CyPPO8 against the representative PPO families was examined.

FIG. 4 shows the results after treatment with varying concentrations of representative pyrimidinedione-based PPO herbicides, Tiafenacil, Saflufenacil and Butafenacil, and a representative N-phenylphthalimide-based PPO herbicide, Flumioxazin. Upon treatment of Tiafenacil and Saflufenacil, growth inhibitions of the strain transformed with the mutant AtPPO1, the strain transformed with CyPPO2, the strain transformed with CyPPO4, and the strain transformed with CyPPO8 were hardly observed even at 25 µM of Tiafenacil or Saflufenacil. Upon treatment of Butafenacil, growth inhibitions of the strain transformed with the mutant AtPPO1, the strain transformed with CyPPO2, and the strain transformed with CyPPO8 were hardly observed even at 25 µM of Butafenacil. Upon treatment of Flumioxazin, growth inhibitions of the strain transformed with CyPPO2, the strain transformed with CyPPO4, and the strain transformed with CyPPO8 were hardly observed even at 25 µM of Flumioxazin. Upon treatment of each of the four herbicides, growth inhibition of the strain transformed with the wild-type AtPPO1 began at 0.5 µM and it hardly grew at 5 µM or higher.

FIG. 5 shows the results after treatment with varying concentrations of representative diphenyl ether-based PPO herbicides, Fomesafen, Acifluorfen and Oxyfluorfen. Upon treatment of Fomesafen, no growth inhibition of the strain transformed with the mutant AtPPO1 was observed by 25 µM, and growth inhibitions of the strain transformed with CyPPO2, the strain transformed with CyPPO4, and the strain transformed with CyPPO8 were hardly observed even at 400 µM of Fomesafen. Upon treatment of Acifluorfen, growth inhibitions of the strain transformed with CyPPO2, the strain transformed with CyPPO4, and the strain transformed with CyPPO8 were hardly observed even at 400 µM of Acifluorfen. Upon treatment of Oxyfluorfen, growth inhibitions of the strain transformed with CyPPO2, the strain transformed with CyPPO4, and the strain transformed with CyPPO8 were hardly observed even at 400 μM of Oxyfluorfen. Upon treatment of each of the three herbicides, the strain transformed with the wild-type AtPPO1 hardly grew at 5 μM or higher.

FIG. 6 shows the results after treatment with varying concentrations of a representative triazolinone-based PPO herbicide Sulfentrazone, a representative oxazolidinedione-based PPO herbicide Pentoxazone, a representative phenylpyrazole-based PPO herbicide Pyraflufen-ethyl, a representative oxadiazole-based PPO herbicide Oxadiazon, a representative thiadiazole-based PPO herbicide Fluthiacet-methyl, and other PPO herbicide Pyraclonil. Upon treatment of Sulfentrazone, growth inhibitions of the strain transformed with CyPPO2, the strain transformed with CyPPO4, and the strain transformed with CyPPO8 were hardly observed even at 400 μM of Sulfentrazone. Upon treatment of Pentoxazone, Pyraflufen-ethyl, Oxadiazon, Fluthiacet-methyl, and Pyraclonil, growth inhibitions of the strain transformed with CyPPO2 and the strain transformed with CyPPO8 were hardly observed even at 400 μM of Oxyfluorfen. Upon treatment of each of the seven herbicides, the strain transformed with the wild-type AtPPO1 hardly grew at 5 μM or higher.

FIG. 7 shows the results of examining herbicide resistance of CyPPO12 upon treatment of Tiafenacil, Saflufenacil, Flumioxazin, Fomesafen and Oxyfluorfen. Growth inhibition of the strain transformed with CyPPO12 was hardly observed even at each 25 μM of Tiafenacil, Saflufenacil, Flumioxazin, Fomesafen and Oxyfluorfen, and growth inhibition thereof was hardly observed even at 400 μM of Fomesafen or Oxyfluorfen. Upon treatment of Oxyfluorfen, growth inhibition of the strain transformed with the mutant AtPPO1 began at 5 μM. Growth inhibition thereof was hardly observed even at 25 μM of other herbicides. In contrast, growth inhibition of the strain transformed with the wild-type AtPPO1 began at each 0.5 μM of the four herbicides excluding Fomesafen, and it hardly grew at 5 μM or higher. Upon treatment of Fomesafen, growth inhibition of the strain transformed with the wild-type AtPPO1 was observed at 5 μM.

FIG. 8 shows the results of examining herbicide resistance of CyPPO12 upon treatment of Pyraflufen-ethyl, Oxadiazon, Sulfentrazone, Pentoxazone and Pyraclonil. No growth inhibitions of the strain transformed with the mutant AtPPO1 and the strain transformed with CyPPO12 were observed even at 25 μM, and no growth inhibitions thereof were also observed even at each 400 μM of the four herbicides excluding Sulfentrazone. In contrast, upon treatment of Pyraflufen-ethyl, Oxadiazon, Sulfentrazone, or Pyraclonil, growth inhibition of the strain transformed with the wild-type AtPPO1 began at 0.5 μM. Upon treatment of Pyraclonil, growth inhibition thereof began at 5 μM and it hardly grew at 25 μM.

Example 4. Test of Herbicide Resistance of CyPPO2, CyPPO4 and CyPPO8 in PPO-Deficient *E. coli* (LB Broth Medium)

In Example 3, herbicide resistance of respective BT3 (ΔPPO) strains transformed with the wild-type AtPPO1, mutant AtPPO1, CyPPO2, CyPPO4 or CyPPO8 gene was investigated on agar media containing different herbicides, and in this Example, herbicide resistance of the strains was investigated in LB liquid media containing different herbicides.

4-1. Preparation of Experimental Materials and Instruments

HV-50 autoclave from Hirayama, HS2100A electronic scale from Hansung Instrument, CB-30V clean bench from Jeio Tech, JSI-200CL incubator from JSR, MQ-200 photometer from Apogee, and 1210 type UV-visible spectrophotometer from Thermo Fisher Scientific were used. The autoclave was used under conditions of 121° C. and 15 minutes, and the incubator was used at 37° C. with lighting of 160~200 μmol m$^{-2}$ s$^{-1}$ for a culture time of 13.5 hours. The UV-visible spectrophotometer was used at 600 nm.

Tiafenacil (M.W. 511.87 g/mol), Saflufenacil (M.W. 500.85 g/mol), and Fomesafen (M.W. 438.76 g/mol) used in the experiment were purchased from Dongbu Farm Hannong Co., Ltd, Sigma, and Sigma, respectively. These drugs were prepared at 200 mM concentration in 100% acetone, and stored at −20° C., respectively. Luria-Bertani (LB) medium (10 g/L of Bacto-Tryptone, 5 g/L of Yeast extract, 10 g/L of sodium chloride) and an antibiotic Chloramphenicol (Duchefa) were used.

4-2. Experimental Method

For seed culture of *E. coli* transformed with respective genes, single colonies thereof were cultured in 3 ml of LB broth containing chloramphenicol for 12 hours, and they were diluted with LB broth to absorbance ($OD_{600}$) of 1.5. Next, chloramphenicol and 500 μl of the seed culture of the transformed *E. coli* were added to 250 ml of LB liquid medium, and 50 ml of the culture was added to each 250 ml-flask. Each flask was treated with varying concentrations (0, 10 μM, 50 μM, 100 μM) of herbicide stocks (Tiafenacil, Saflufenacil, Fomesafen), and then incubated at 37° C. and 200 rpm. Absorbance ($OD_{600}$) was measured using a spectrophotometer every 1.5 hours. The experiment was repeated three times, and mean values thereof were given in a graph. Error bars represent standard error of three repeats.

4-3. Experimental Result

The wild-type AtPPO1 was employed as a reference for herbicide-sensitive PPO, and the mutant AtPPO1 was employed as a reference for herbicide-resistant PPO.

Figure 9:
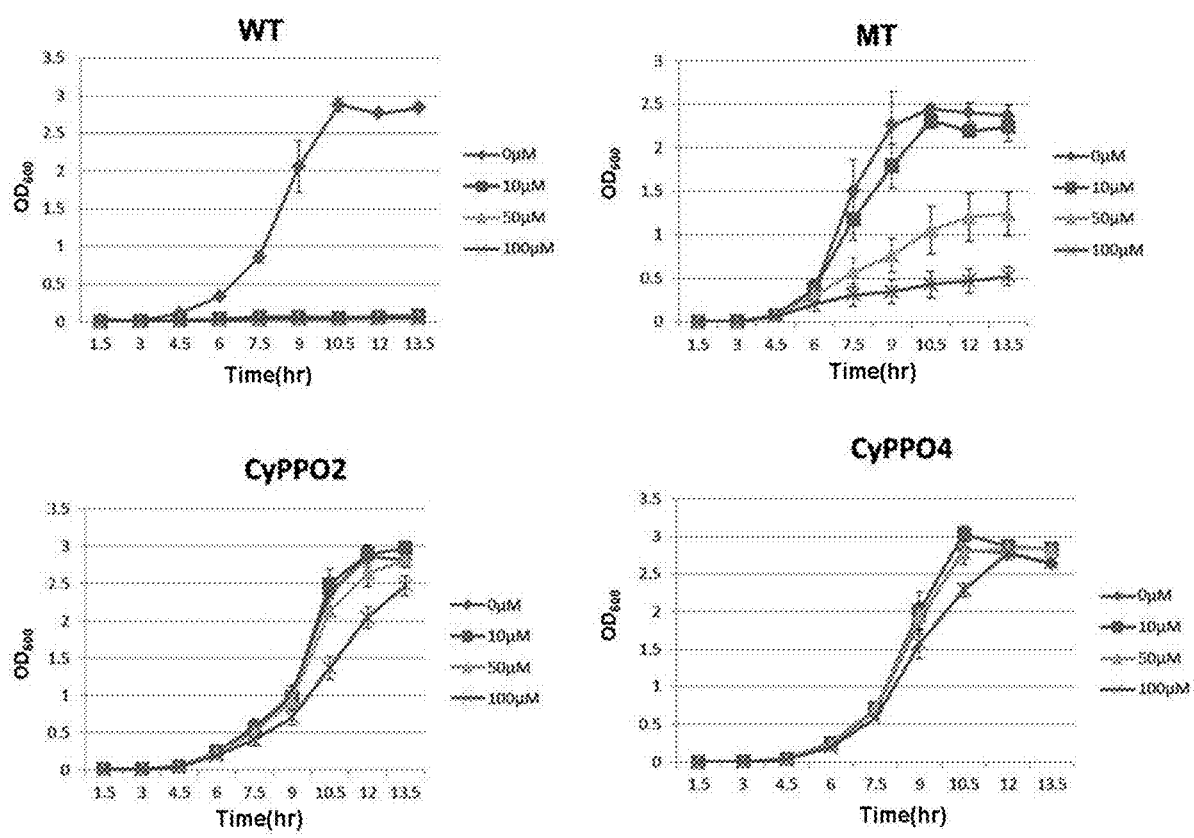
FIG. 9 is a graph showing growth inhibition of respective BT3(ΔPPO) strains transformed with the wild-type AtPPO1 (indicated by WT), mutant AtPPO1 (indicated by MT), CyPPO2 and CyPPO4 genes in liquid LB medium containing 0~100 μM of Tiafenacil over culture time.

The result of Tiafenacil treatment is shown in FIG. 9.

The strain transformed with the wild-type AtPPO1 hardly grew at 10 μM of Tiafenacil or higher, whereas the strain transformed with the mutant AtPPO1 grew at 10 μM of Tiafenacil, but growth inhibition thereof was observed at 50 μM of Tiafenacil or higher. Further, the strain transformed with CyPPO2 and the strain transformed with CyPPO4 normally grew by 100 μM of Tiafenacil.

Figure 10:
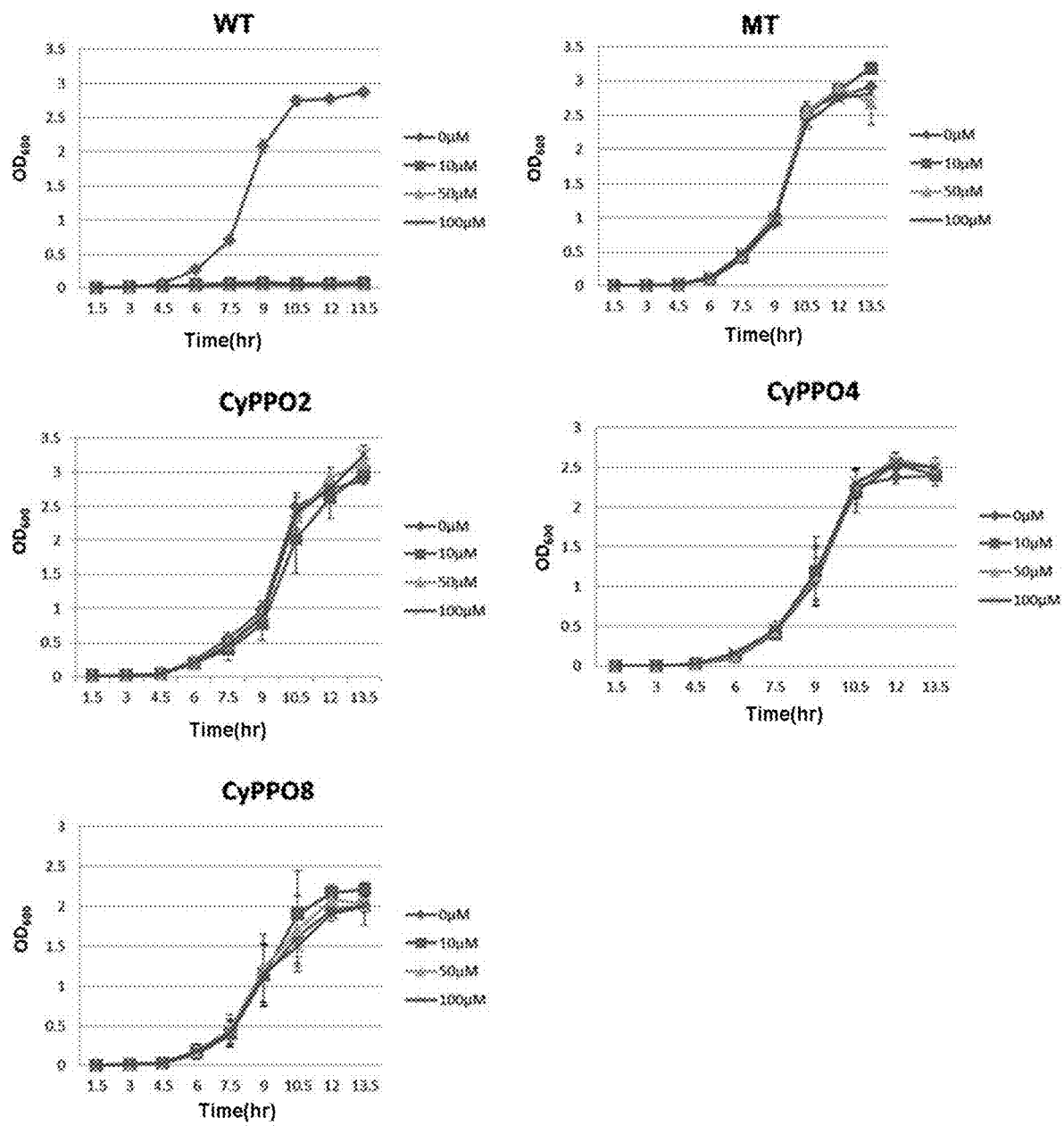
FIG. 10 is a graph showing growth inhibition of respective BT3(ΔPPO) strains transformed with the wild-type AtPPO1 (indicated by WT), mutant AtPPO1 (indicated by MT), CyPPO2, CyPPO4 and CyPPO8 genes in liquid LB medium containing 0~100 μM of Saflufenacil over culture time.

The result of Saflufenacil treatment is shown in FIG. 10.

In all the transformed strains, the presence or absence of resistance was similar to the result of Tiafenacil treatment, but high resistance was observed in the strains treated with Saflufenacil, compared to those treated with Tiafenacil. The strain transformed with the wild-type AtPPO1 hardly grew at 10 μM of Saflufenacil or higher, whereas the strain transformed with the mutant AtPPO1, the strain transformed with CyPPO2, the strain transformed with CyPPO4, and the strain transformed with CyPPO8 normally grew by 100 μm.

Figure 11:
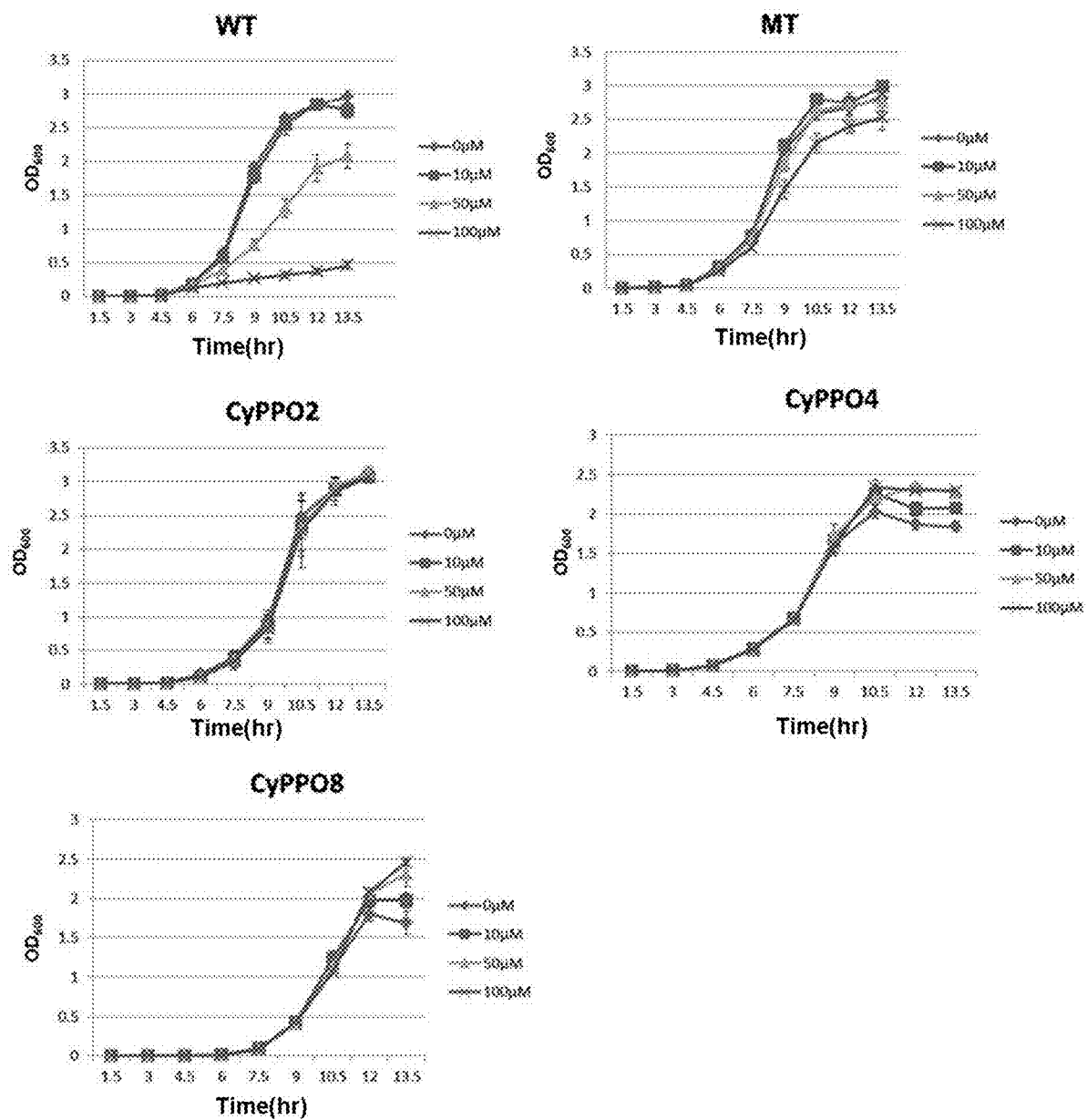
FIG. 11 is a graph showing growth inhibition of respective BT3(ΔPPO) strains transformed with the wild-type AtPPO1 (indicated by WT), mutant AtPPO1 (indicated by MT), CyPPO2, CyPPO4 and CyPPO8 genes in liquid LB medium containing 0~100 μM of Fomesafen over culture time.

The result of Fomesafen treatment is shown in FIG. 11.

Growth inhibition of the strain transformed with the wild-type AtPPO1 began at 50 μM, whereas the strain transformed with the mutant AtPPO1, the strain transformed with CyPPO2, the strain transformed with CyPPO4, and the strain transformed with CyPPO8 normally grew by 100 μM.

Example 5. Expression of CyPPO2, CyPPO4 and CyPPO8 in Plant

Experiments were performed to express CyPPO2, CyPPO4 and CyPPO8 in plants, of which resistance against various PPO herbicides had been demonstrated in Examples 3 and 4, and fluorescent protein (yellow fluorescent protein, YFP) was used to confirm expressions of the PPO proteins.

5-1. Experimental Method

To prepare *Agrobacterium* competent cells, *Agrobacterium tumefaciens* GV3101 strain (Korea Research Institute of Bioscience & Biotechnology) was cultured in 5 ml of LB media at 30° C. and 200 rpm for 12 hours. This culture broth was added to 200 ml of LB media, and then cultured at 30° C. and 200 rpm for 3~4 hours, followed by centrifugation at 3000 g, 4° C. for 20 minutes. The pellet was washed with sterile distilled water, and then resuspended in 20 ml LB media. 200 μL of aliquot thereof was snap-frozen in liquid nitrogen, and then stored in a deep freezer.

Figure 12:
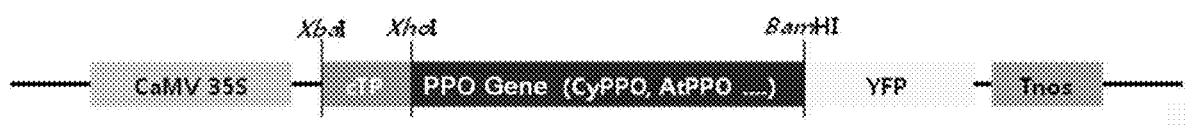
FIG. 12 is a schematic diagram showing a structure of a plant expression vector which was used to examine PPO gene expression in chloroplasts of tobacco leaves.

To prepare respective vectors which were cloned with the wild-type AtPPO1, CyPPO2, CyPPO4 and CyPPO8 genes, a vector containing a CaMV 35S promoter, YFP and NOS terminator was treated with XbaI and XhoI restriction enzymes, and a transit peptide gene (SEQ ID NO: 26) amplified by PCR was treated with XbaI and XhoI restriction enzymes, and then the vector and the transit peptide gene were ligated with each other to insert the transit peptide which is involved in transition of the chloroplast into the vector. Further, XhoI and BamHI restriction enzymes were used to digest respective PPO genes (wild-type AtPPO1, CyPPO2, CyPPO4 and CyPPO8 genes) and the vector, and then ligated with each other to insert the respective PPO genes into the vector. As a result, the transit peptide was linked to 5'-end of the PPO gene and YFP gene was linked to 3'-end thereof. A schematic diagram of the final vector is shown in FIG. 12.

Next, for *Agrobacterium*-mediated transformation, *Agrobacterium* competent cells prepared the above were thawed on ice, and then mixed with 3~5 μL of the vectors harboring the respective PPO genes, followed by snap freezing in liquid nitrogen for 2~3 minutes. Thereafter, the cells were thawed at 37° C. for 5 minutes, 1 ml of LB medium was added thereto, and incubated at 30° C. for 2 hours. Each resulting culture was plated on LB/spectinomycin medium and incubated at 30° C. for 2 days.

To inoculate tobacco leaves with *Agrobacterium*, *Agrobacterium* single colonies transformed with respective PPO-inserted vectors were cultured in LB/spectinomycin media at 30° C., 200 rpm for 12 hours, and centrifuged at 7000 rpm for 2 minutes. The resulting pellets were resuspended in 10 mM $MgCl_2$, respectively. After their absorbance ($OD_{600}$) was adjusted to 0.5, 200 μM acetosyringone was added and stored at room temperature for 2 hours. *Agrobacterium* was infiltrated into tobacco leaves normally grown using a 1 ml-syringe, and cultured for 2-5 days.

Next, to isolate protoplasts of tobacco leaves, an enzyme solution was prepared as in the composition of Table 3 or 5.

TABLE 3

| Composition | Content |
| --- | --- |
| CPW stock A (100x) | 5 ml |
| CPW stock B (10x) | 50 ml |
| Mannitol | 45 g |
| MES | 533 mg |
| Viscozyme (Novozymes; KWN00019; 700 EGU/g Cellulase) | 5 ml |
| Celluclast (Novozymes; CCN03123; 100 FBG/g Beta-glucanase) | 2.5 ml |
| pectinEX (Novozymes; KJN01013) | 2.5 ml |
| DDW | up to 500 ml | pH of the above solution was adjusted to 5.8, and sterilized using a filter having a 0.22 μm-pore size.

TABLE 4

| | | |
| --- | --- | --- |
| CPW stock A (100x) | $CaCl_2 \cdot 2H_2O$ | 1460 mg/L |
| CPW stock B (10x) | $KH_2PO_4$ | 27.2 mg/L |
| | $KNO_3$ | 101 mg/L |
| | $MgSO_4 \cdot 7H_2O$ | 246 mg/L |
| | KI | 0.16 mg/L |
| | $CuSO_4 \cdot 5H_2O$ | 0.025 mg/L |
| | pH | 5.8 |

TABLE 5

| Composition | Content |
| --- | --- |
| Mannitol | 1 g |
| 200 mM MES (pH 5.7) | 150 μL |
| viscozyme | 100 μL |
| celluclast | 50 μL |
| pectinEX | 50 μL |
| 1M $CaCl_2$ | 70 μL |
| DDW | up to 10 ml |

The tobacco leaves were cut into strips with a razor blade, and the leaf strips were suspended in the prepared enzyme solution, and covered with aluminum foil and stirred at room temperature at 40-50 rpm for 3-5 hours. A microscope (Carl Zeiss Observer Z1) and a biomaterial correlation analysis system (Zeiss LSM710) were used to examine protoplast cells with three types of filters, DIC, YFP and rhodamine. Images were captured using an imaging tool, and then processed using a ZEN lite 2012 (Carl Zeiss) program.

Fluorescent protein (YFP) expressed with the CyPPO2, CyPPO4 or CyPPO8 protein was examined by Western blotting. To this end, the samples were frozen and stored in liquid nitrogen, and then disrupted using a micropestle. IP buffer[50 mM Tris-Cl(pH7.5), 75 mM NaCl, 5 mM EDTA, 1% Triton X-100, 1 mM DTT, 1× protease inhibitor] (40 μL for large well) was added and vortexed, and then left on ice for 10 minutes or longer. After centrifugation at 4° C. for 10 minutes, the supernatant was transferred to a new 1.5 ml-tube. A protein loading dye was added thereto, boiled at 100° C. for 5 minutes, and then left on ice. After centrifugation, the supernatant was used. For electrophoresis, a protein extract solution was loaded on a 7.5% SDS-PAGE gel, and proteins were separated at 100 V for a stacking gel and at 150 V for a separating gel. The electrophoresed proteins were transferred onto a PVDF (polyvinylidene fluoride) membrane, and blocked with a blocking buffer (4% skim milk powder, 10 mM sodium phosphate, 0.15M NaCl, 0.05% Tween-20, pH 7.5) for 1 hour. Then, anti-GFP antibody (HRP-conjugated) (SantaCruz) was added at 1/2000 dilution, and reacted at room temperature for 2 hours. After antibody reaction, the membrane was washed with PBS-T (phosphate buffered saline-Tween) buffer for 10 minutes three times, and 500 μL of ECL (electrochemiluminescence) solution (buffer composition or supplier: Bio-Rad) was sprayed thereon and left for 1 minute. The membrane was covered with an OHP film, exposed to X-ray film, and then the film was developed.

5-2. Experimental Result

Figure 13:
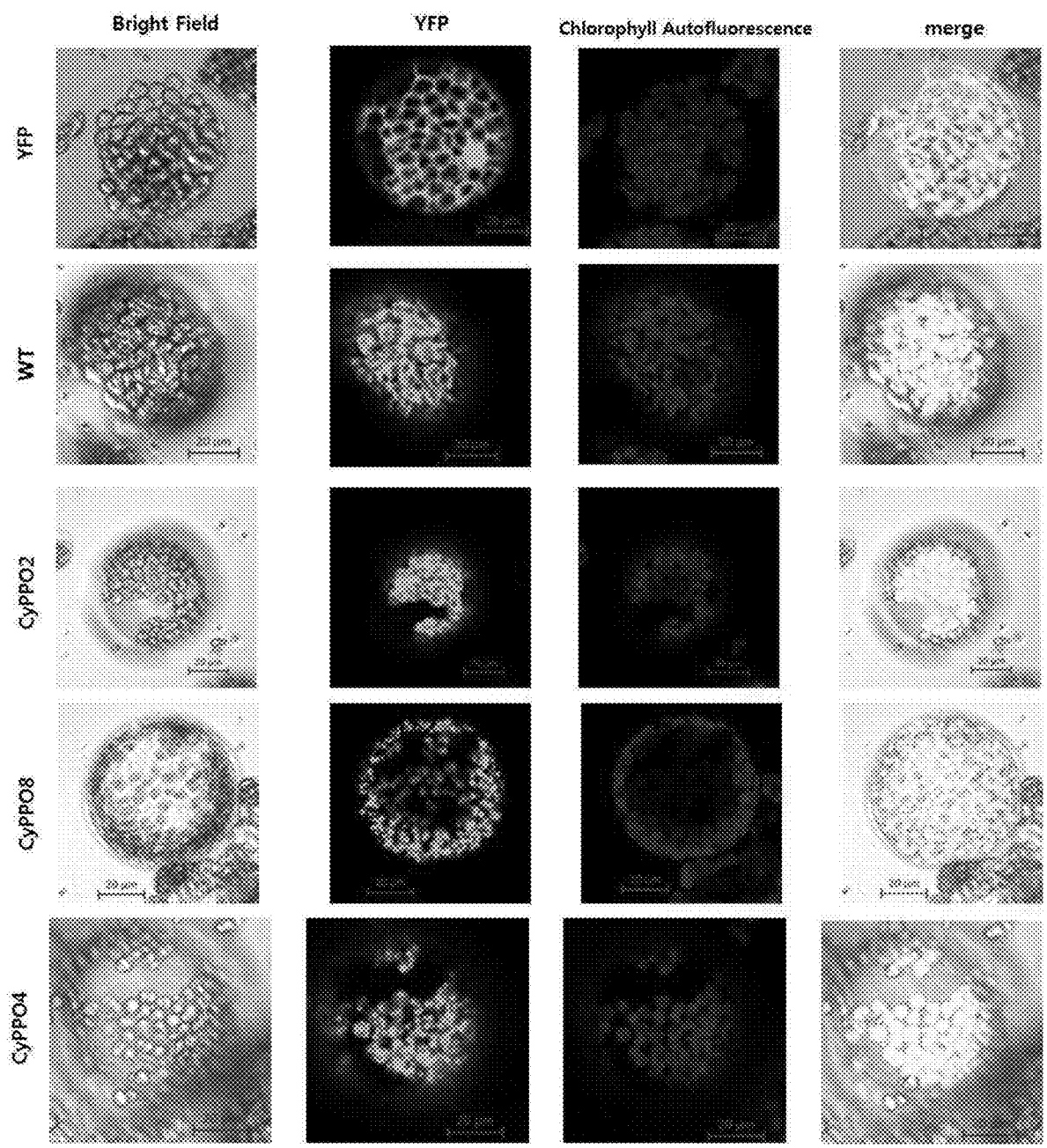
FIG. 13 shows the result of examining expressions of YFP, wild-type AtPPO1 (indicated by WT), CyPPO2, CyPPO4 and CyPPO8 genes in plant chloroplasts, after each of them was subcloned into the vector of FIG. 12, and then introduced into the plant.

The results of examining expressions of respective wild-type AtPPO1, CyPPO2, CyPPO4 and CyPPO8 genes after introduction into plants are shown in FIG. 13. Formation of *Agrobacterium* colonies was observed in the respective plants transformed with the PPO genes. Targeting of the negative control YFP protein to chloroplasts was not observed and expression thereof was observed in the cytoplasm and nucleus. The merged image of the PPO protein and chlorophyll autofluorescence showed that fluorescence signals were overlapped with each other, indicating that targeting to chloroplasts occurs by cTP (chloroplast transit peptide) which is linked to N-terminus for the purpose of targeting to the chloroplast.

Example 6. Preparation of Plant Transformation Vector and Transformant

Figure 14:
FIG. 14 is a schematic diagram showing a structure of a vector for plant transformation, which was used for transformation of *Arabidopsis thaliana* with PPO gene.
Figure 15:
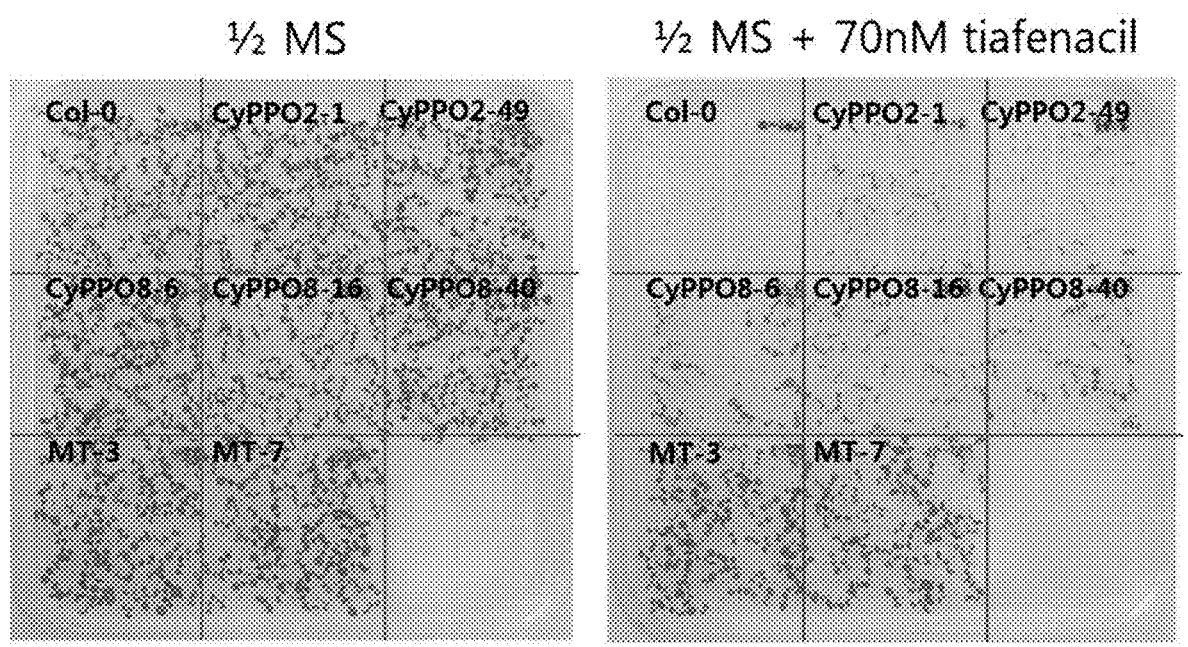
FIG. 15 is the result of examining seed germination of respective *Arabidopsis thaliana* T2 seeds transformed with the mutant AtPPO1 (indicated by MT), CyPPO2 and CyPPO8 genes in 1/2 MS medium or 1/2 MS medium containing 70 nM of tiafenacil. The mutant AtPPO1 (indicated by MT) as a control was a seed(T2) which was transformed with the gene having resistance against a PPO-based herbicide by amino acid replacement.

For plant transformation selection, a binary vector harboring ORF of BAR gene (glufosinate resistance gene) and ORF of respective CyPPO2, CyPPO4 or CyPPO8 gene was prepared and used. BAR gene was used to examine cross-treatment effects of other herbicides which have different mechanism of action from that of the PPO-based herbicides. This gene was also used to examine whether stable inheritance occurred in the next generation. To express BAR gene, a NOS promoter was used, and an E9 terminator was used to terminate transcription. Meanwhile, for expression induction of CyPPO2, CyPPO4 and CyPPO8 in plants, a CaMV35S promoter was used, and for targeting of the proteins to chloroplasts, a transit peptide (TP) region of AtPPO1 gene was inserted using XbaI and XhoI restriction enzymes. Further, to confirm the expressed proteins, hemagglutinin (HA) tag was inserted into 3'-end using BamHI and SacI restriction enzymes. The transit peptide region inserted into the vector is represented by SEQ ID NO: 27 and the inserted HA tag sequence is represented by SEQ ID NO: 28. The CyPPO2 and CyPPO8 genes were inserted between the transit peptide and HA tag using XhoI and BamHI restriction enzymes, and the NOS terminator was inserted behind HA tag to induce transcription termination of PPO gene. A schematic diagram showing the structure of the plant transformation binary vector is shown in FIG. 14.

Meanwhile, the plant transformant was prepared as follows. First, transformed *Agrobacterium* was selected in an antibiotic medium and then colonies were cultured in a liquid medium. *Agrobacterium* cells were harvested and suspended in a solution containing 5% sucrose and 0.05% Silwet L-77. Absorbance ($OD_{600}$) was adjusted to 0.8, and then a floral organ of *Arabidopsis thaliana* grown for about 5-6 weeks was put in the *Agrobacterium* solution. To maintain humidity, the pot was covered with a plastic bag, and left for a day in the dark. *Arabidopsis thaliana* inoculated with *Agrobacterium* was further grown for 1-2 months, and seeds were matured, and then harvested. Because seeds harvested from the transformed plant were a mixture of transformed and non-transformed seeds, a process of selecting transformed seeds from the harvested seeds is required.

Accordingly, BAR gene which was inserted for selection of transformed individuals during the vector preparation was used to select transformants (transformants were selected using glufosinate), which were transplanted to soil and grown to obtain a T1 plant.

To examine resistance of the transplanted T1 plants against PPO-based herbicides, the plants were grown for about 3-4 weeks, and then treated with herbicides prior to flower stalk elongation. *Arabidopsis thaliana* ecotype Col-0 was found to be killed when treated with 2-3 ml of 1 μM tiafenacil (+0.05% Silwet L-77) per plant. Therefore, 1 μM tiafenacil was evenly applied at an amount proper for the number of plant individuals. After 7 days, resistance of the transformants against PPO-based herbicides was examined. The plants that showed resistance and thus survived were continuously grown, and their seeds (T2 seed) were harvested, and the T2 seeds were cultured in 1/2 MS medium for a week, and then transplanted to soil to obtain a T2 plant.

Example 7. Germination Test

To examine tiafenacil resistance of T2 generation seeds which survived under treatment of 1 μM tiafenacil, among the CyPPO2 and CyPPO8 transformants, *Arabidopsis thaliana* seeds were sown in 1/2 MS medium (1.125 g/L of MS salt, 10 g/L of sucrose, 7 g/L of Agar) containing 70 nM tiafenacil. The wild-type *Arabidopsis thaliana* (Col-0; Columbia-0 ecotype) showed a reduced seed germination in 1/2 MS medium containing 50 nM tiafenacil, and Col-0 showed no normal seed germination and was killed in 1/2 MS medium containing 70 nM tiafenacil. Therefore, survival under 70 nM tiafenacil means that a plant has resistance against tiafenacil.

As a result, as shown in FIG. 5, no. 1 and 49 among T2 generation lines of the CyPPO2 transformants showed germination, and no. 6, 16 and 40 among T2 generation lines of the CyPPO8 transformants showed germination in 1/2 MS medium containing 70 nM tiafenacil. Further, the wild-type *Arabidopsis thaliana*(Col-0) seed used as a negative control showed no germination in 1/2 MS medium containing 70 nM tiafenacil. The mutant AtPPO1 transformant used as a positive control showed germination even in 1/2 MS medium containing 70 nM tiafenacil.

Example 8. Inheritance Test 8-1. Examination of Segregation Ratio of T2 Generation Seed The herbicide resistance trait was observed in the next generation of the transformed *Arabidopsis thaliana*, and therefore, in order to determine inheritance, segregation ratios of BAR gene-resistant and sensitive T2 seeds were determined in each line.

In the case of the CyPPO2 transformant, a segregation ratio close to 3:1 was obtained in line no. 10, 20, 38, and 40 among 10 lines, indicating that a single copy of transgene was integrated into the genome, and segregated and expressed according to the Mendelian. The remaining 6 lines showed no segregation ratio of 3:1, implying double copy or greater.

In the case of the CyPPO8 transformant, a segregation ratio close to 3:1 was obtained in line no. 6, 16, and 40 among 5 lines, indicating that a single copy of transgene was integrated into the genome, and segregated and expressed according to the Mendelian. The remaining 2 lines showed a segregation ratio lower than 3:1.

TABLE 6

| CyPPO2-HA transformant (T2) | |
| --- | --- |
| Line no. | Segregation ratio |
| 1 | 4.56:1 |
| 8 | 1.56:1 |
| 10 | 2.85:1 |
| 20 | 2.70:1 |
| 23 | 1.5:1 |
| 30 | 1.7:1 |
| 35 | 2.03:1 |
| 38 | 2.57:1 |
| 40 | 3.17:1 |
| 49 | 2.41:1 |

TABLE 7

| CyPPO8-HA transformant (T2) | |
| --- | --- |
| Line no. | Segregation ratio |
| 6 | 2.57:1 |
| 16 | 2.85:1 |
| 23 | 2.23:1 |
| 38 | 2.03:1 |
| 40 | 2.85:1 |

8-2. Examination of CyPPO2 and CyPPO8 Protein Expressions in Herbicide-Resistant T2 Generation Seed To examine whether CyPPO2 and CyPPO8 protein expressions are maintained in the next generation, proteins were extracted from each T2 generation line of transformants, followed by Western blotting. To detect the amounts of HA-tagged PPO proteins, proteins were extracted from about 100 mg of *Arabidopsis thaliana* leaf, followed by electrophoresis. The proteins were transferred onto a PVDF membrane, and then Western blotting was performed using anti-HA antibody. 1 μM tiafenacil was sprayed onto T1 generation plants. Plants that survived were classified as resistant, and plants that were killed were classified as sensitive.

Figure 16:
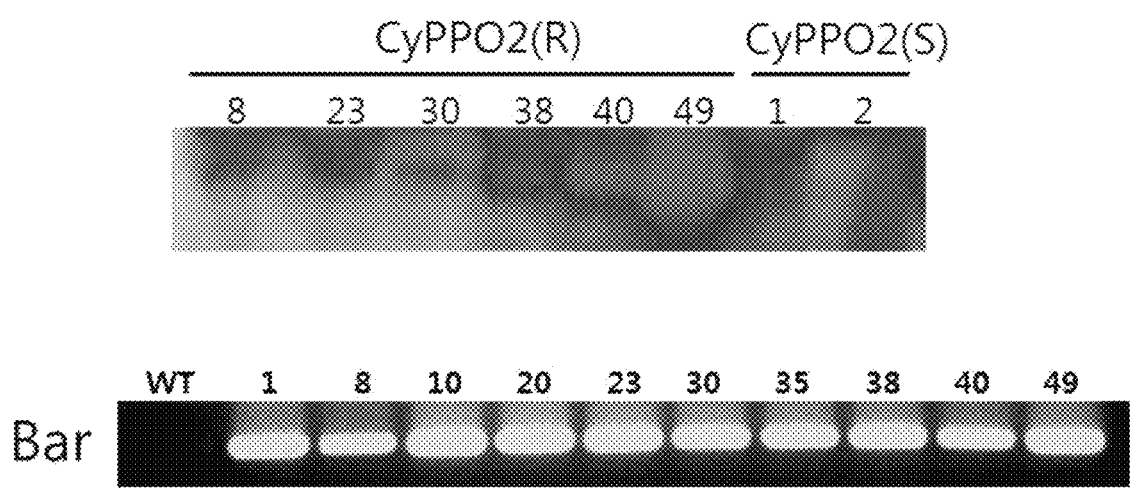
FIG. 16 shows the result of Western blotting of each line of *Arabidopsis thaliana* T2 generation transformed with CyPPO2 gene to examine whether expression of CyPPO2 protein is maintained in the next generation. CyPPO2(R) indicates the herbicide-resistant transformant line, and CyPPO2(S) indicates the herbicide-sensitive transformant line. The lower panel of FIG. 16 shows the result of PCR to examine insertion of BAR gene into a binary vector.
Figure 17:
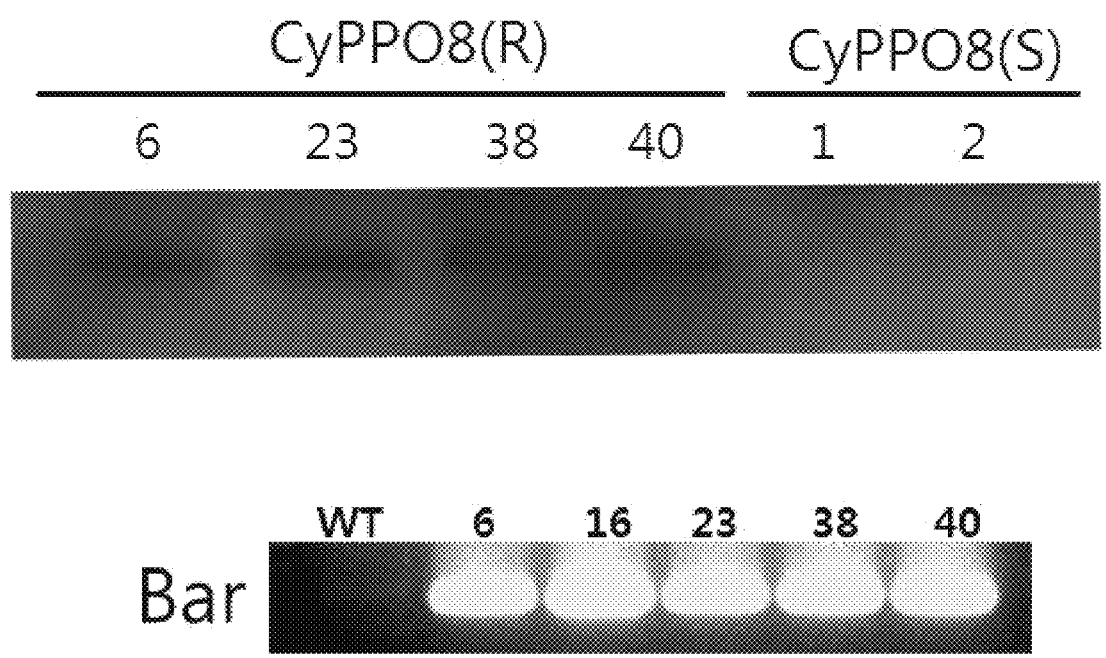
FIG. 17 shows the result of Western blotting of each line of *Arabidopsis thaliana* T2 generation transformed with CyPPO8 gene to examine whether expression of CyPPO8 protein is maintained in the next generation. CyPPO8(R) indicates the herbicide-resistant transformant line, and CyPPO8(S) indicates the herbicide-sensitive transformant line. The lower panel of FIG. 17 shows the result of PCR to examine insertion of BAR gene into a binary vector.

In the case of CyPPO2 transformant, PPO proteins were detected in line no. 8, 23, 30, 38, 40 and 49 which showed resistance upon spraying herbicides thereto, and not detected in sensitive lines (FIG. 16). In the case of CyPPO8 transformant, PPO proteins were detected in line no. 6, 23, 38, and 40 having herbicide resistance, and not detected in sensitive lines (FIG. 17). These results suggest that expressions of CyPPO2 and CyPPO8 proteins were maintained in the next generations of the resistant lines, providing resistance.

8-3. Examination of Stable Inheritance of Transgene Using BAR Gene

Stable inheritance of the transgene to the next generation was investigated by examining integration of the transformed gene, BAR into the genome. Genomic DNAs were isolated from 100 mg of the leaves of CyPPO2 and CyPPO8 transformants, and then integration of BAR gene was examined by PCR. As a result, genome integration of BAR gene was observed in both tiafenacil-resistant and sensitive lines of the CyPPO2 transformant and CyPPO8 transformant, indicating stable inheritance of the transformed genes to the next generation.

Example 9. Examination of Herbicide Resistance of Transformed *Arabidopsis thaliana*

Figure 18:
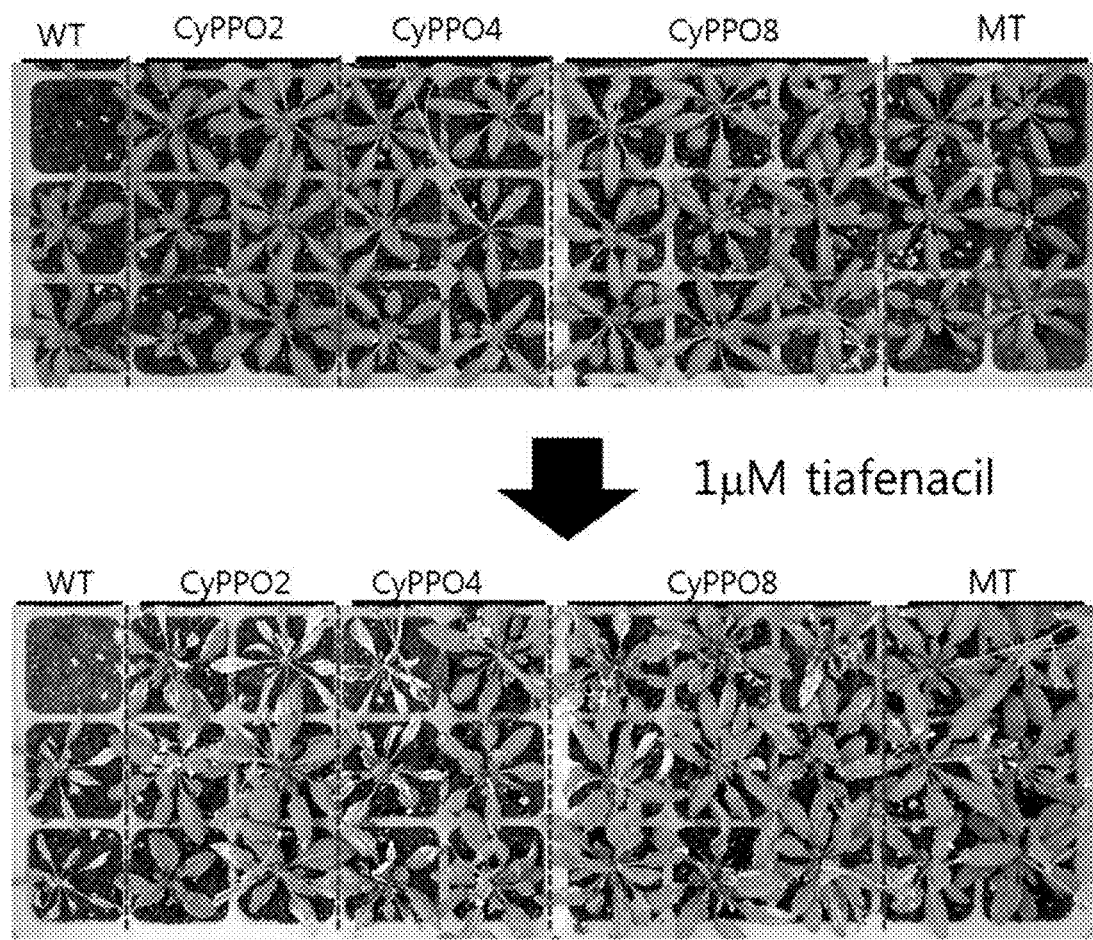
FIG. 18 shows the result of examining growth of respective *Arabidopsis thaliana* T2 generations transformed with CyPPO2, CyPPO4 and CyPPO8 genes and a control mutant AtPPO1 (indicated by MT) gene at 7 days after spraying 1 μM Tiafenacil thereto. WT indicates the result of the wild-type *Arabidopsis thaliana*.
Figure 19:
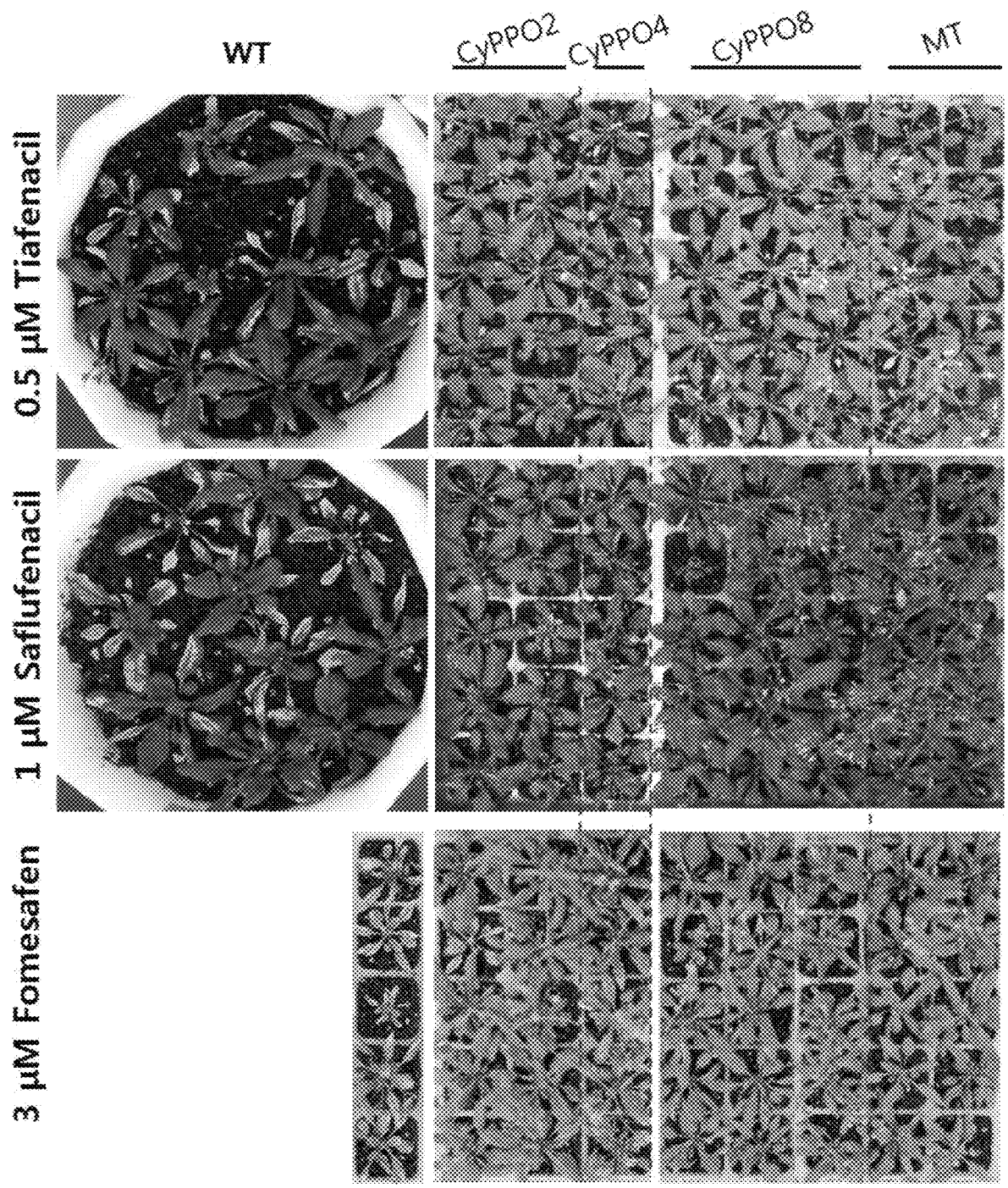
FIG. 19 shows the result of examining growth of respective *Arabidopsis thaliana* T2 generations transformed with CyPPO2, CyPPO4 and CyPPO8 genes and the control mutant AtPPO1 (indicated by MT) gene at 7 days after spraying 0.5 μM Tiafenacil, 1 μM Saflufenacil, or 3 μM Fomesafen thereto. WT indicates the result of the wild-type *Arabidopsis thaliana*.

To examine whether herbicide resistance traits are maintained in the next generations of plants, respective T2 generation plants of *Arabidopsis thaliana* which were transformed with CyPPO2, CyPPO4 and CyPPO8 genes were subjected to an herbicide resistance test. 2~3 ml of 0.5 μM Tiafenacil, 1 μM Saflufenacil, or 3 μM Fomesafen was sprayed onto each *Arabidopsis thaliana* plant grown for about 4 weeks. At 7 days after spraying, the wild-type Col-0 plants were killed, whereas the positive control, mutant AtPPO1 transformant and the experimental groups, CyPPO2 transformant, CyPPO4 transformant and CyPPO8 transformant continued to grow without damage (FIGS. 18 and 19), indicating that herbicide resistance traits of T1 plants were maintained well to provide T2 generations with herbicide resistance.

Figure 20:
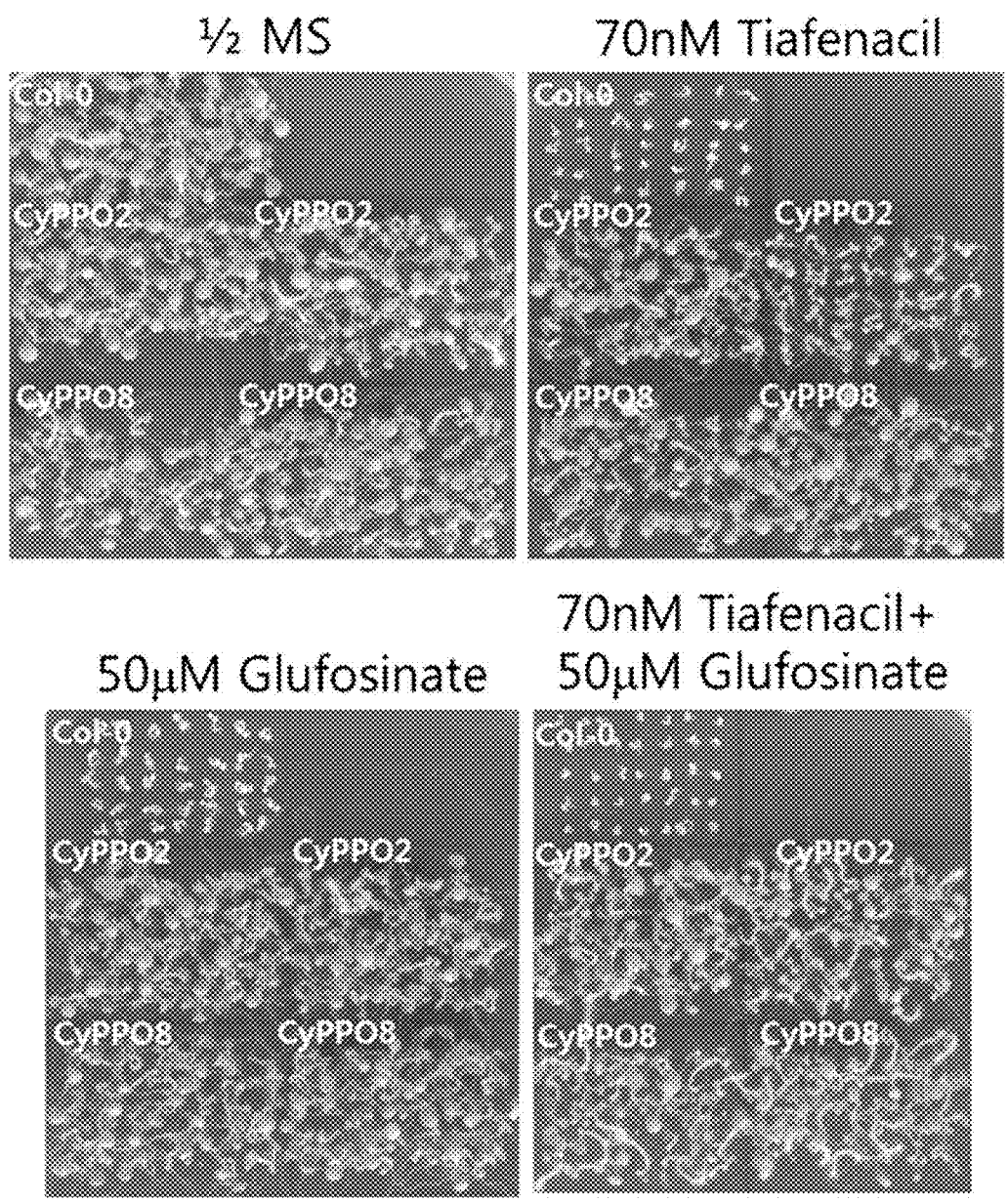
FIG. 20 shows the result of culturing respective seeds of CyPPO2 and BAR gene-inserted *Arabidopsis thaliana* transformant and CyPPO8 and BAR gene-inserted *Arabidopsis thaliana* transformant in a glufosinate-added medium, Tiafenacil-added medium, or glufosinate and Tiafenacil-added medium.

Example 10. Cross Use Experiment of Plural Herbicides with Different Mechanism of Action In *Arabidopsis thaliana* transformant including CyPPO2 or CyPPO8 gene, which was obtained by transformation using the plant transformation vector prepared in Example 6, the PPO activity-inhibiting herbicide-resistant gene and glufosinate-resistant gene are expressed at the same time. Therefore, it was examined whether cross-treatment of *Arabidopsis thaliana* transformant with two herbicides, namely, PPO activity-inhibiting herbicide and glufosinate is effective for weed control. To this end, seeds of CyPPO2 and BAR gene-inserted *Arabidopsis thaliana* transformant, or CyPPO8 and BAR gene-inserted *Arabidopsis thaliana* transformant were sterilized and treated at low temperature of 4° C. for 2 days. The seeds were sown in a 1/2 MS medium (Duchefa), a 1/2MS medium containing 70 nM Tiafenacil, a 1/2MS medium containing 50 uM glufosinate, or a 1/2MS medium containing 70 nM Tiafenacil and 50 uM glufosinate, and grown at 23° C. under 16 hour-light/8 hour-dark conditions for 7~14 days. *Arabidopsis thaliana* on the herbicide media was CyPPO2 or CyPPO8-transformed seed and the wild-type Col0 as a control, respectively. The transformant and the control were cultured on herbicide media. After 2 weeks, they were examined. As a result, CyPPO2 and CyPPO8 normally grew on a glufosinate-added medium, a Tiafenacil-added medium, or a glufosinate and Tiafenacil-added medium, whereas the control Col0 was not germinated (see FIG. 20).

These results show that when transformed plants are prepared by recombination of the PPO herbicide-resistant gene of the present invention and BAR gene in a binary vector, and cross- or double-treatment of these GM plants with herbicides having different mechanism of action is performed, undesired plants can be controlled.

In this Example, BAR gene introduced as a recombinant gene, together with CyPPO gene, is illustrative only for a resistant gene, and there is no limitation in the type of the gene to be used in the present invention. It is apparent to those skilled in the art that when a resistant gene adequate for the purpose and CyPPO 2, 4, 8 or 12 are recombined with the binary vector, and herbicides to which respective genes are resistant are cross-treated, desired resistance can be obtained.

Example 11. Cross Use Experiment of Plural PPO Herbicides

Figure 21:
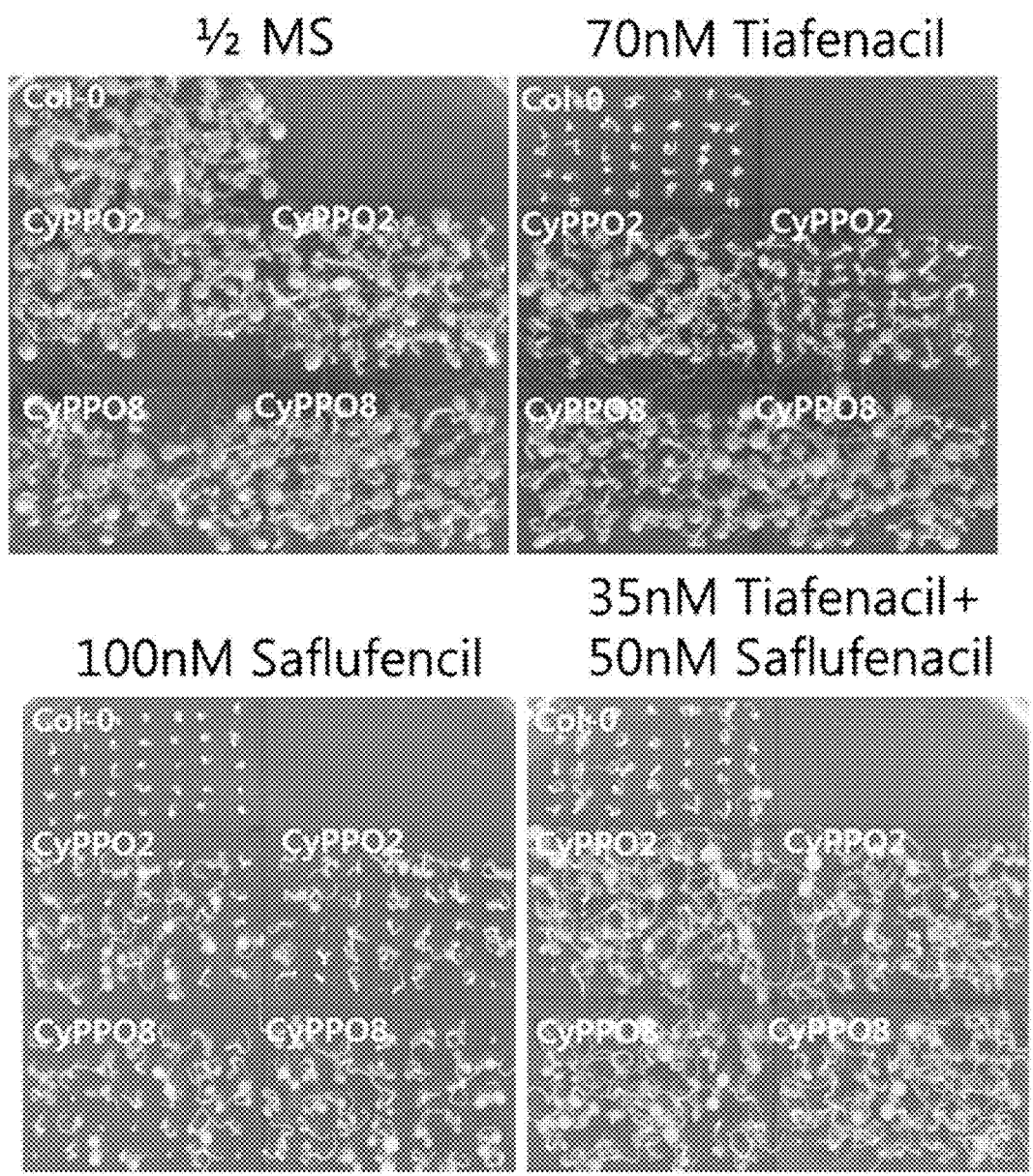
FIG. 21 shows the result of culturing the seed of CyPPO2 or CyPPO8 gene-inserted *Arabidopsis thaliana* transformant in a Tiafenacil-added medium, Saflufenacil-added medium, or Tiafenacil and Saflufenacil-added medium.
Figure 22:
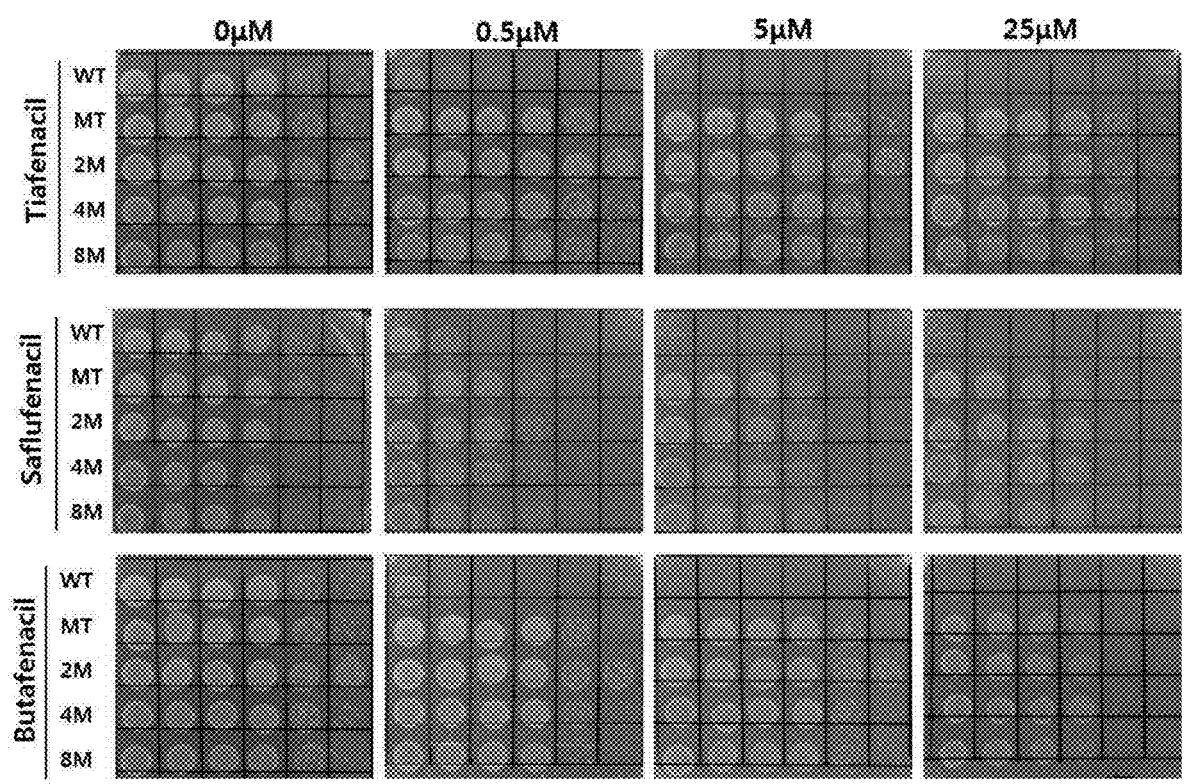
FIG. 22 shows the result of examining a relationship between amino acid homology of CyPPO2, CyPPO4, or CyPPO8 protein and herbicide resistance, and is a photograph showing growth inhibition of respective BT3(ΔPPO) strains transformed with CyPPO2 amino acid sequence variant (indicated by 2M), CyPPO4 amino acid sequence variant (indicated by 4M) and CyPPO8 amino acid sequence variant (indicated by 8M) genes in agar media with varying concentrations of Tiafenacil, Saflufenacil and Butafenacil. As a control group to determine growth inhibition, wild-type AtPPO1 (indicated by WT) and Mutant AtPPO1 (indicated by MT) were used.
Figure 23:
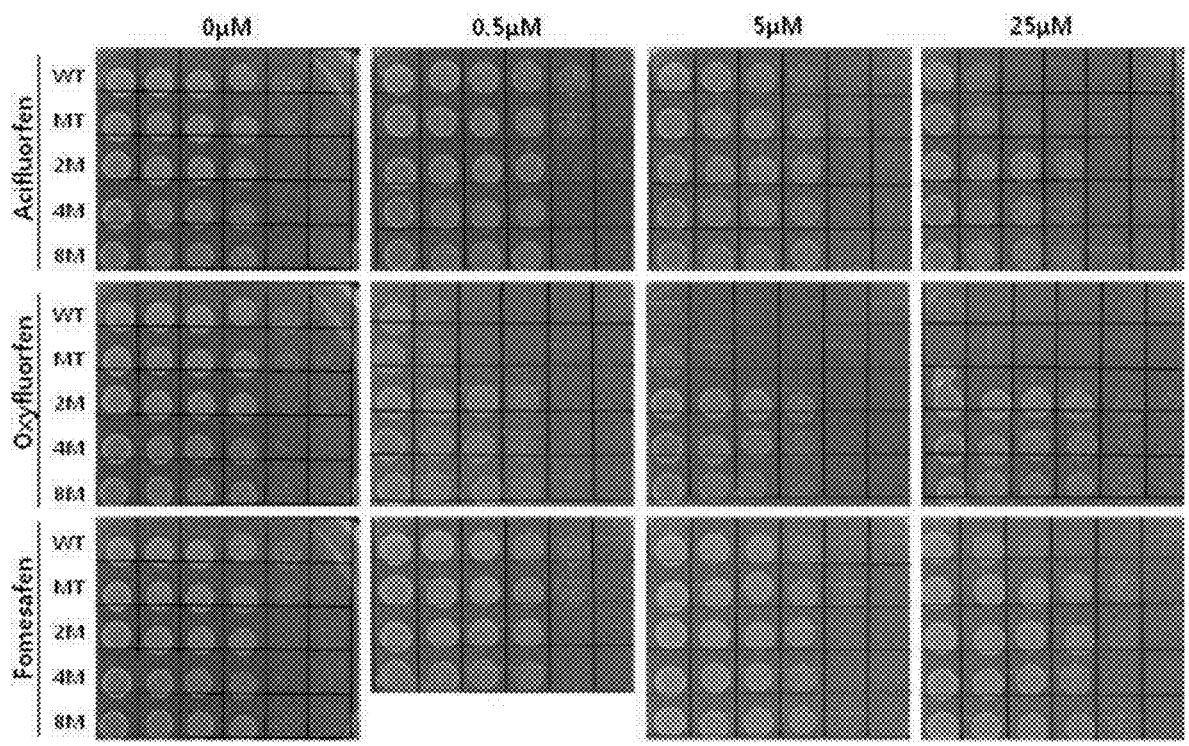
FIG. 23 is a photograph showing growth inhibition of respective BT3(ΔPPO) strains transformed with CyPPO2 amino acid sequence variant (indicated by 2M), CyPPO4 amino acid sequence variant (indicated by 4M) and CyPPO8 amino acid sequence variant (indicated by 8M) genes in agar media with varying concentrations of Acifluorfen, Oxyfluorfen and Fomesafen. As a control group to determine growth inhibition, wild-type AtPPO1 (indicated by WT) and Mutant AtPPO1 (indicated by MT) were used.
Figure 24:
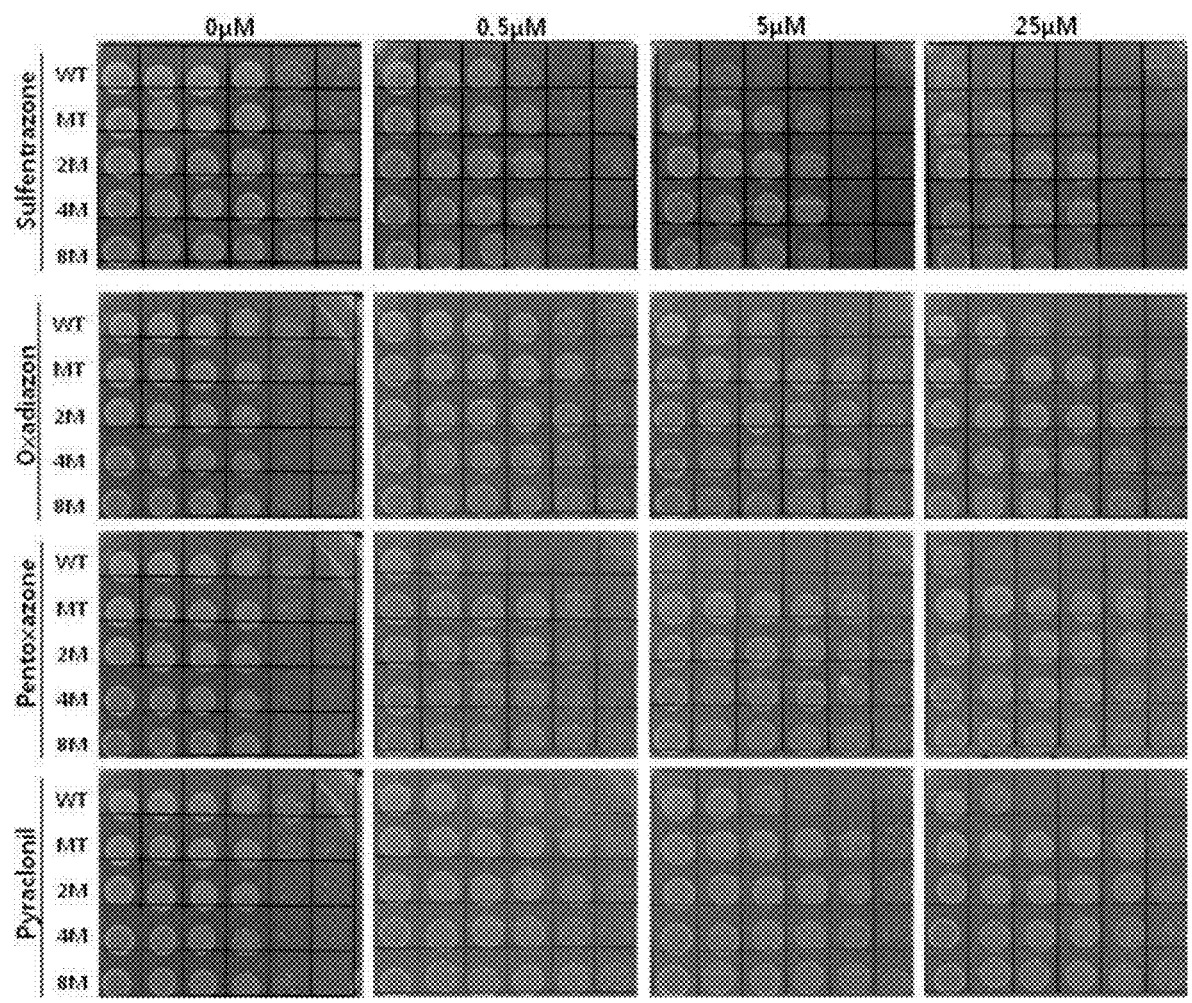
FIG. 24 is a photograph showing growth inhibition of respective BT3(ΔPPO) strains transformed with CyPPO2 amino acid sequence variant (indicated by 2M), CyPPO4 amino acid sequence variant (indicated by 4M) and CyPPO8 amino acid sequence variant (indicated by 8M) genes in agar media with varying concentrations of Sulfentrazone, Oxadiazon, Pentoxazone and Pyraclonil. As a control group to determine growth inhibition, wild-type AtPPO1 (indicated by WT) and Mutant AtPPO1 (indicated by MT) were used.
Figure 25:
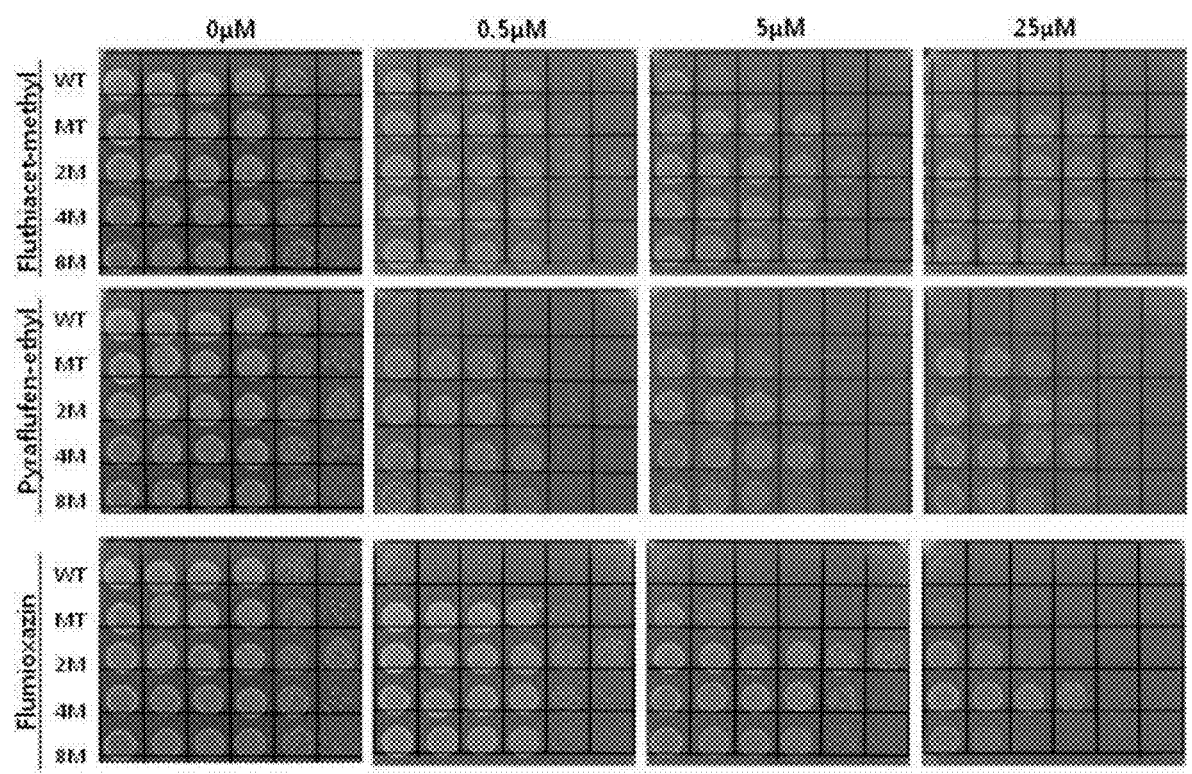
FIG. 25 is a photograph showing growth inhibition of respective BT3(ΔPPO) strains transformed with CyPPO2 amino acid sequence variant (indicated by 2M), CyPPO4 amino acid sequence variant (indicated by 4M) and CyPPO8 amino acid sequence variant (indicated by 8M) genes in agar media with varying concentrations of Fluthiacet-methyl, Pyraflufen-ethyl and Flumioxazin. As a control group to determine growth inhibition, wild-type AtPPO1 (indicated by WT) and Mutant AtPPO1 (indicated by MT) were used.

In Example 9, it was confirmed that *Arabidopsis thaliana* transformant prepared in the present invention has resistance against the two PPO-based herbicides, Tiafenacil and Saflufenacil at the same time, and therefore, it was tested whether the cross-treatment of *Arabidopsis thaliana* transformant with Tiafenacil and Saflufenacil is effective for weed control. To this end, seeds of CyPPO2 or CyPPO8 gene-inserted *Arabidopsis thaliana* transformant were sterilized and treated at low temperature of 4° C. for 2 days. The seeds were sown in a 1/2 MS medium, a 1/2MS medium containing 70 nM Tiafenacil, a 1/2MS medium containing 70 nM Saflufenacil, or a 1/2MS medium containing 35 nM Tiafenacil and 35 nM Saflufenacil, and grown at 23° C. under 16 hour-light/8 hour-dark conditions for 7~14 days. *Arabidopsis thaliana* on the herbicide media was CyPPO2 or CyPPO8-transformed seed and the wild-type Col0 as a control, respectively. The transformant and the control were cultured on herbicide media. After 2 weeks, they were examined. As a result, CyPPO2 and CyPPO8 normally grew on a Tiafenacil-added medium, a Saflufenacil-added medium, or a Tiafenacil and Saflufenacil-added medium, whereas the control Col0 was not germinated (see FIG. 21).

These results show that when GM plants are prepared using PPO herbicide-resistant genes of the present invention, and cross- or double-treatment of plural PPO-based herbicides as well as single treatment of PPO-based herbicides is performed, undesired plants can be controlled.

Example 12. Examination of Herbicide Resistance According to Amino Acid Sequence Homology of CyPPO2, CyPPO4 and CyPPO8

To investigate amino acid sequence homology range of CyPPO2, CyPPO4 and CyPPO8 which maintain herbicide resistance, a part of the amino acid sequence of CyPPO2, CyPPO4 or CyPPO8 protein was replaced by a part of the amino acid sequence of NtPPO (tobacco-derived PPO gene). As a result, the amino acid sequence of the resulting CyPPO2 variant is represented by SEQ ID NO: 12, and its nucleotide sequence thereof is represented by SEQ ID NO: 13. The amino acid sequence and the nucleotide sequence of the CyPPO2 variant showed 98% sequence homology to those of CyPPO2, respectively. Further, the amino acid sequence of the CyPPO4 variant is represented by SEQ ID NO: 14, and its nucleotide sequence thereof is represented by SEQ ID NO: 15. The amino acid sequence and the nucleotide sequence of the CyPPO4 variant showed 98% sequence homology to those of CyPPO4, respectively. Further, the amino acid sequence of the CyPPO8 variant is represented by SEQ ID NO: 16, and its nucleotide sequence thereof is represented by SEQ ID NO: 17. The amino acid sequence and the nucleotide sequence of the CyPPO8 variant showed 98% sequence homology to those of CyPPO8, respectively.

Herbicide resistance of the amino acid sequence variant of CyPPO2, the amino acid sequence variant of CyPPO4, and the amino acid sequence variant of CyPPO8 was investigated in PPO-deficient BT3 *E. coli* [BT3(ΔPPO)], and a specific experimental method is similar to that of Example 3. In the same manner as in Example 3, as a negative control, the wild-type PPO (wild-type AtPPO1) of *Arabidopsis thaliana* was employed as a reference for herbicide-sensitivity. As a positive control, the mutant AtPPO1 which was prepared by amino acid replacement of Y426M and S305L in the wild-type amino acid sequence was employed as a reference for herbicide-resistance.

12-1. Preparation of Experimental Materials and Instruments

An autoclave was used under conditions of 121° C. and 15 minutes, and an incubator was used at 37° C. with lighting of 169 $\mu mol^{-2}s^{-1}$ for a culture time of 14~16 hours. A UV-visible spectrophotometer was used at 600 nm. PCR was performed under conditions of at 94° C. for 4 minutes, and 25 cycles (at 94° C. for 30 seconds, at 56~60° C. for 30 seconds and at 72° C. for 3 minutes), at 72° C. for 5 minutes and at 4° C. for 5 minutes. The herbicides used in the experiment are given in the following Table 8. Respective herbicides were prepared at a concentration of 200 mM in DMSO, and stored at −20° C. Before use, the herbicides were diluted and added to LB broth medium (containing 34 mg/ml chloramphenicol).

TABLE 8

| Chemical family | Herbicide (original name) | Manufacturer/Supplier |
|---|---|---|
| Pyrimidinedione | Tiafenacil | Dongbu Farm Hannong Co., Ltd./Dongbu Farm Hannong Co., Ltd. |
|  | Saflufenacil | BASF/Sigma |
|  | Butafenacil | Syngenta/Sigma |
| Diphenyl ether | Fomesafen | Syngenta/Sigma |
|  | Acifluorfen | United Phosphorus/Supelco |
|  | Oxyfluorfen | Dow/Sigma |
| N-phenylphthalimides | Flumioxazin | Sumitomo/Sigma |
| Triazolinones | Sulfentrazone | FMC/Waka |
| Oxizolidinediones | Pentoxazone | Kaken/Sigma |
| Phenylpyrazoles | Pyraflufen-ethyl | Nihon Nohyaky/Sigma |
| Others | Pyraclonil | Kyoyu Agri/Sigma |
| Oxadiazoles | Oxadiazon | Bayer/Sigma |
| Thiadiazoles | Fluthiacet-methyl | FMC/Sigma |

12-2. Experimental Method

Saturated cells were inoculated in 3 ml of LB liquid medium containing chloramphenicol, and then cultured at 37° C., 200 rpm for 5 hours. Density of the cultured cells was measured at 600 nm, and the transformants were diluted with LB liquid medium to have the same absorbance ($OD_{600}$) per 1 ml thereof ($OD_{600}$=0.5). Agar was added to LB liquid medium at a concentration of 1%, and then autoclaved. Chloramphenicol (34 μg/ml) and herbicide were added and mixed. Cells diluted equally was diluted at a density of $10^0$, $10^{-1}$, $10^{-2}$, $10^{-3}$, $10^{-4}$, and $10^{-5}$. Each 10 μl of the cells was dropped on 1% agar, LB solid medium, and cultured in a 37° C. incubator for 14~16 hours (light condition: 169 $\mu mol\ m^{-2}\ s^{-1}$).

pACBB-CyPPO2, pACBB-CyPPO4 and pACBB-CyPPO8 were used as templates to prepare primers for the region to be replaced (Table 9), and PCR was performed to prepare pACBB-CyPPO2 variant, pACBB-CyPPO4 variant and pACBB-CyPPO8 variant vectors. 50 μl of PCR reaction mixture was prepared by mixing 1 μl of each template (pACBB-CyPPO2, pACBB-CyPPO4 and pACBB-CyPPO8 original), 5 μl of 10× buffer, 1 μl of dNTP mixture (each 10 mM), 1 μl of a forward primer (10 μM), 1 μl of a reverse primer (10 μM), 35 μl of DDW, and 1 μl of Pfu-X (Solgent, 2.5 unit/μl), and amplification was performed under conditions of at 94° C. for 4 minutes, and 25 cycles (at 94° C. for 30 seconds, at 56° C. for 30 seconds and at 72° C. for 3 minutes), at 72° C. for 5 minutes and at 4° C. for 5 minutes.

TABLE 9

| Strain | Primer | Sequence (for pACBB cloning) | SEQ ID NO: |
|---|---|---|---|
| *Oscillatoria nigro-viridis* PCC 7112 | CyPPO2Nt98%_F | ATCTGATCAAAAGCAATTTTCTGAGTTTTCCGGGGAAAC | 29 |
| | CyPPO2Nt98%_R | CAATTGGATTTGAAGGTAACGGTTGCAGCTTATTTTCC | 30 |
| *Lyngbya* sp. PCC 8106 | CyPPO4-Nt-98%_F | ATCTGATCAAAAGCAATTTTTTAAGTCCTGGAGGTAAACT | 31 |
| | CyPPO4-Nt-98%_R | CAATTGGATTTGAAGGTAAAGGCATGAGTTGACCATTC | 32 |
| *Halothece* sp. PCC 7418 | CyPPO8_Nt98%-F | ATCTGATCAAAAGCAATTTTCTGAGTCCAATCGGGAAAC | 33 |
| | CyPPO8_Nt98%-R | CAATTGGATTTGAAGGTAAAGGGCGCAGTTTCCCCTCCC | 34 |

To prepare BT3(ΔPPO) competent cells, BT3(ΔPPO) strain was added to 5 ml of LB broth containing 50 μg/ml kanamycin and 20 μg/ml hematin, and cultured in a 37° C. shaking incubator for 12 hours in the dark. Thereafter, 5 ml of the culture was added to 100 ml of LB broth containing 20 μg/ml hematin, and cultured in a 37° C. shaking incubator in the dark until $OD_{600}$ reached 0.5. BT3(ΔPPO) competent cells were prepared from the cultured *E. coli* using $CaCl_2$ according to protocols for preparing competent cells. Next, to transform the BT3(ΔPPO) strain with the respective vectors harboring the CyPPO2 variant, CyPPO4 variant and CyPPO8 variant, 5 μl of the vector was added to 100 μl of BT3(ΔPPO) competent cells, and the mixture was mixed well, allowed to react on ice for 20 minutes, and then left at 42° C. for 40 seconds. After stabilization on ice for 2 minutes, 1 ml of LB broth was added to BT3(ΔPPO), and cultured at 37° C. for 1 hour with shaking. The cells cultured in the medium were collected according to the type of the gene insert, and then spread on LB solid medium containing chloramphenicol (34 μg/ml), and cultured at 37° C. for 12 hours or longer. Thereafter, single colonies thereof were cultured in LB liquid medium. Growth inhibition was measured according to herbicide treatment in the light, and compared with that of the BT3 transformed strain which was cultured on LB solid medium without herbicide, and growth of the BT3 transformed strain on LB solid medium with varying concentrations of herbicide was examined.

12-3. Experimental Result

FIGS. 22 to 25 show the results of examining herbicide resistance of CyPPO2 variant, CyPPO4 variant and CyPPO8 variant genes having 98% sequence homology to the original sequences of CyPPO2, CyPPO4 and CyPPO8, respectively. As a negative control, the wild-type AtPPO1 was employed as a reference for herbicide-sensitivity. As a positive control, the mutant AtPPO1 was employed as a reference for herbicide-resistance. If a strain shows resistance similar to or higher than that of the strain transformed with the mutant AtPPO1, it was determined that the strain has herbicide resistance.

As a result, respective BT3 strains transformed with CyPPO2 variant, CyPPO4 variant and CyPPO8 variant grew well in the light in all 13 types of herbicides from 9 families (Tiafenacil, Saflufenacil, Butafenacil, Fomesafen, Acifluorfen, Oxyfluorfen, Flumioxazin, Sulfentrazone, Pentoxazone, Pyraflufen-ethyl, Pyraclonil, Oxadiazon, Fluthiacet-methyl), and they showed herbicide resistance similar to or higher than that of the positive control mutant AtPPO1 (growth inhibitions thereof were hardly observed even at 25 μM).

Therefore, CyPPO2 variant, CyPPO4 variant and CyPPO8 variant having 98% sequence homology to CyPPO2, CyPPO4 and CyPPO8 also showed resistance similar to or higher than those of CyPPO2, CyPPO4 and CyPPO8, suggesting that although a part of the sequence of CyPPO2, CyPPO4 or CyPPO8 is altered, it maintains the PPO function and biological activity regarding herbicide resistance.

The invention claimed is:

1. A method of conferring herbicide resistance on a plant or an alga, the method comprising: transforming an alga, plant cell, protoplast, callus, hypocotyl, seed, cotyledon, shoot, or plant with a nucleotide sequence encoding a polypeptide consisting of the amino acid sequence of SEQ ID NO: 5, wherein the herbicide is selected from the group consisting of Tiafenacil, Saflufenacil, Butfenacil, Flumioxazin, Fomesafen, Actifluorfen, Oxyfluorfen, Sulfentrazone, Pentoxazone, Pyraflufen-ethyl, Oxadiozon, Fluthiacet-methyl, Pyraclonil, and a combination thereof.

2. The method of claim 1, wherein the nucleotide sequence consists of the nucleotide sequence of SEQ ID NO: 6 or a nucleotide sequence having 95% or higher sequence identity to the full length sequence.

3. The method of claim 1, wherein the coding sequence is included in the form of a recombinant plant expression vector or a recombinant algae expression vector.

4. The method of claim 1, wherein the plant is monocotyledonous plant, dicotyledonous plant, herbaceous plant, or woody plant.

5. The method of claim 1, wherein the plant or the alga additionally comprises a second nucleotide sequence encoding an herbicide-resistant polypeptide that confers resistance to a second herbicide.

6. The method of claim 5, wherein the second herbicide is selected from the group consisting of glyphosate, glufosinate, dicamba, 2,4-D (2,4-Dichlorophenoxyacetic acid), isoxaflutole, ALS (acetolactate synthase)-inhibiting herbicide, a photosystem II-inhibiting herbicide, a phenylurea-based herbicide, a bromoxynil-based herbicide, and a combination thereof.

7. The method of claim 5, wherein the second herbicide-resistant polypeptide is selected from the group consisting of EPSPS (5-enolpyruvylshikimate-3-phosphate synthase), GOX (glyphosate oxidase), GAT (glyphosate-N-acetyltransferase), glyphosate decarboxylase, PAT(phosphinothricin-N-acetyltransferase), DMO (monooxygenase), 2,4-D-monooxygenase, AAD (aryloxyalkanoate Dioxygenase), AHAS (acetohydroxyacid synthase), AtAHASL (Acetohydroxyacid synthase Large Subunit), photosystem II protein D1, cytochrome P450, HPPD (Hydroxylphenylpyruvate dioxygenase), nitrilase and a combination thereof.

8. The method of claim 5, wherein the nucleotide sequence encoding the second herbicide-resistant polypeptide is selected from the group consisting of CP4 EPSPS, MEPSPS, 2MEPSPS, GOXV247, GAT4601, GAT4621, BAR, PAT, DMO, ADD-1, AAD-12, HPPDPF W336, ALS, SCR1, CSR1-1, CSR1-2, GM-HRA, S4-HRA, ZM-HRA, SURA, SURB, PSBA, phenylurea herbicide-resistant CYP76B 1, BXN, and a combination thereof.

9. A transformant, clone or progeny thereof, having herbicide resistance, comprising the nucleotide sequence of claim 1.

10. The transformant, clone or progeny thereof of claim 9, wherein the transformant is plant cell, protoplast, callus, hypocotyl, seed, cotyledon, shoot, or plant.

11. A method of preparing a plant or an alga having herbicide resistance, the method comprising transforming a plant, plant cell, protoplast, callus, hypocotyl, seed, cotyledon, shoot, or alga with the nucleotide sequence of claim 1.

12. A method of controlling weeds in a cropland, the method comprising providing the cropland with a plant comprising the nucleotide sequence of claim 1, and applying an effective dosage of protoporphyrinogen oxidase-inhibiting herbicide to the croplands.

13. The method of claim 12, wherein the applying an effective dosage of a protoporphyrinogen oxidase-inhibiting herbicide to the cropland is performed by applying two or more combinations of protoporphyrinogen oxidase-inhibiting herbicides at an effective dosage thereof, sequentially or simultaneously.

14. The method of claim 12, wherein the plant further comprises a second nucleotide sequence encoding an herbicide resistant polypeptide that confers resistance to a second herbicide, and the method further comprises applying an effective amount of the protoporphyrinogen oxidase-inhibiting herbicide and the second herbicide to the cropland, sequentially or simultaneously.

15. A method of controlling undesired aquatic species in a cultivation medium, the method comprising providing the cultivation medium with an alga comprising the nucleotide sequence of claim 1, and applying an effective dosage of protoporphyrinogen oxidase-inhibiting herbicide to the cultivation medium.

* * * * *